(12) United States Patent
Zemolka et al.

(10) Patent No.: US 7,977,370 B2
(45) Date of Patent: Jul. 12, 2011

(54) (HETERO)ARYL CYCLOHEXANE DERIVATIVES

(75) Inventors: Saskia Zemolka, Aachen (DE); Stefan Schunk, Aachen (DE); Bert Nolte, Aachen (DE); Klaus Linz, Wachtberg (DE); Wolfgang Schröder, Aachen (DE); Werner Englberger, Stolberg (DE); Hans Schick, Berlin (DE); Helmut Sonnenschein, Berlin (DE); Birgitta Henkel, Berlin (DE); József Bálint, Berlin (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 12/410,692

(22) Filed: Mar. 25, 2009

(65) Prior Publication Data
US 2009/0247573 A1    Oct. 1, 2009

(30) Foreign Application Priority Data
Mar. 27, 2008   (EP) ..................... 08005797

(51) Int. Cl.
*A01N 43/38* (2006.01)
(52) U.S. Cl. ........ 514/415; 514/438; 548/469; 549/462; 549/29
(58) Field of Classification Search .................. 514/415, 514/438; 548/469; 549/29, 462
See application file for complete search history.

(56) References Cited

U.S. PATENT DOCUMENTS

| | | |
|---|---|---|
| 4,065,573 A | 12/1977 | Lednicer |
| 4,115,589 A | 9/1978 | Lednicer |
| 2009/0247505 A1 | 10/2009 | Zemolka et al. |
| 2009/0247530 A1 | 10/2009 | Nolte et al. |
| 2009/0247561 A1 | 10/2009 | Zemolka et al. |
| 2009/0247591 A1 | 10/2009 | Zemolka et al. |
| 2011/0059999 A1 | 3/2011 | Frormann et al. |

FOREIGN PATENT DOCUMENTS

| | | |
|---|---|---|
| AR | 071066 | 5/2010 |
| AR | 071067 | 5/2010 |
| AR | 071068 | 5/2010 |
| AR | 073841 | 12/2010 |
| AU | 2009228637 | 10/2009 |
| AU | 2009228642 | 10/2009 |
| AU | 2009228643 | 10/2009 |
| AU | 2009228645 | 10/2009 |
| AU | 2009228647 | 10/2009 |
| AU | 2009228648 | 10/2009 |
| CA | 2718209 | 10/2009 |
| CA | 2719735 | 10/2009 |
| CA | 2719736 | 10/2009 |
| CA | 2719739 | 10/2009 |
| CA | 2719742 | 10/2009 |
| CA | 2719743 | 10/2009 |
| DE | 28 39 891 | 4/1979 |
| EP | 2260022 | 10/2009 |
| EP | 2257526 | 12/2010 |
| EP | 2260021 | 12/2010 |
| EP | 2260042 | 12/2010 |
| EP | 2271613 | 1/2011 |
| EP | 2280941 | 2/2011 |
| KR | 20100132048 | 12/2010 |
| KR | 20100136521 | 12/2010 |
| MX | 2010009955 | 9/2010 |
| MX | 2010010337 | 10/2010 |
| MX | 2010010339 | 10/2010 |
| MX | 2010010407 | 10/2010 |
| MX | 2010010446 | 11/2010 |
| MX | 2010010448 | 11/2010 |
| PE | 16502009 | 11/2009 |
| PE | 16892009 | 11/2009 |
| PE | 16572009 A1 | 12/2009 |
| PE | 18222009 | 12/2009 |
| PE | 18232009 | 12/2009 |
| WO | 01 87838 | 11/2001 |
| WO | 02 90330 | 5/2002 |
| WO | 03 008370 | 7/2002 |
| WO | 02 090317 | 11/2002 |
| WO | 03 008731 | 1/2003 |
| WO | 03 080557 | 1/2003 |
| WO | 2004 043899 | 5/2004 |
| WO | 2004 043900 | 5/2004 |
| WO | 2004 043902 | 5/2004 |
| WO | 2004 043909 | 5/2004 |
| WO | 2004 043949 | 5/2004 |
| WO | 2004 043967 | 5/2004 |
| WO | 2005 063769 | 7/2005 |
| WO | 2005 066183 | 7/2005 |
| WO | 2005 110970 | 11/2005 |
| WO | 2005 110971 | 11/2005 |
| WO | 2005 110973 | 11/2005 |
| WO | 2005 110974 | 11/2005 |
| WO | 2005 110975 | 11/2005 |
| WO | 2005 110976 | 11/2005 |
| WO | 2005 110977 | 11/2005 |
| WO | 2006 018184 | 2/2006 |
| WO | 2006 108565 | 10/2006 |
| WO | 2007 079927 | 7/2007 |
| WO | 2007 079928 | 7/2007 |
| WO | 2007 079930 | 7/2007 |
| WO | 2007 079931 | 7/2007 |
| WO | 2007 124903 | 11/2007 |
| WO | 2008 009416 | 1/2008 |
| WO | 2008009415 | 1/2008 |

(Continued)

OTHER PUBLICATIONS

Katritzky et al., Synthesis 1989, pp. 66-79.

(Continued)

*Primary Examiner* — Yong Chu
*Assistant Examiner* — Valerie Rodriguez-Garcia
(74) *Attorney, Agent, or Firm* — Norris McLaughlin & Marcus, P.A.

(57) ABSTRACT

The invention relates to compounds that have an affinity to the µ-opioid receptor and the ORL1-receptor, methods for their production, medications containing these compounds and the use of these compounds for the treatment of pain and other conditions.

9 Claims, No Drawings

FOREIGN PATENT DOCUMENTS

| | | | |
|---|---|---|---|
| WO | 2009 011813 A1 | 10/2009 |
| WO | 2009118163 | 10/2009 |
| WO | 2009118168 | 10/2009 |
| WO | 2009118169 | 10/2009 |
| WO | 2009118171 | 10/2009 |
| WO | 2009118173 | 10/2009 |
| WO | 2009118174 | 10/2009 |

OTHER PUBLICATIONS

Shiner et al., J. am. Chem. Soc., 103, 1981, pp. 436-442.
Xia et al., Organic Letters, vol. 7, No. 7, 2005, pp. 1315-1318.
Messina et al., Tetrahedron, Asymmetry 11, 2000, pp. 1681-1685.
Greene et al., Protective Groups in Organic Synthesis; Wiley Interscience Publication; 3rd Edition, 1999.
Jirkovsky et al., J. Heterocycl. Chem., 12, 1975, pp. 937-940.
Beck et al., J. Chem. Soc. Perkin 1, 1992, pp. 813-822.
Shinada et al., Tetrahedron Letters, vol. 39, 1996, pp. 7099-7102.
Garden et al., Tetrahedron, 58, 2002, pp. 8399-8412.
Lednicer et al., J. Med. Chem., 23, 1980, pp. 424-430.
Williams et al., J. Org. Chem. 1980, 45, pp. 5082-5088.
Bandini et al. J. Org. Chem. 67, 2002, pp. 5386-5389.
Davis et al., J. Med. Chem. 35, 1992, pp. 177-184.
Yamagishi et al., J. Med. Chem. 35, 1992, pp. 2085-2094.
Gleave et al.; Bioorganic & Medicinal Chemistry Letters 8, 1998, pp. 1231-1236.
Sandmeyer, Helv.Chim.Acta; 2; 1919; 239 (cited on p. 53 of the specification).
Katz et al.; J. Med. Chem. 31, 1988; pp. 1244-1250.
Bac et al. Tetrahedron Letters, 1988, vol. 29, pp. 2819-2822.
Kato et al. J. Fluorine Chemistry, 99, 1999, pp. 5-7.
Kim et al., J.M, Pain, 50 (1992) 355-363.
Piper, et al; Journal of Medicinal Chemistry, US American Chemical Society, Washington, No. 9, Jan. 1, 1966; pp. 911-920.
Gilbert, et al; Journal of the American Chemical Society, 1950, No. 72, pp. 2411-2417.
Chu, et al.; Tetrahedron, Elsevier Science Publishers, Amsterdam, NL, No. 62, 2006, pp. 5536-5548.
Elliott et al. Bioorg. Med. Chem. Lett.; EN; 16; 2006; 2929.
Ma et al. J. Org. Chem. 2001, 66, 4525.
Bavetsias et al., "Design and Synthesis of Cyclopenta[g]quinazoline-Based Antifolates as Inhibitors of Thymidylate Synthase and Potential Antitumor Agents", J. Med. Chem, No. 43, pp. 1910-1926, (2000).
Catterall et al., "Binding of Batrachotoxinin a 20-α-Benzoate to a Receptor Site Associated with Sodium Channels in Synaptic Nerve Ending Particles", The Journal of Biological Chemistry, vol. 256, No. 17, pp. 8922-8927, Sep. 10, 1981.
Dirat et al., "Expeditious systhesis of novel NK1 antagonists based on a 1,2,4-trisubstituted cyclohexane", Tetrahedron Letters, No. 47, pp. 1295-1298, (2006).
Hamzé et al., "Systhesis of Various 3-Substituted 1,2,4-Oxadiazole-Containing Chiral B3- and α-Amino Acids from Fmoc-Protected Aspartic Acid", J. Org. Chem. No. 68, pp. 7316-7321, (2003).
Hashmi et al., "Gold Catalysis: Mild Conditions for the Synthesis of Oxazoles from N-Propargylcarboxamides and Mechanistic Aspects", Organic Letters, vol. 6, No. 23, pp. 4391-4394, (2004).
Lee et al., "Introduction of Heterocycles at the 2-position of Indoline as Ester Bioisosteres", Bull. Koren Chem. Soc. vol. 25, No. 2 pp. 207-212, (2004).
Morwick et al., "A Practical Approach to the Synthesis of 2,4-Disubstituted Oxazoles from Amino Acids", Organic Letters, vol. 4, No. 16, pp. 2665-2668, (2002).
Thompson et al., "Structure-Based Design of Cathepsin K Inhibitors Containing a Benzyloxy-Substituted Benzoyl Peptidomimetic", Journal of Medical Chemistry, vol. 41, No. 21, 1998, pp. 3923-3927.
Finlayson, et al., European Journal of Pharmacology, 412 (2001), pp. 203-212.
Corey et al., "A Synthetic Method for Formyl-ethynyl Conversion (RCHO-RC=CH or RC=CR')", Tetrahedron Letters, No. 36, pp. 3769-3772, (1972).
D'Amour et al., "A Method for Determining Loss of Pain Sensation", The Biologic Research Laboratory, pp. 74-79, Jan. 27, 1941.
Harned et al., "High-load, Soluble Oligomeric Benzenesulfonyl Azide: Application to Facile Diazo-transfer Reactions", Tetrahedron, No. 61, pp. 12093-12099, (2005).
Katritzky et al., "New Synthesis of Amines and Amides Mediated by Additions of Benzotriazole to Enamines and Enamides and Transformations of the Adducts", Synthesis, pp. 1295-1298, Dec. 1992.
Kudzma et al., "4-Phenyl- and a 4-Heteroaryl-4-anilidopiperidines. A Novel Class of Analgesic and Anesthetic Agents1", J. Med. Chem. No. 32, pp. 2534-2542, (1989).
Layer, Robert W. "The Chemistry of Imines", B.F. Goodrich Co., Research Center, pp. 489-510, Dec. 7, 1962.
Lednicer et al., "4-Amino-4-arylcyclohexanones and Their Derivatives, a Novel Class of Analgesics. 1. Modification of the Aryl Ring", The Upjohn Company, Research Laboratories, Aug. 7, 1979.
Maddox et al., "The Synthesis of Phencyclidine and Other 1-Arylcyclohexylamines", Research Laboratories, Parke, Davis and Company; vol. 8, pp. 230-235, Mar. 1965.
Prashad et al., "1,2,3-Triazole as a Safer and Practical Substitute for Cyanide in the Bruylants Reaction for the Synthesis of Tertiary Amines Containing Tertiary Alkyl or Aryl Groups", Tetrahedron Letters, No. 46, pp. 5455-5458, (2005).
Regitz et al., "Synthese von α-Diazo-phosphonsäureestern", Chem. Ber., No. 101, pp. 3734-3743, (1968).

(HETERO)ARYL CYCLOHEXANE DERIVATIVES

The invention relates to substituted cyclohexane derivatives that have an affinity to the μ-opioid receptor and the ORL 1-receptor, methods for their production, medications containing these compounds and the use of these compounds for the production of medications.

Cyclohexane derivatives that have an affinity to the μ-opioid receptor and the ORL 1-receptor are known in the prior art. In this context, reference can be made, for example, to the following documents in their full scope WO2002/090317, WO2002/90330, WO2003/008370, WO2003/008731, WO2003/080557, WO2004/043899, WO2004/043900, WO2004/043902, WO2004/043909, WO2004/043949, WO2004/043967, WO2005/063769, WO2005/066183, WO2005/110970, WO2005/110971, WO2005/110973, WO2005/110974, WO2005/110975, WO2005/110976, WO2005/110977, WO2006/018184, WO2006/108565, WO2007/079927, WO2007/079928, WO2007/079930, WO2007/079931, WO2007/124903, WO2008/009415 and WO2008/009416.

However, the known compounds are not satisfactory in every respect and there is a need for further compounds with comparable or better properties.

Thus, in appropriate binding assays the known compounds occasionally exhibit a certain affinity to the hERG ion channel, the L-type calcium ion channel (phenylalkylamine, benzothiazepine, dihydropyridine binding sites) or to the sodium channel in the BTX assay (batrachotoxin), which can be respectively interpreted as an indication of cardiovascular side-effects. Moreover, many of the known compounds exhibit only a slight solubility in aqueous media, which can adversely affect the bioavailability, inter alia. In addition, the chemical stability of the known compounds is often merely inadequate. Thus, the compounds occasionally do not exhibit an adequate pH, UV or oxidation stability, which can adversely affect the storage stability and also the oral bioavailability, inter alia. Moreover, the known compounds have an unfavourable PK/PD (pharmacokinetic/pharmacodynamic) profile in some instances, which can be displayed, for example, in too long a duration of effect.

The metabolic stability of the known compounds also appears to be in need of improvement. An improved metabolic stability can point to an increased bioavailability. A weak or absent interaction with transporter molecules that participate in the absorption and excretion of medicinal substances should be considered an indication of an improved bioavailability and possibly low interactions of medications. Moreover, the interactions with the enzymes involved in the breakdown and excretion of medicinal substances should also be as low as possible, since such test results also indicate that low interactions of medications or none at all are possibly to be expected.

Moreover, the known compounds at times exhibit an only low selectivity with respect to the kappa-opioid receptor, which is responsible for side-effects such as e.g. dysphoria, sedation, diuresis. In addition, the known compounds at times exhibit a very high affinity to the μ-opioid receptor, which appears to be associated with other side-effects, in particular respiratory depression, constipation and addiction dependence.

The object forming the basis of the invention is to provide compounds that are suitable for pharmaceutical purposes and have advantages over the compounds of the prior art.

This object is achieved by the compounds described hereinbelow.

It has been surprisingly found that substituted cyclohexane derivatives can be produced that have an affinity to the μ-opioid receptor and the ORL 1-receptor.

The invention relates to compounds of the general formula (1),

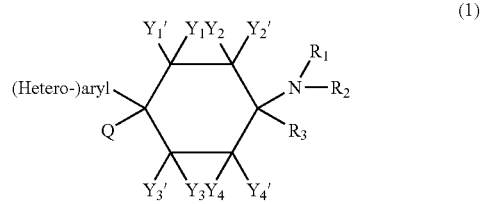

wherein
$Y_1, Y_1', Y_2, Y_2', Y_3, Y_3', Y_4$ and $Y_4'$ are respectively selected independently of one another from the group comprising —H, —F, —Cl, —Br, —I, —CN, —NO$_2$, —CHO, —R$_0$, —C(=O)R$_0$, —C(=O)H, —C(=O)—OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$, —NHC(=O)N(R$_0$)$_2$; preferably respectively selected independently of one another from the group comprising —H, —F, —Cl, —CN and —C$_{1-8}$-aliphatic; or $Y_1$ and $Y_1'$, or $Y_2$ and $Y_2'$, or $Y_3$ and $Y_3'$, or $Y_4$ and $Y_4'$ jointly stand for =O;
Q stands for —R$_0$;
R$_0$ respectively independently stands for —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl, —C$_{1-8}$-aliphatic-heteroaryl, —C$_{3-8}$-cycloaliphatic-C$_{1-8}$-aliphatic, —C$_{3-8}$-cycloaliphatic-aryl or —C$_{3-8}$-cycloaliphatic-heteroaryl;
R$_1$ and R$_2$, independently of one another, stand for —H or —R$_0$; or R$_1$ and R$_2$ together stand for —CH$_2$CH$_2$OCH$_2$CH$_2$—, —CH$_2$CH$_2$NCH$_2$CH$_2$— or —(CH$_2$)$_{3-6}$—;
R$_3$ stands for —R$_0$;
R$_4$ stands for —H, —Ro or —C(=O)R$_0$;
wherein
"aliphatic" respectively is a branched or unbranched, saturated or a mono- or polyunsaturated, unsubstituted or mono- or polysubstituted, aliphatic hydrocarbon residue;
"cycloaliphatic" respectively is a saturated or a mono- or polyunsaturated, unsubstituted or mono- or polysubstituted, alicyclic, mono- or multicyclic hydrocarbon residue, the number of ring-carbon atoms of which preferably lies in the specified range (i.e. "C$_{3-8}$-cycloaliphatic" preferably has 3, 4, 5, 6, 7 or 8 ring-carbon atoms);
wherein with respect to "aliphatic" and "cycloaliphatic", "mono- or polysubstituted" is understood to mean the mono- or polysubstitution, e.g. the mono-, di-, tri- or complete substitution, of one or more hydrogen atoms by substituents selected independently of one another from the group comprising aus —F, —Cl, —Br, —I, —CN, —NO$_2$, —CHO, =O, —R$_0$, —C(=O)R$_0$, —C(=O)H, —C(=O)OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O—, —NHC(=O)R$_0$, —NHC(=O)OR$_0$, —NHC(=O)NH$_2$, —NHC(=O)—NHR$_0$, —NH—C(=O)N(R$_0$)$_2$, —NHS(=O)$_{1-2}$R$_0$, —Si(R$_0$)$_3$ and —PO(OR$_0$)$_2$;

"(hetero-)aryl" stands for heteroaryl or aryl;

"aryl", respectively independently, stands for a carbocyclic ring system with at least one aromatic ring, but without heteroatoms in this ring, wherein, if necessary, the aryl residues can be condensed with further saturated, (partially) unsaturated or aromatic ring systems, and each aryl residue can be present in unsubstituted or mono- or polysubstituted form, wherein the aryl substituents can be the same or different and in any desired and possible position of the aryl;

"heteroaryl" stands for a 5-, 6- or 7-membered cyclic aromatic residue, which contains 1, 2, 3, 4 or 5 heteroatoms, wherein the heteroatoms, the same or different, are nitrogen, oxygen or sulphur, and the heterocycle can be unsubstituted or mono- or polysubstituted; wherein in the case of the substitution on the heterocycle the substituents can be the same or different and can be in any desired and possible position of the heteroaryl; and wherein the heterocycle can also be part of a bi- or polycyclic system;

wherein with respect to "aryl" and "heteroaryl", "mono- or polysubstituted" is understood to mean the mono- or polysubstitution of one or more hydrogen atoms of the ring system by substituents selected from the group comprising —F, —Cl, —Br, —I, —CN, —NO$_2$, —CHO, =O, —R$_0$, —C(=O)R$_0$, —C(=O)H, —C(=O)OH, —C(=O)OR$_0$, —C(=O)NH$_2$, —C(=O)NHR$_0$, —C(=O)—N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O, —NHC(=O)R$_0$, —NHC(=O)OR$_0$, —NH—C(=O)NH$_2$, —NHC(=O)NHR$_0$, —NHC(=O)N(R$_0$)$_2$, —Si(R$_0$)$_3$, —PO(OR$_0$)$_2$, —C$_{1-8}$-aliphatic-NHC(=O)R$_0$, —C$_{1-8}$-aliphatic-NHC(=O)OR$_0$, —C$_{1-8}$-aliphatic-NHC(=O)NHR$_0$, —C$_{1-8}$-aliphatic-NHC(=O)N(R$_0$)$_2$ and —C$_{1-8}$-aliphatic-NHC(=O)$_{1-2}$R$_0$; wherein any N-ring atoms present can be respectively oxidised (N-oxide);

in the form of a single stereoisomer or mixture thereof, the free compounds and/or their physiologically compatible salts and/or solvates.

In the combination of different residues, e.g. Y$_1$, Y$_1'$, Y$_2$, Y$_2'$, Y$_3$, Y$_3'$, Y$_4$ and Y$_4'$, and also the combination of residues at substituents thereof such as e.g. —OR$_0$, —OC(=O)R$_0$, —OC(=O)NHR$_0$, a substituent, e.g. R$_0$, can assume different meanings within a substance for two or more residues, e.g. —OR$_0$, —OC(=O)R$_0$, —OC(=O)NHR$_0$.

The compounds according to the invention exhibit favourable binding to the ORL 1-receptor and the β-opioid receptor.

In a preferred embodiment, the compounds according to the invention have an affinity ratio of ORL1/μ of at least 0.1. The ORL1/μ ratio is defined as $1/[K_{i(ORL1)}/K_{i(\mu)}]$. It is particularly preferred if the ORL1/μ ratio amounts to at least 0.2 or at least 0.5, more preferred at least 1.0 or at least 2.0, further preferred at least 3.0 or at least 4.0, most preferred at least 5.0 or at least 7.5 and in particular at least 10 or at least 15. In a preferred embodiment the ORL1/μ ratio lies in the range of 0.1 to 30, more preferred 0.1 to 25.

In another preferred embodiment, the compounds according to the invention have an ORL1/μ affinity ratio of more than 30, more preferred at least 50, further preferred at least 100, most preferred at least 200 and in particular at least 300.

The compounds according to the invention preferably have a K$_i$ value on the μ-opioid receptor of at maximum 500 nM, more preferred at maximum 100 nM, further preferred at maximum 50 nM, most preferred at maximum 10 nM and in particular at maximum 1.0 nM.

Methods for determining the K$_i$ value on the μ-opioid receptor are known to the person skilled in the art. The determination is preferably conducted as described in association with the examples.

It has surprisingly been shown that compounds with affinity to the ORL 1- and μ-opioid receptor, in which the ratio of ORL 1 to μ defined by $1/[K_{i(ORL1)}/K_{i(\mu)}]$ lies in the range of 0.1 to 30, preferably 0.1 to 25, have a pharmacological profile that has significant advantages compared to the other opioid receptor ligand:

1. The compounds according to the invention exhibit an efficacy in acute pain models that is at times comparable with the usual stage-3 opioids. However, they are distinguished at the same time by a significantly better compatibility compared to classic μ-opioids.
2. In contrast to common stage-3 opioids, the compounds according to the invention exhibit a significantly higher efficacy in mono- and polyneuropathic pain models, which is attributable to a synergy of ORL 1- and μ-opioid components.
3. In contrast to common stage-3 opioids, the compounds according to the invention exhibit in neuropathic animals a substantial, preferably a complete, separation of antiallodynic or antihyperalgesic effect and antinociceptive effect.
4. In contrast to common stage-3 opioids, in animal models the compounds according to the invention exhibit a significant increase in efficacy for chronic inflammatory pain (carageenan- or CFA-induced hyperalgesia, visceral inflammatory pain, amongst others) compared to acute pain.
5. In contrast to common stage-3 opioids, side-effects typical of μ-opioids (respiratory depression, opioid-induced hyperalgesia, physical dependence/withdrawal, psychic dependence/addiction, among others) are significantly reduced or preferably not observed with the compounds according to the invention in the therapeutically effective dose range.

In view of the reduced μ-opioid side-effects, on the one hand, and the increased efficacy in chronic, preferably neuropathic pain, on the other hand, the mixed ORL 1/μ agonists are thus distinguished by significantly increased safety margins compared to pure μ-opioids. This results in a significantly increased "therapeutic window" in the treatment of pain conditions, preferably chronic pain, more preferred neuropathic pain.

It is preferred if Y$_1$, Y$_1'$, Y$_2$, Y$_2'$, Y$_3$, Y$_3'$, Y$_4$ and Y$_4'$ are respectively selected independently of one another from the group comprising —H, —F, —Cl, —Br, —I, —CN, —NH$_2$, —NH—C$_{1-6}$-aliphatic, —NH—C$_{3-8}$-cycloaliphatic, —NH—C$_{1-6}$-aliphatic-OH, —N(C$_{1-6}$-aliphatic)$_2$, —N(C$_{3-8}$-cycloaliphatic)$_2$, —N(C$_{1-6}$-aliphatic-OH)$_2$, —NO$_2$, —NH—C$_{1-6}$-aliphatic-C$_{3-8}$-cycloaliphatic, —NH—C$_{1-6}$-aliphatic-aryl, —NH—C$_{1-6}$-aliphatic-heteroaryl, —NH-aryl, —NH-heteroaryl, —SH, —S—C$_{1-6}$-aliphatic, —S—C$_{3-8}$-cycloaliphatic, —S—C$_{1-6}$-aliphatic-C$_{3-8}$-cycloaliphatic, —S—C$_{1-6}$-aliphatic-aryl, —S—C$_{1-6}$-aliphatic-heteroaryl, —S-aryl, —S-heteroaryl, —OH, —O—C$_{1-6}$-aliphatic, —O—C$_{3-8}$-cycloaliphatic, —O—C$_{1-6}$-aliphatic-OH, —O—C$_{1-6}$-aliphatic-C$_{3-8}$-cycloaliphatic, —O—C$_{1-6}$-aliphatic-aryl, —O—C$_{1-6}$-aliphatic-heteroaryl, —O-aryl, —O-heteroaryl, —O—C(=O)C$_{1-6}$-aliphatic, —O—C(=O)C$_{3-8}$-cycloaliphatic, —O—C(=O)C$_{1-6}$-aliphatic-OH, —O—C(=O)C$_{1-6}$-aliphatic-C$_{3-8}$-cycloaliphatic, —O—C(=O)C$_{1-6}$-aliphatic-aryl, —O—C(=O)C$_{1-6}$-aliphatic-heteroaryl, —O—C(=O)aryl, —O—C(=O)heteroaryl, —C$_{1-6}$-aliphatic, —C$_{3-8}$-cycloaliphatic, —C$_{1-6}$-aliphatic-C$_{3-8}$-cycloaliphatic, —C$_{1-6}$-aliphatic-aryl, —C$_{1-6}$-aliphatic-heteroaryl, -aryl, -heteroaryl, —C(=O)C$_{1-6}$-aliphatic, —C(=O)C$_{3-8}$-cycloaliphatic, —C(=O)C$_{1-6}$-aliphatic-C$_{3-8}$-cycloaliphatic, —C(=O)C$_{1-6}$-aliphatic-aryl, —C(=O)C$_{1-6}$-aliphatic-heteroaryl, —C(=O)aryl, —C(=O)heteroaryl, —CO$_2$H, —CO$_2$—C$_{1-6}$-aliphatic, —CO$_2$—C$_{3-8}$-cycloaliphatic, —CO$_2$—C$_{1-6}$-aliphatic-C$_{3-8}$-cycloaliphatic, —CO$_2$—C$_{1-6}$-aliphatic-aryl, —CO$_2$—C$_{1-6}$-aliphatic-heteroaryl, —CO$_2$-aryl, —CO$_2$-heteroaryl; or Y$_1$ and Y$_1$', or Y$_2$ and Y$_2$', or Y$_3$ and Y$_3$', or Y$_4$ and Y$_4$' jointly stand for =O. It is preferred if Y$_1$, Y$_1$', Y$_2$, Y$_2$', Y$_3$, Y$_3$', Y$_4$ and Y$_4$' are respectively selected independently of one another from the group comprising —H, —F, —Cl, —Br, —I, —CN, —NH$_2$ and —OH.

In a preferred embodiment one of the residues Y$_1$, Y$_1$', Y$_2$, Y$_2$', Y$_3$, Y$_3$', Y$_4$ and Y$_4$' differs from —H and the remaining residues stand for —H.

It is particularly preferred if Y$_1$, Y$_1$', Y$_2$, Y$_2$', Y$_3$, Y$_3$', Y$_4$ and Y$_4$' respectively stand for —H.

Q preferably stands for —C$_{1-8}$-aliphatic, -aryl, -heteroaryl, —C$_{1-8}$-aliphatic-aryl or —C$_{1-8}$-aliphatic-heteroaryl; more preferred -aryl or -heteroaryl. In this case, -aliphatic, -aryl and -heteroaryl can be respectively unsubstituted or mono- or polysubstituted, preferably with substituents selected independently of one another from the group comprising —C$_{1-8}$-aliphatic, —OH, —OC$_{1-8}$-aliphatic, —CF$_3$, —F, —Cl, —Br, —NO$_2$, —CN, -heteroaryl, —C$_{1-8}$-aliphatic-aryl and —C$_{1-8}$-aliphatic-heteroaryl (e.g. -ethyl-4-pyridyl).

In a preferred embodiment Q is selected from the group comprising —C$_{1-8}$-alkyl, -phenyl, -benzyl, -pyrrolyl, -furyl, -thienyl, -pyridyl, -indolyl, -benzofuryl and -benzothienyl, wherein these can respectively be unsubstituted or mono- or polysubstituted, preferably with substituents selected independently of one another from the group comprising —C$_{1-8}$-aliphatic, —OH, —OC$_{1-8}$-aliphatic, —CF$_3$, —F, —Cl, —Br, —NO$_2$, —CN, -heteroaryl, —C$_{1-8}$-aliphatic-aryl and —C$_{1-8}$-aliphatic-heteroaryl (e.g. -ethyl-4-pyridyl).

It is particularly preferred if Q is selected from the group comprising:

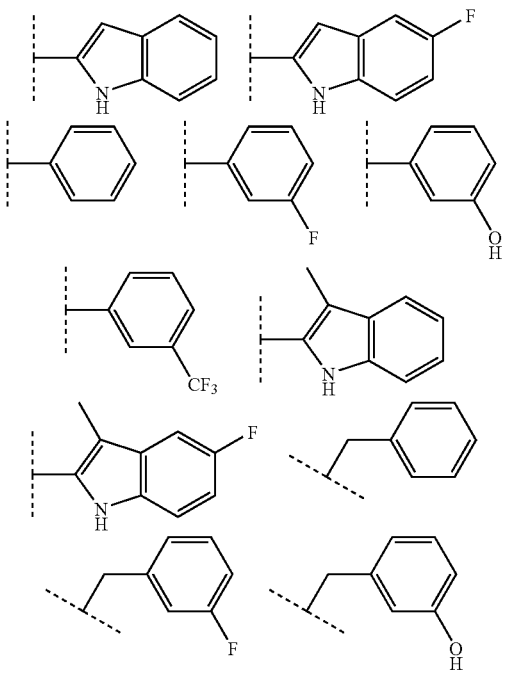

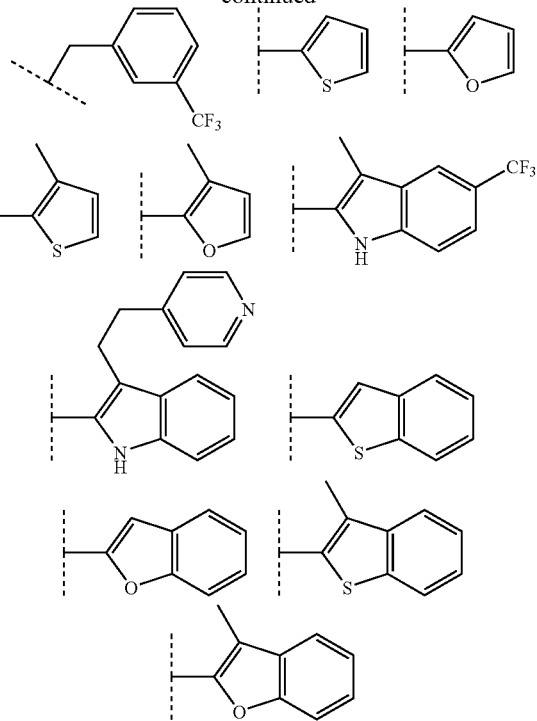

If Q stands for -heteroaryl or -aryl, then Q can be the same as or different from the geminally bonded residue "-(hetero)aryl". In a preferred embodiment the two geminally bonded residues Q and (hetero)aryl are identical, in another preferred embodiment they are different from one another.

R$_0$, respectively independently, preferably stands for —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl or —C$_{1-8}$-aliphatic-heteroaryl. In this case —C$_{1-8}$-aliphatic-C$_{3-12}$-cycloaliphatic, —C$_{1-8}$-aliphatic-aryl or —C$_{1-8}$-aliphatic-heteroaryl mean that the residues —C$_{3-12}$-cycloaliphatic, -aryl or -heteroaryl are respectively bonded via a bivalent bridge —C$_{1-8}$-aliphatic-. Preferred examples of —C$_{1-8}$-aliphatic-aryl are —CH$_2$—C$_6$H$_5$, —CH$_2$CH$_2$—C$_6$H$_5$, and —CH=CH—C$_6$H$_5$.

R$_1$ and R$_2$, independently of one another, preferably stand for —H; —C$_{1-6}$-aliphatic; —C$_{3-8}$-cyclo-aliphatic, —C$_{1-6}$-aliphatic-aryl, —C$_{1-6}$-aliphatic-C$_{3-8}$-cycloaliphatic or —C$_{1-6}$-aliphatic-heteroaryl; or the residues R$_1$ and R$_2$ together form a ring and represent —CH$_2$CH$_2$OCH$_2$CH$_2$—, —CH$_2$CH$_2$NR$_4$CH$_2$CH$_2$— or —(CH$_2$)$_{3-6}$—. It is more preferred if R$_1$ and R$_2$, independently of one another, stand for —H; —C$_{1-5}$-aliphatic; or the residues R$_1$ and R$_2$ together form a ring and represent —CH$_2$CH$_2$OCH$_2$CH$_2$—, —CH$_2$CH$_2$NR$_4$—CH$_2$CH$_2$— or —(CH$_2$)$_{3-6}$—, wherein R$_4$ preferably represents —H or —C$_{1-5}$-aliphatic. Particularly preferred are those compounds, in which R$_1$ and R$_2$, independently of one another, stand for —CH$_3$ or —H, wherein R$_1$ and R$_2$ do not simultaneously represent —H; or R$_1$ and R$_2$ form a ring and represent —(CH$_2$)$_{3-4}$—. Compounds, in which R$_1$ and R$_2$ stand for —CH$_3$ or in which R$_1$ stands for —H and R$_2$ stands for —CH$_3$, are most particularly preferred.

It is particularly preferred if R$_1$ and R$_2$ together with the nitrogen atom, to which they are bonded, form one of the following functional groups:

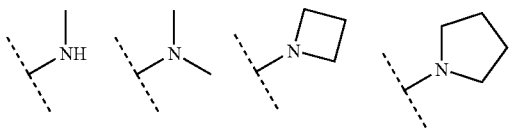

$R_3$ preferably stands for —$C_{1-8}$-aliphatic, —$C_{3-8}$-cycloaliphatic, -aryl, -heteroaryl; or for -aryl, -heteroaryl or —$C_{3-8}$-cycloaliphatic respectively bonded via a —$C_{1-3}$-aliphatic group.

It is particularly preferred if $R_3$ stands for -ethyl, -propyl, -butyl, -pentyl, -hexyl, -heptyl, -cyclopentyl, -cyclohexyl, -phenyl, -benzyl, -naphthyl, -anthracenyl, -thiophenyl, -benzothio-phenyl, -furyl, -benzofuranyl, -benzodioxolanyl, -indolyl, -indanyl, -benzodioxanyl, -pyrrolyl, -pyridyl, -pyrimidyl or -pyrazinyl, respectively unsubstituted or mono- or polysubstituted; —$C_{5-6}$-cycloaliphatic, -phenyl, -naphthyl, -anthracenyl, -thiophenyl, -benzothiophenyl, -pyridyl, -furyl, -benzofuranyl, -benzodioxolanyl, -indolyl, -indanyl, -benzodioxanyl, -pyrrolyl, -pyrimidyl, -triazolyl or -pyrazinyl, respectively unsubstituted or mono- or polysubstituted, bonded via a saturated, unbranched —$C_{1-3}$-aliphatic group.

It is more preferred if $R_3$ stands for -propyl, -butyl, -pentyl, -hexyl, -phenyl, -furyl, -thiophenyl, -naphthyl, -benzyl, -benzofuranyl, -indolyl, -indanyl, -benzodioxanyl, -benzodioxolanyl, -pyridyl, -pyrimidyl, -pyrazinyl, -triazolyl or -benzothiophenyl, respectively unsubstituted or mono- or polysubstituted; -phenyl, -furyl or -thiophenyl, respectively unsubstituted or mono- or polysubstituted, bonded via a saturated, unbranched —$C_{1-3}$-aliphatic group.

It is further preferred if $R_3$ stands for -propyl, -butyl, -pentyl, -hexyl, -phenyl, -phenethyl, -thiophenyl, -pyridyl, -triazolyl, -benzothiophenyl or -benzyl, respectively substituted or unsubstituted, particularly preferred for -propyl, -3-methoxypropyl, -butyl, -pentyl, -hexyl, -phenyl, -3-methylphenyl, -3-fluorophenyl, -benzo[1,3]-dioxolyl, -thienyl, -benzothiophenyl, -4-chlorobenzyl, -benzyl, -3-chlorobenzyl, -4-methylbenzyl, -2-chlorobenzyl, -4-fluorobenzyl, -3-methylbenzyl, -2-methylbenzyl, -3-fluorobenzyl, -2-fluorobenzyl, -1-methyl-1,2,4-triazolyl or -phenethyl.

It is especially preferred if $R_3$ stands for -butyl, -ethyl, -3-methoxypropyl, -benzothiophenyl, -phenyl, -3-methylphenyl, -3-fluorophenyl, -benzo[1,3]-dioxolyl, -benzyl, -1-methyl-1,2,4-triazolyl, -thienyl or -phenethyl.

It is most preferred if $R_3$ stands for -phenyl, -benzyl or -phenethyl, respectively unsubstituted or mono- or polysubstituted on the ring; —$C_{1-5}$-aliphatic, —$C_{4-6}$-cycloaliphatic, -pyridyl, -thienyl, -thiazolyl, -imidazolyl, -1,2,4 triazolyl or -benzimidazolyl, unsubstituted or mono- or polysubstituted.

It is particularly preferred if $R_3$ stands for -phenyl, -benzyl, -phenethyl, -thienyl, -pyridyl, -thiazolyl, -imidazolyl, -1,2,4 triazolyl, -benzimidazolyl or -benzyl, unsubstituted or mono- or polysubstituted with —F, —Cl, —Br, —CN, —$CH_3$, —$C_2H_5$, —$NH_2$, —$NO_2$, —SH, —$CF_3$, —OH, —$OCH_3$, —$OC_2H_5$ or —$N(CH_3)_2$; -ethyl, -n-propyl, -2-propyl, -allyl, -n-butyl, -iso-butyl, -sec-butyl, -tert-butyl, -n-pentyl, -iso-pentyl, -neo-pentyl, -n-hexyl, -cyclopentyl or -cyclohexyl, respectively unsubstituted or mono- or polysubstituent with —OH, —$OCH_3$ or —$OC_2H_5$, wherein -thienyl, -pyridyl, -thiazolyl, -imidazolyl, -1,2,4-triazolyl and -benzimidazolyl are preferably unsubstituted.

It is particularly preferred if $R_3$ stands for -phenyl, unsubstituted or mono-substituted with —F, —Cl, —CN, —$CH_3$; -thienyl; -ethyl, -n-propyl or -n-butyl, unsubstituted or mono- or polysubstituted with —$OCH_3$, —OH or —$OC_2H_5$, in particular with —$OCH_3$.

$R_4$ preferably stands for —H, —$C_{1-5}$-aliphatic, —$C_{3-8}$-cycloaliphatic, -aryl, -heteroaryl, —$C_{1-6}$-aliphatic-aryl, —$C_{1-6}$-aliphatic-$C_{3-8}$-cycloaliphatic, —$C_{1-6}$-aliphatic-heteroaryl, —C(=O)aryl, —C(=O)heteroaryl, or —C(=O)$C_{1-6}$-aliphatic, more preferred for —H or —$C_{1-5}$-aliphatic.

For the purposes of the description hydrocarbon residues are divided into aliphatic hydrocarbon residues and aromatic hydrocarbon residues.

Aliphatic hydrocarbon residues are themselves divided into non-cyclic aliphatic hydrocarbon residues (="aliphatic") and cyclic aliphatic hydrocarbon residues, i.e. alicyclic hydrocarbon residues (="cycloaliphatic"). Cycloaliphatic compounds can be monocyclic or multicyclic. Alicyclic hydrocarbon residues ("cycloaliphatic") comprise both pure aliphatic carbocycles and aliphatic heterocycles, i.e.—unless expressly specified—"cycloaliphatic" comprises pure aliphatic carbocycles (e.g. cyclohexyl), pure aliphatic heterocycles (e.g. piperidyl or piperazyl) and also non-aromatic, multicyclic, possibly mixed, systems (e.g. decalinyl, decahydroquinolinyl).

Aromatic hydrocarbons are themselves divided into carbocyclic aromatic hydrocarbons (="aryl") and heterocyclic aromatic hydrocarbons (="heteroaryl").

The classification of multicyclic, at least partially aromatic systems preferably depends on whether at least one aromatic ring of the multicyclic system has at least one heteroatom (usually N, O or S) in the ring. If at least one such heteroatom is present in this ring, this is preferably a "heteroaryl" (even if a further carbocyclic aromatic or non-aromatic ring with or without heteroatom is possibly present as additionally present cycle of the multicyclic system); if such a heteroatom is not present in any of the possibly several aromatic rings of the multicyclic system, then this is preferably "aryl" (even if a ring heteroatom is present in a possibly additionally present non-aromatic cycle of the multicyclic system).

Therefore, the following priority in the classification applies within the cyclic substituents: heteroaryl>aryl>cycloaliphatic.

For the purposes of the description monovalent and multivalent, i.e. bivalent, hydrocarbon residues are not distinguished between conceptually, i.e. depending on the context, "$C_{1-3}$-aliphatic" covers e.g. —$C_{1-3}$-alkyl, —$C_{1-3}$-alkenyl and —$C_{1-3}$-alkinyl, as well as e.g. —$C_{1-3}$-alkylene-, —$C_{1-3}$-alkenylene- and $C_{1-3}$-alkinylene.

Aliphatic is preferably respectively a branched or unbranched, saturated or a mono- or polyunsaturated, unsubstituted or mono- or polysubstituted, aliphatic hydrocarbon residue. Where aliphatic is mono- or polysubstituted, the substituents are selected independently of one another from the group comprising —F, —Cl, —Br, —I, —CN, —$NO_2$, —CHO, =O, —$R_0$, —C(=O)$R_0$, —C(=O)OH, —C(=O)$OR_0$, —C(=O)$NH_2$, —C(=O)$NHR_0$, —C(=O)$N(R_0)_2$, —OH, —$OR_0$, —OC(=O)H, —OC(=O)$R_0$, —OC(=O)$OR_0$, —OC(=O)$NHR_0$, —OC(=O)$N(R_0)_2$, —SH, —$SR_0$, —$SO_3H$, —$S(=O)_{1-2}$—$R_0$, —$S(=O)_{1-2}NH_2$, —$NH_2$, —$NHR_0$, —$N(R_0)_2$, —$N^+(R_0)_3$, —$N^+(R_0)_2O^-$, —NHC(=O)$R_0$, —NHC(=O)$OR_0$, —NHC(=O)$NH_2$, —NHC(=O)$NHR_0$, —NHC(=O)$N(R_0)_2$, —NHS(=O)$_{1-2}R_0$, —Si$(R_0)_3$, —PO$(OR_0)_2$. Thus, "aliphatic" covers acyclic saturated or unsaturated hydrocarbon residues that can be branched or straight-chain, i.e. alkanyls, alkenyls and alkinyls. In this case, alkenyls have at least one C=C double bond and alkinyls have at least one C≡C triple bond. Preferred unsubstituted monovalent aliphatics comprise —$CH_3$, —CH₂CH₃, —CH₂CH₂CH₃, —CH(CH₃)₂, —CH₂CH₂CH₂CH₃, —CH(CH₃)CH₂CH₃, —CH₂CH(CH₃)₂, —C(CH₃)₃, —CH₂CH₂CH₂—CH₂CH₃ and —CH₂CH₂CH₂CH₂CH₃; but also —CH═CH₂, —C≡CH, —CH₂CH═CH₂, —CH═CHCH₃, —CH₂C≡CH, —C≡CCH₃ and —CH═CHCH═CH₂. Preferred unsubstituted bivalent aliphatics comprise —CH₂—, —CH₂CH₂—, —CH₂CH(CH₃)—, —CH(CH₃)—CH₂—, —CH₂CH₂CH₂—, —CH(CH₃)CH₂CH₂—, —CH₂CH(CH₃)—CH₂—, —CH₂CH₂CH(CH₃)—, —CH—(CH₂CH₃)CH₂— and —CH₂CH₂—CH₂CH₂—; but also —CH═CH—, —C═C—, —CH₂CH═CH—, —CH═CHCH₂—, —CH₂C═C— and —C═CCH₂—. Preferred substituted monovalent aliphatics comprise —CH₂F, —CHF₂, —CF₃, —CH₂CF₃, —CF₂CF₃, —CH₂OH, —CH₂CH₂OH, —CH₂CHOHCH₃, —CH₂OCH₃ and —CH₂CH₂OCH₃. Preferred substituted bivalent aliphatics comprise —CF₂—, —CF₂CF₂—, —CH₂CHOH—, —CHOHCH₂— and —CH₂CHOHCH₂—. -Methyl-, -ethyl-, -n-propyl- and -n-butyl- are particularly preferred.

Cycloaliphatic is preferably respectively a saturated or a mono- or polyunsaturated, unsubstituted or mono- or polysubstituted, aliphatic (i.e. not aromatic), mono- or multicyclic hydrocarbon residue. The number of ring-carbon atoms preferably lies in the specified range (i.e. a "C₃₋₈-cycloaliphatic" preferably has 3, 4, 5, 6, 7 or 8 ring-carbon atoms). For the purposes of the description "C₃₋₈-cycloaliphatic" is preferably a cyclic hydrocarbon with 3, 4, 5, 6, 7 or 8 ring-carbon atoms, saturated or unsaturated, but not aromatic, wherein possibly one or two carbon atoms are replaced independently of one another by a heteroatom S, N or O. Where cycloalkyl is mono- or polysubstituted, the substituents are selected independently of one another from the group comprising —F, —Cl, —Br, —I, —CN, —NO₂, —CHO, ═O, —R₀, —C(═O)R₀, —C(═O)OH, —C(═O)OR₀, —C(═O)NH₂, —C(═O)NHR₀, —C(═O)N(R₀)₂, —OH, —OR₀, —OC(═O)H, —OC(═O)R₀, —OC(═O)OR₀, —OC(═O)NHR₀, —OC(═O)—N(R₀)₂, —SH, —SR₀, —SO₃H, —S(═O)₁₋₂—R₀, —S(═O)₁₋₂NH₂, —NH₂, —NHR₀, —N(R₀)₂, —N⁺(R₀)₃, —N⁺(R₀)₂O⁻, —NHC(═O)R₀, —NHC(═O)OR₀, —NHC(═O)NH₂, —NHC(═O)NHR₀, —NHC(═O)N(R₀)₂, —NHS(═O)₁₋₂R₀, —Si(R₀)₃, —PO(OR₀)₂. Advantageously, C₃₋₈-cycloaliphatic is selected from the group comprising cyclopropyl, cyclobutyl, cyclopentyl, cyclohexyl, cycloheptyl, cyclooctyl, cyclopentenyl, cyclohexenyl, cycloheptenyl and cyclooctenyl, but also tetra-hydropyranyl, dioxanyl, dioxolanyl, morpholinyl, piperidinyl, piperazinyl, pyrazolinonyl and pyrrolidinyl.

In association with "aliphatic" or "cycloaliphatic", "mono- or polysubstituted" is preferably understood to mean the mono- or polysubstitution, e.g. the mono-, di-, tri- or 4-substitution, of one or more hydrogen atoms by —F, —Cl, —Br, —I, —OH, —OC₁₋₆-alkyl, —OC(═O)C₁₋₆-alkyl, —SH, —NH₂, —NHC₁₋₆-alkyl, —N(C₁₋₆-alkyl)₂, —C(═O)OC₁₋₆-alkyl or —C(═O)OH. Compounds, wherein "aliphatic substituted" or "cycloaliphatic substituted" means aliphatic or cycloaliphatic substituted with —F, —Cl, —Br, —I, —CN, —CH₃, —C₂H₅, —NH₂, —NO₂, —SH, —CF₃, —OH, —OCH₃, —OC₂H₅ or —N(CH₃)₂, are preferred. Particularly preferred substituents are —F, —Cl, —OH, —SH, —NH₂ and —C(═O)OH.

Polysubstituted residues are understood to be those residues that are polysubstituted, e.g. twice or three times either at different or at the same atoms, e.g. three times at the same C-atom, as in the case of —CF₃ or —CH₂CF₃, or at different sites, as in the case of —CH(OH)—CH═CH—CHCl₂. The polysubstitution can occur with the same or with different substituents. A substituent may also be substituted itself. Thus, —Oaliphatic also covers —OCH₂CH₂O—CH₂CH₂OH, amongst others. It is preferred if aliphatic or cycloaliphatic is substituted with —F, —Cl, —Br, —I, —CN, —CH₃, —C₂H₅, —NH₂, —NO₂, —SH, —CF₃, —OH, —OCH₃, —OC₂H₅ or —N(CH₃)₂. It is most particularly preferred if aliphatic or cycloaliphatic is substituted with —OH, —OCH₃ or —OC₂H₅.

(Hetero)aryl stands for heteroaryl or aryl. In this case -aryl and -heteroaryl can respectively be unsubstituted or mono- or polysubstituted, preferably with substituents selected independently of one another from the group comprising —C₁₋₈-aliphatic, —OH, —OC₁₋₈-aliphatic, —CF₃, —F, —Cl, —Br, —NO₂, —CN, -heteroaryl, —C₁₋₈-aliphatic-aryl and —C₁₋₈-aliphatic-heteroaryl (e.g. -ethyl-4-pyridyl).

In a preferred embodiment (hetero)aryl is selected from the group comprising phenyl, benzyl, pyrrolyl, furyl, thienyl, pyridyl, indolyl, benzofuryl and benzothienyl, wherein these can respectively be unsubstituted or mono- or polysubstituted, preferably with substituents selected independently of one another from the group comprising —C₁₋₈-aliphatic, —OH, —OC₁₋₈-aliphatic, —CF₃, —F, —Cl, —Br, —NO₂, —CN, -aryl, -heteroaryl, —C₁₋₈-aliphatic-aryl and —C₁₋₈-aliphatic-heteroaryl (e.g. -ethyl-4-pyridyl).

It is particularly preferred if (hetero)aryl is selected from the group comprising:

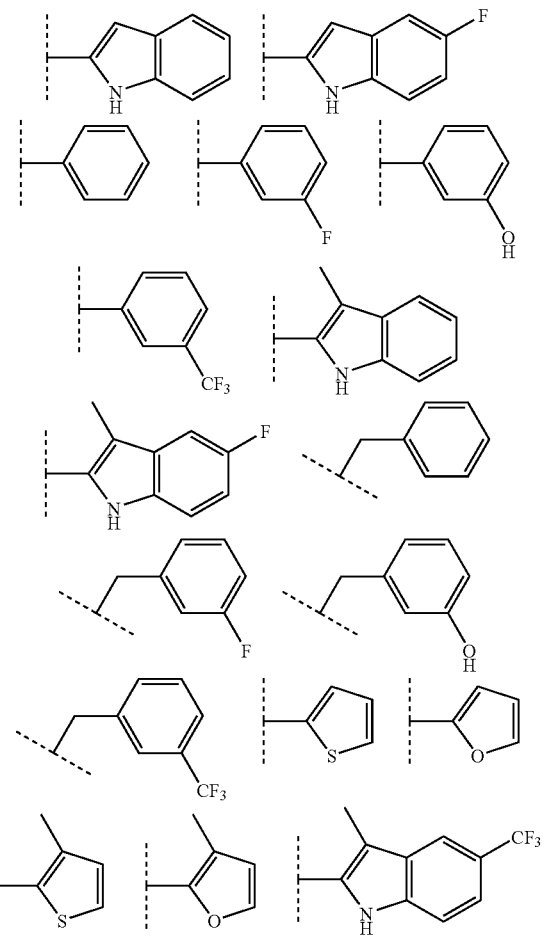

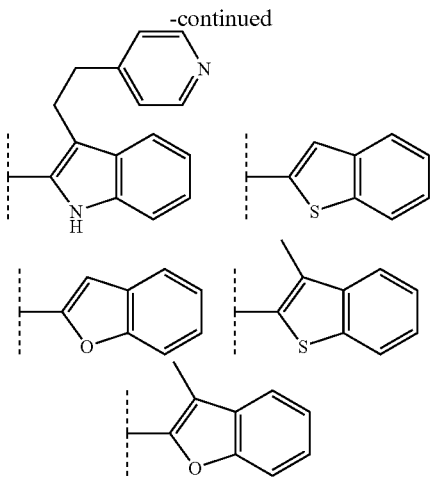

It is preferred if aryl respectively independently stands for a carbocyclic ring system with at least one aromatic ring, but without heteroatoms in this ring, wherein the aryl residues can possibly be condensed with further saturated, (partially) unsaturated or aromatic ring systems and each aryl residue can be present in unsubstituted or mono- or polysubstituted form, wherein the aryl substituents are the same or different and can be in any desired and possible position of the aryl. Preferred aryls are phenyl, naphthyl, anthracenyl, phenanthrenyl, fluoroanthenyl, fluoroenyl, indanyl and tetralinyl. Phenyl and naphthyl are particularly preferred. Where aryl is mono- or polysubstituted, the aryl substituents can be the same or different and be in any desired and possible position of the aryl, and are selected independently of one another from the group comprising —F, —Cl, —Br, —I, —CN, —NO$_2$, —CHO, =O, —R$_0$, —C(=O)R$_0$, —C(=O)OH, —C(=O)OR$_0$, —C(=O)NH$_2$, —C(=O)NHR$_0$, —C(=O)N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O—, —NHC(=O)R$_0$, —NHC(=O)OR$_0$, —NHC(=O)NH$_2$, —NHC(=O)NHR$_0$, —NHC(=O)N(R$_0$)$_2$, —Si(R$_0$)$_3$, —PO(OR$_0$)$_2$, —C$_{1-8}$aliphatic-NHC(=O)R$_0$, —C$_{1-8}$-aliphatic-NHC(=O)OR$_0$, —C$_{1-8}$-aliphatic-NHC(=O)NHR$_0$, —C$_{1-8}$-aliphatic-NHC(=O)N(R$_0$)$_2$ and —C$_{1-8}$-aliphatic-NHC(=O)$_{1-2}$R$_0$. Preferred substituted aryls are 2-fluorophenyl, 3-fluorophenyl, 4-fluorophenyl, 2,3-difluorophenyl, 2,4-difluorophenyl, 3,4-difluorophenyl, 2-chlorophenyl, 3-chlorophenyl, 4-chlorophenyl, 2,3-dichlorophenyl, 2,4-dichlorophenyl, 3,4-dichlorophenyl, 2-methoxyphenyl, 3-methoxy-phenyl, 4-methoxy-phenyl, 2,3-dimethoxy-phenyl, 2,4-dimethoxy-phenyl, 3,4-dimethoxy-phenyl, 2-methyl-phenyl, 3-methyl-phenyl, 4-methyl-phenyl, 2,3-dimethyl-phenyl, 2,4-dimethyl-phenyl and 3,4-dimethyl-phenyl.

Heteroaryl preferably stands for a 5-, 6- or 7-membered cyclic aromatic residue that contains 1, 2, 3, 4 or 5 heteroatoms, wherein the heteroatoms, the same or different, are nitrogen, oxygen or sulphur, and the heterocycle can be unsubstituted or mono- or polysubstituted; wherein in the case of the substitution on the heterocycle, the substituents can be the same or different and can be in any desired and possible position of the heteroaryl; and wherein the heterocycle can also be part of a bi- or polycyclic system. "Heteroaryl" is preferably selected from the group comprising pyrrolyl, indolyl, furyl(furanyl), benzofuranyl, thienyl (thiophenyl), benzothienyl, benzothiadiazolyl, benzooxadiazolyl, benzothiazolyl, benzooxazolyl, benzotriazolyl, benzodioxolanyl, benzodioxanyl, phthalazinyl, pyrazolyl, imidazolyl, thiazolyl, oxazolyl, isoxazoyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, wherein the bonding can occur via any desirable and possible ring member of the heteroaryl residue. Where heteroaryl is mono- or polysubstituted, the heteroaryl substituents can be the same or different and can be in any desirable and possible position of the heteroaryl, and are selected independently of one another from the group comprising —F, —Cl, —Br, —I, —CN, —NO$_2$, —CHO, =O, —R$_0$, —C(=O)R$_0$, —C(=O)OH, —C(=O)OR$_0$, —C(=O)—NH$_2$, —C(=O)NHR$_0$, —C(=O)N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O—, —NH—C(=O)R$_0$, —NHC(=O)OR$_0$, —NHC(=O)NH$_2$, —NHC(=O)NHR$_0$, —NHC(=O)N(R$_0$)$_2$, —Si(R$_0$)$_3$, —PO(OR$_0$)$_2$, —C$_{1-8}$-aliphatic-NHC(=O)R$_0$, —C$_{1-8}$-aliphatic-NHC(=O)OR$_0$, —C$_{1-8}$-aliphatic-NHC(=O)NHR$_0$, —C$_{1-8}$-aliphatic-NHC(=O)N(R$_0$)$_2$ and —C$_{1-8}$-aliphatic-NHS(=O)$_{1-2}$R$_0$.

With respect to "aryl" or "heteroaryl", "mono- or polysubstituted" are understood to mean the mono- or polysubstitution, e.g. di-, tri-, 4- or 5-substitution, of one or more hydrogen atoms of the ring system.

Particularly preferred are the substituents or aryl and heteroaryl respectively selected independently of one another from —F, —Cl, —Br, —I, —CN, —CHO, —CO$_2$H, —NH$_2$, —NO$_2$, —NHR$_0$, —N(R$_0$)$_2$, —N$^+$(R$_0$)$_3$, —N$^+$(R$_0$)$_2$O—, —SH, —SR$_0$, —OH, —OR$_0$, —C(=O)R$_0$, —CO$_2$R$_0$, —C(=O)NH$_2$, —C(=O)NHR$_0$, —C(=O)N(R$_0$)$_2$, —S(=O)$_{1-2}$R$_0$, —S(=O)$_2$NH$_2$, —SO$_3$H, =O or —R$_0$. Preferred substituents are —F, —Cl, —Br, —I, —OH, —OC$_{1-6}$-alkyl, —O—C(=O)—C$_{1-6}$-alkyl, —SH, —NH$_2$, —NHC$_{1-6}$-alkyl, —N(C$_{1-6}$-alkyl)$_2$, —C(=O)OC$_{1-6}$-alkyl or —C(=O)OH. Compounds, in which "aryl substituted" or "heteroaryl substituted" means aryl or heteroaryl substituted with —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$, are preferred. Particularly preferred substituents are —F, —Cl, —OH, —SH, —NH$_2$ and —C(=O)OH.

The compounds according to the invention can be present in the form of a single stereoisomer or mixture thereof, the free compounds and/or their physiologically compatible salts and/or solvates.

The compounds according to the invention can be chiral or achiral, depending on the substitution pattern.

Depending on the substitution with respect to the cyclohexane ring the compounds according to the invention can be isomers, in which the substitution pattern in 1,4 position (1 position: >C(NR$_1$R)R$_3$; 4 position: C(hetero)aryl)Q) can also be referred to as syn/anti. "Syn/anti isomers" are a subgroup of the stereoisomers (configuration isomers).

In a preferred embodiment, the diastereomer excess of the syn-isomer amounts to at least 50% de, more preferred at least 75% de, more preferred at least 90% de, most preferred at least 95% de, and in particular at least 99% de. In another preferred embodiment, the diastereomer excess of the anti-isomer amounts to at least 50% de, more preferred at least 75% de, more preferred at least 90% de, most preferred at least 95% de, and in particular at least 99% de.

Suitable methods for separating the isomers (diastereomers) are known to the person skilled in the art. Column chromatography, preparative HPLC and crystallisation processes can be given as examples.

If the compounds according to the invention are chiral, then they are preferably present as racemate or in concentrated form of an enantiomer. In a preferred embodiment the enantiomer excess(ee) of the S-enantiomer amounts at least 50% ee, more preferred at least 75% ee, more preferred at least 90% ee, most preferred at least 95% ee, and in particular at least 99% ee. In another preferred embodiment, the enantiomer excess (ee) of the R-enantiomer amounts to at least 50% ee, more preferred at least 75% ee, more preferred at least 90% ee, most preferred at least 95% ee, and in particular at least 99% ee.

Suitable methods for separating the enantiomers are known to the person skilled in the art. Preparative HPLC on chiral stationary phases and conversion into diastereomeric intermediates can be given as examples. The conversion into diastereomeric intermediates can occur, for example, as salt formation by means of chiral, enantiomer-pure acids. After separation of the diastereomers thus formed, the salt can then be converted into the free base or another salt again.

Unless expressly specified, each reference to the compounds according to the invention covers all isomers (e.g. stereoisomers, diastereomers, enantiomers) in any desired mixture ratio.

Unless expressly specified, each reference to the compounds according to the invention covers the free compounds (i.e. the forms that are not present in the form of salt) and all physiologically compatible salts.

For the purposes of the description, physiologically compatible salts of the compounds according to the invention are present as salts with anions or acids of the respective compound with inorganic or organic acids, which are physiologically compatible—in particular on application in humans and/or mammals.

Examples of physiologically compatible salts of specific acids are salts of: hydrochloric acid, hydrobromic acid, sulphuric acid, methane sulphonic acid, formic acid, acetic acid, oxalic acid, succinic acid, malic acid, tartaric acid, mandelic acid, fumaric acid, lactic acid, citric acid, glutamic acid, saccharinic acid, monomethyl sebacic acid, 5-oxo-proline, hexane-1-sulphonic acid, nicotinic acid, 2-, 3- or 4-aminobenzoic acid, 2,4,6-trimethyl benzoic acid, α-liponic acid, acetylglycine, acetylsalicylic acid, hippuric acid and/or aspartic acid. The hydrochloride, citrate and hemicitrate are particularly preferred.

Physiologically compatible salts with cations or bases are salts of the respective compound—as anion with at least one, preferably inorganic, cation, which are physiologically compatible—in particular on application in humans and/or mammals. Particularly preferred are the salts of the alkali and earth alkali metals, also ammonium salts, but in particular (mono-) or (di-) sodium, (mono-) or (di-) potassium, magnesium or calcium salts.

Respectively preferred embodiments of the compounds according to the invention are explained below. Unless expressly specified, all definitions of the respective substituents explained previously (i.e. from $R_0$ to $R_4$, $Y_1$ to $Y_4'$, Q etc., for example) and their respective embodiments apply accordingly and will not therefore be repeated.

Preferred embodiments of the compounds according to the invention of the general formula (1) have the general formula (2)

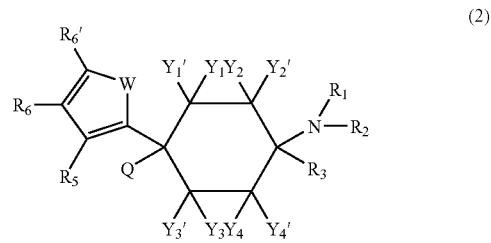

(2)

wherein

W stands for —O—, —S—, —$NR_{11}$—, —$CR_{12}$=$CR_{13}$—, —$CR_{12}$=N— or —N=$CR_{13}$—; preferably for —O—, —S—, or —$NR_{11}$—; particularly preferred for —$NR_{11}$—;

$R_5$, $R_6$, $R_6'$, $R_{11}$, $R_{12}$ and $R_{13}$, respectively independently of one another, stand for —H, —F, —Cl, —Br, —I, —CN, —$NO_2$, —CHO, —$R_0$, —C(=O)$R_0$, —C(=O)H, —C(=O)OH, —C(=O)O$R_0$, —C(=O)$NH_2$, —C(=O)$NHR_0$, —C(=O)—N($R_0$)$_2$, —OH, —O($CH_2$)$_{1-2}$O⁻, —O$R_0$, —OC(=O)H, —OC(=O)$R_0$, —OC(=O)O$R_0$, —OC(=O)$NHR_0$, —OC(=O)N($R_0$)$_2$, —SH, —S$R_0$, —$SO_3$H, —S(=O)$_{1-2}$—$R_0$, —S(=O)$_{1-2}$$NH_2$, —$NH_2$, —$NHR_0$, —N($R_0$)$_2$, —N⁺($R_0$)$_3$, —N⁺($R_0$)$_2$O⁻, —NHC(=O)$R_0$, —NHC(=O)O$R_0$, —NH—C(=O)$NH_2$, —NHC(=O)$NHR_0$, —NHC(=O)N($R_0$)$_2$, —$C_{1-8}$-aliphatic-NHC(=O)$R_0$, —$C_{1-8}$-aliphatic-NHC(=O)O$R_0$, —$C_{1-8}$-aliphatic-NHC(=O)$NHR_0$, —$C_{1-8}$-aliphatic-NHC(=O)N($R_0$)$_2$ or —$C_{1-8}$aliphatic-NHS(=O)$_{1-2}$$R_0$; or $R_5$ and $R_6$, or $R_6$ and $R_6'$, or $R_6'$ and $R_{12}$ together form a five- or six-membered, saturated, partially unsaturated or aromatic, unsubstituted or mono- or polysubstituted ring, which possibly comprises one or two hetero ring atoms selected independently of one another from N, S and O.

If, for example, W stands for $CR_{12}$=$CR_{13}$—, —$CR_{12}$=N— or —N=$CR_{13}$—, then the following functional groups preferably result:

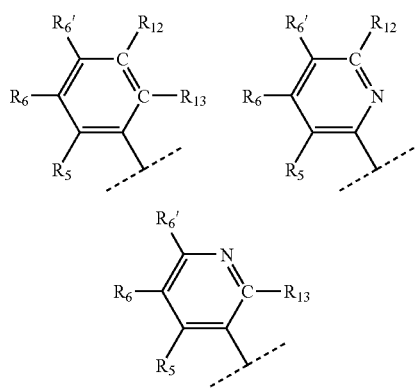

If, for example, $R_6$ and $R_6'$ together form a six-membered aromatic ring, which has no hetero ring atoms, then the respective following functional groups result:

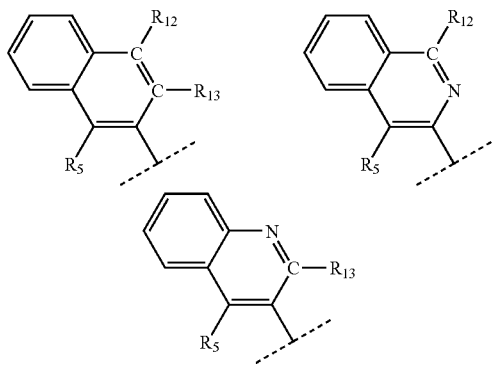

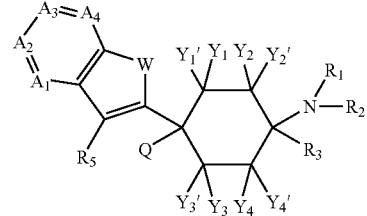

(2.1)

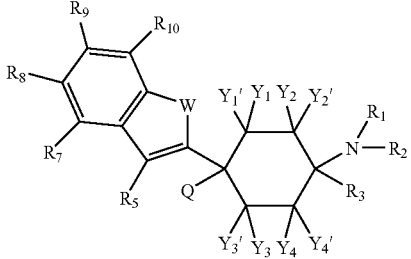

(2.2)

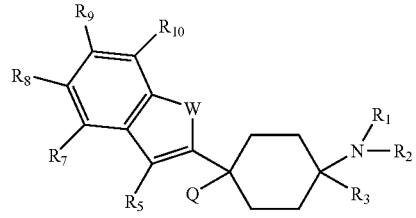

(2.3)

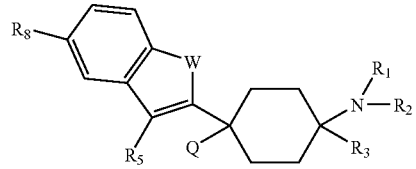

(2.4)

The five- or six-membered, saturated, partially unsaturated or aromatic ring possibly formed by $R_5$ and $R_6$, or $R_6$ and $R_6'$, or $R_6'$ and $R_{12}$ together can comprise one or two hetero ring atoms, which are selected independently of one another from N, S and O. Moreover, this formed ring can be unsubstituted or mono- or polysubstituted, wherein the substituents are preferably selected independently of one another from the group comprising —F, —Cl, —Br, —I, —CN, —NO$_2$, —CHO, —R$_0$, —C(=O)R$_0$, —C(=O)H, —C(=O)OH, —C(=O)OR$_0$, —C(=O)NH$_2$, —C(=O)NHR$_0$, —C(=O)—N(R$_0$)$_2$, —OH, —O(CH$_2$)$_{1-2}$O$^-$, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O—, —NHC(=O)R$_0$, —NHC(=O)OR$_0$, —NH—C(=O)NH$_2$, —NHC(=O)NHR$_0$, —NHC(=O)N(R$_0$)$_2$, —C$_{1-8}$-aliphatic-NHC(=O)R$_0$, —C$_{1-8}$-aliphatic-NHC(=O)OR$_0$, —C$_{1-8}$-aliphatic-NHC(=O)NHR$_0$, —C$_{1-8}$-aliphatic-NHC(=O)N(R$_0$)$_2$ and —C$_{1-8}$-aliphatic-NHS(=O)$_{1-2}$R$_0$; more preferred —F, —Cl, —Br, —I, —CF$_3$, —CN and —NO$_2$.

$R_5$ preferably stands for —H, —F, —Cl or —R$_0$; more preferred for —H, —F, —C$_{1-8}$-aliphatic, —C$_{1-8}$-aliphatic-aryl or —C$_{1-8}$-aliphatic-heteroaryl.

$R_6$ and $R_6'$ preferably together form a six-membered, saturated, partially saturated or aromatic ring, which possibly comprises one or two hetero ring atoms, which are selected independently of one another from N, S and O. This formed ring can be unsubstituted or mono- or polysubstituted, wherein the substituents are preferably selected independently of one another from the group comprising —F, —Cl, —Br, —I, —CN, —NO$_2$, —CHO, —R$_0$, —C(=O)R$_0$, —C(=O)H, —C(=O)OH, —C(=O)OR$_0$, —C(=O)NH$_2$, —C(=O)NHR$_0$, —C(=O)—N(R$_0$)$_2$, —OH, —O(CH$_2$)$_{1-2}$O$^-$, —OR$_0$, —OC(=O)H, —OC(=O)R$_0$, —OC(=O)OR$_0$, —OC(=O)NHR$_0$, —OC(=O)—N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O—, —NHC(=O)R$_0$, —NHC(=O)OR$_0$, —NH—C(=O)NH$_2$, —NHC(=O)NHR$_0$ and —NHC(=O)N(R$_0$)$_2$; more preferred —F, —Cl, —Br, —I, —CF$_3$, —CN and —NO$_2$.

$R_{11}$, $R_{12}$ and $R_{13}$ are preferably selected independently of one another from the group comprising —H, —F, —Cl, —CN, —OH, —Ro and —OR$_0$. It is particularly preferred if $R_{11}$, $R_{12}$ and $R_{13}$—where present—respectively are —H.

Preferred embodiments of the compounds according to the invention of the general formula (2) have the general formula (2.1), (2.2), (2.3) or (2.4):

wherein $A_1$ stands for —N= or —CR$_7$=, $A_2$ stands for —N= or —CR$_8$=, $A_3$ stands for —N= or —CR$_9$=, $A_4$ stands for —N= or —CR$_{10}$=;

on condition that at most one of the residues $A_1$, $A_2$, $A_3$ and $A_4$, preferably 0, 1 or 2 of the residues $A_1$, $A_2$, $A_3$ and $A_4$, stand for —N=;

$R_7$, $R_8$, $R_9$ and $R_{10}$, respectively independently of one another stand for —H, —F, —Cl, —Br, —I, —NO$_2$, —CF$_3$, —OR$_{23}$, —SR$_{23}$, —SO$_2$R$_{23}$, —CN, —COOR$_{23}$, —CONR$_{23}$, —NR$_{24}$R$_{25}$, =O or —Ro; preferably for —F, —Cl, —Br, —I, —CF$_3$, —CN or —NO$_2$;

$R_{23}$ respectively independently stands for —H or —R$_0$;

$R_{24}$ and $R_{25}$ independently of one another stand for —H or —R$_0$; or $R_{24}$ and $R_{25}$ together stand for —CH$_2$CH$_2$OCH$_2$CH$_2$—, —CH$_2$CH$_2$NR$_{26}$CH$_2$CH$_2$— or —(CH$_2$)$_{3-6}$—;

$R_{26}$ stands for —H or —C$_{1-6}$-aliphatic.

Further preferred embodiments of the compounds according to the invention of the general formula (1) have the general formula (3)

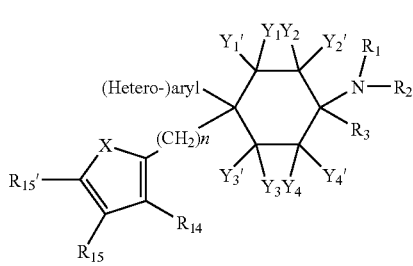

(3)

wherein
X stands for —O—, —S—, —$NR_{16}$—, —$CR_{17}$=$CR_{18}$—, —$CR_{17}$=N— or —N=$CR_{18}$—; preferably for —O—, —S—, —$NR_{16}$— or —$CR_{17}$=$CR_{18}$—;
$R_{14}$, $R_{15}$, $R_{15}'$, $R_{16}$, $R_{17}$ and $R_{18}$ respectively independently of one another stand for —H, —F, —Cl, —Br, —I, —CN, —$NO_2$, —CHO, —$R_0$, —C(=O)$R_0$, —C(=O)H, —C(=O)OH, —C(=O)$OR_0$, —C(=O)$NH_2$, —C(=O)$NHR_0$, —C(=O)—N($R_0$)$_2$, —OH, —O($CH_2$)$_{1-2}$$O^-$, —$OR_0$, —OC(=O)H, —OC(=O)$R_0$, —OC(=O)$OR_0$, —OC(=O)$NHR_0$, —OC(=O)N($R_0$)$_2$, —SH, —$SR_0$, —$SO_3$H, —S(=O)$_{1-2}$—$R_0$, —S(=O)$_{1-2}$$NH_2$, —$NH_2$, —$NHR_0$, —N($R_0$)$_2$, —$N^+$($R_0$)$_3$, —$N^+$($R_0$)$_2$$O^-$, —NHC(=O)$R_0$, —NHC(=O)$OR_0$, —NH—C(=O)$NH_2$, —NHC(=O)$NHR_0$, —NHC(=O)N($R_0$)$_2$, —$C_{1-8}$-aliphatic-NHC(=O)$R_0$, —$C_{1-8}$-aliphatic-NHC(=O)$OR_0$, —$C_{1-8}$-aliphatic-NHC(=O)$NHR_0$, —$C_{1-8}$-aliphatic-NHC(=O)N($R_0$)$_2$ or —$C_{1-8}$-aliphatic-NHS(=O)$_{1-2}$$R_0$; or $R_{14}$ and $R_{15}$, or $R_{15}$ and $R_{15}'$, or $R_{15}'$ and $R_{17}$ together form a five- or six-membered, saturated, partially unsaturated or aromatic, unsubstituted or mono- or polysubstituted ring, which possibly comprises one or two hetero ring atoms selected independently of one another from N, S and O; and
n stands for 0, 1 or 2; preferably for 0 or 1; more preferred for 0 (if n stands for 0, then a bond results).

If n stands for 2, for example, and X stands for —$CR_{17}$=$CR_{18}$—, —$CR_{17}$=N— or —N=$CR_{18}$—, for example, then the following functional groups preferably result:

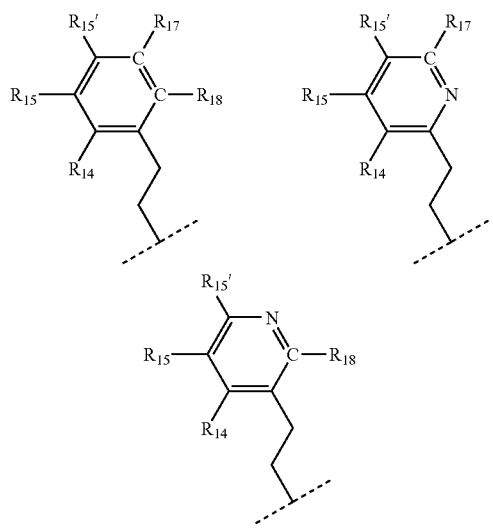

If, for example, $R_{15}$ and $R_{15}'$ together form a six-membered aromatic ring, which does not have any hetero ring atoms, then the respective following functional groups result:

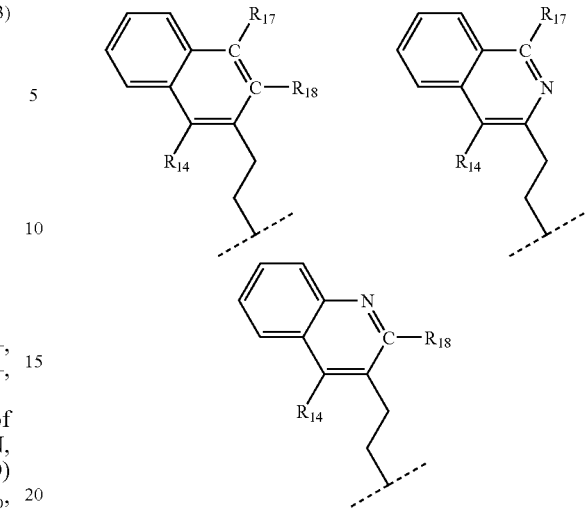

The five- or six-membered, saturated, partially unsaturated or aromatic ring possibly formed by $R_{14}$ and $R_{15}$, or $R_{15}$ and $R_{15}'$, or $R_{15}'$ and $R_{17}$ together can comprise one or two hetero ring atoms, which are selected independently of one another from N, S and O. Moreover, this formed ring can be unsubstituted or mono- or polysubstituted, wherein the substituents are preferably selected independently of one another from the group comprising —F, —Cl, —Br, —I, —CN, —$NO_2$, —CHO, —$R_0$, —C(=O)$R_0$, —C(=O)H, —C(=O)OH, —C(=O)$OR_0$, —C(=O)$NH_2$, —C(=O)$NHR_0$, —C(=O)—N($R_0$)$_2$, —OH, —O($CH_2$)$_{1-2}$$O^-$, —$OR_0$, —OC(=O)H, —OC(=O)$R_0$, —OC(=O)$OR_0$, —OC(=O)NHR_0$, —OC(=O)N($R_0$)$_2$, —SH, —$SR_0$, —$SO_3$H, —S(=O)$_{1-2}$—$R_0$, —S(=O)$_{1-2}$$NH_2$, —$NH_2$, —$NHR_0$, —N($R_0$)$_2$, —$N^+$($R_0$)$_3$, —$N^+$($R_0$)$_2$$O^-$, —NHC(=O)$R_0$, —NHC(=O)$OR_0$, —NH—C(=O)$NH_2$, —NHC(=O)$NHR_0$, —NHC(=O)N($R_0$)$_2$, —$C_{1-8}$-aliphatic-NHC(=O)$R_0$, —$C_{1-8}$-aliphatic-NHC(=O)$OR_0$, —$C_{1-8}$-aliphatic-NHC(=O)$NHR_0$, —$C_{1-8}$-aliphatic-NHC(=O)N($R_0$)$_2$ and —$C_{1-8}$-aliphatic-NHS(=O)$_{1-2}$$R_0$; more preferred —F, —Cl, —Br, —I, —$CF_3$, —CN and —$NO_2$.

$R_{14}$ preferably stands for —H, —F, —Cl or —$R_0$; more preferred for —H, —F, —$C_{1-8}$-aliphatic, —$C_{1-8}$-aliphatic-aryl or —$C_{1-8}$-aliphatic-heteroaryl.

$R_{15}$ and $R_{15}'$ preferably together form a six-membered, saturated, partially unsaturated or aromatic ring, which can possibly comprise one or two hetero ring atoms that are selected independently of one another from N, S and O. This formed ring can be unsubstituted or mono- or polysubstituted, wherein the substituents are preferably selected independently of one another from the group comprising —F, —Cl, —Br, —I, —CN, —$NO_2$, —CHO, —$R_0$, —C(=O)$R_0$, —C(=O)H, —C(=O)OH, —C(=O)$OR_0$, —C(=O)$NH_2$, —C(=O)$NHR_0$, —C(=O)—N($R_0$)$_2$, —OH, —O($CH_2$)$_{1-2}$$O^-$, —$OR_0$, —OC(=O)H, —OC(=O)$R_0$, —OC(=O)$OR_0$, —OC(=O)$NHR_0$, —OC(=O)—N($R_0$)$_2$, —SH, —$SR_0$, —$SO_3$H, —S(=O)$_{1-2}$—$R_0$, —S(=O)$_{1-2}$$NH_2$, —$NH_2$, —$NHR_0$, —N($R_0$)$_2$, —$N^+$($R_0$)$_3$, —$N^+$($R_0$)$_2$$O^-$, —NHC(=O)$R_0$, —NHC(=O)$OR_0$, —NH—C(=O)$NH_2$, —NHC(=O)$NHR_0$ and —NHC(=O)N($R_0$)$_2$; more preferred —F, —Cl, —Br, —I, —$CF_3$, —CN and —$NO_2$.

$R_{16}$, $R_{17}$ and $R_{18}$ are preferably selected independently of one another from the group comprising —H, —F, —Cl, —CN, —OH, —$R_0$ and —$OR_0$. It is particularly preferred if $R_{16}$, $R_{17}$ and $R_{18}$—where present—are respectively —H.

Preferred embodiments of the compounds according to the invention of the general formula (3) have the general formula (3.1) or (3.2):

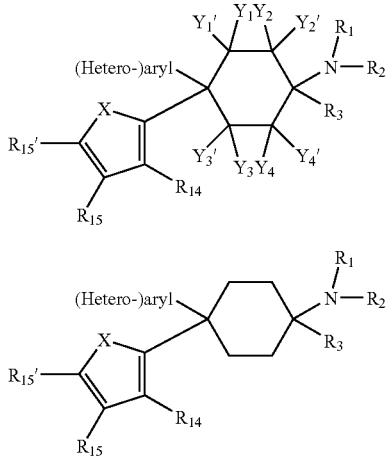

Particularly preferred embodiments of the compounds according to the invention of the general formulae (3.1) and (3.2) have the general formula (3.1.1), (3.1.2), (3.1.3), (3.2.1), (3.2.2) or (3.2.3):

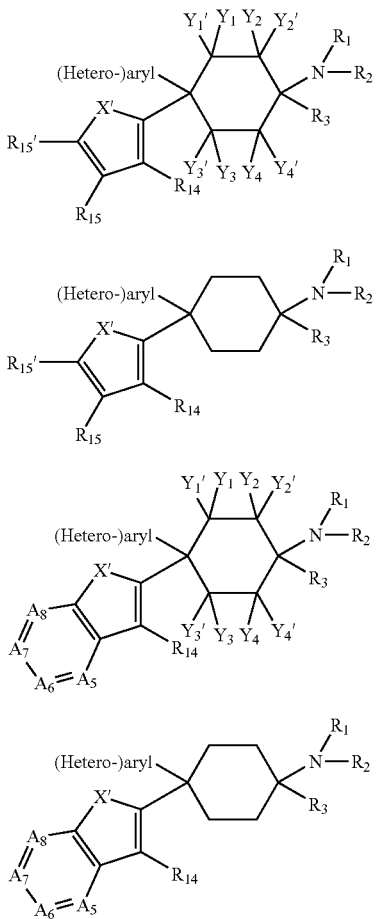

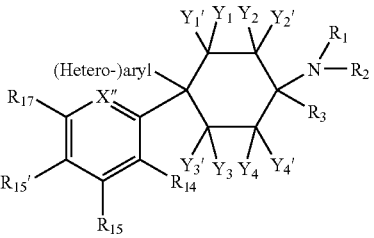

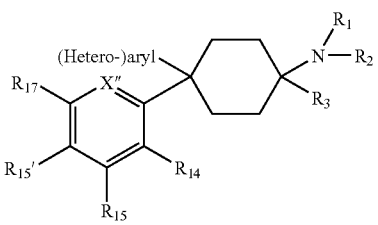

wherein
X' stands for —$NR_{16}$—, —O—, or —S—; preferably for —$NR_{16}$—; and
X'' stands for —N= or —$CR_{18}$=; preferably for —$CR_{18}$—; and
$A_5$ stands for —N= or —$CR_{19}$;
$A_6$ stands for —N= or —$CR_{20}$;
$A_7$ stands for —N= or —$CR_{21}$;
$A_8$ stands for —N= or —$CR_{22}$;
on the condition that at most two of the residues $A_5$, $A_6$, $A_7$ and $A_8$, preferably 0, 1 or 2 of the residues $A_5$, $A_6$, $A_7$ and $A_8$, are —N=.
$R_{19}$, $R_{20}$, $R_{21}$ and $R_{22}$ respectively independently of one another stand for —H, —F, —Cl, —Br, —I, —$NO_2$, —$CF_3$, —$OR_{27}$, —$SR_{27}$, —$SO_2R_{27}$, —CN, —$COOR_{27}$, —$CONR_{27}$, —$NR_{28}R_{29}$, =O or —$R_0$; preferably for —F, —Cl, —Br, —I, —$CF_3$, —CN or —$NO_2$;
$R_{27}$ respectively independently stands for —H or —$R_0$;
$R_{28}$ and $R_{29}$ independently of one another stand for —H or —$R_0$; or $R_{14}$ and $R_{15}$ together stand for —$CH_2CH_2OCH_2CH_2$—, —$CH_2CH_2NR_3OCH_2CH_2$— or —$(CH_2)_{3-6}$—;
$R_{30}$ stands for —H or —$C_{1-6}$-aliphatic.

Particularly preferred embodiments of the compounds according to the invention of the general formulae (1), (2) and (3) have the general formula (4):

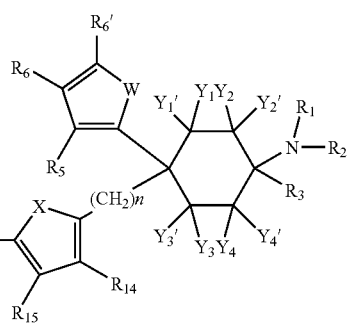

Preferred embodiments of the compounds according to the invention of the general formula (4) have the general formula (4.1), (4.2), (4.3), (4.4), (4.5), (4.6), (4.7) or (4.8):

(4.1) 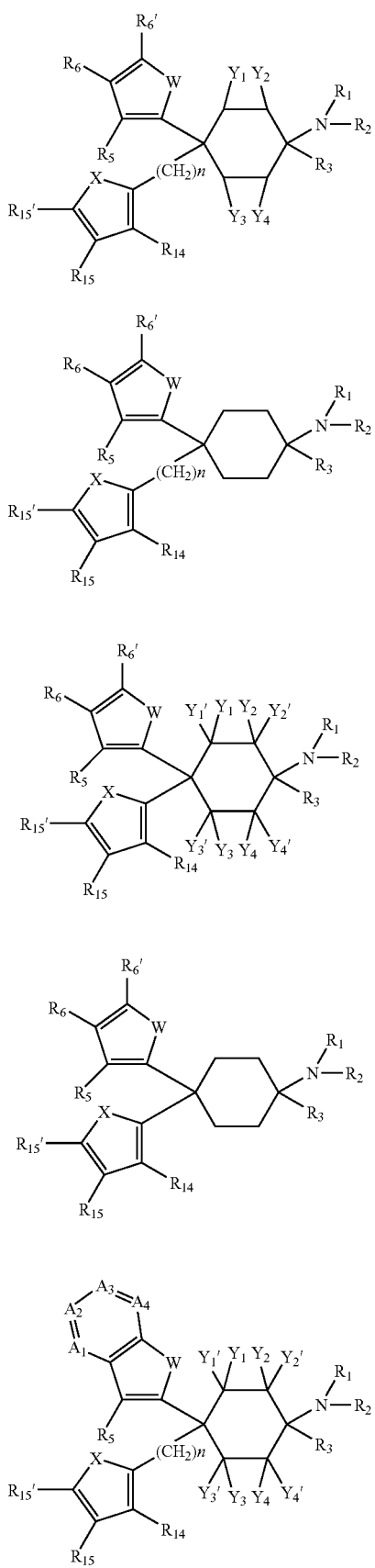
(4.2)
(4.3)
(4.4)
(4.5)
(4.6) 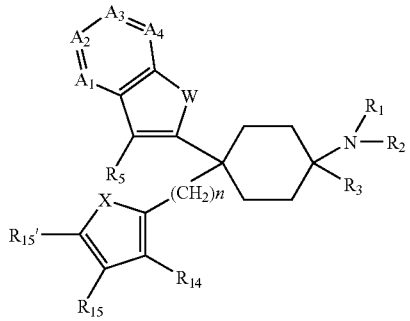
(4.7)
(4.8)
Further embodiments of the compounds according to the invention of the general formula (1) have the general formula (5)
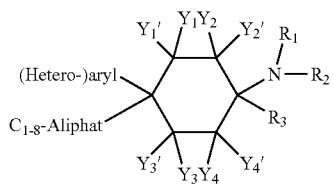
(5)
[Aliphat = aliphatic]
wherein all substituents have the above-defined meaning. —$C_{1-8}$-aliphatic is preferably —$C_{1-8}$-alkyl.
Preferred embodiments of the compounds of the general formula (5) have the general formula (5.1), (5.2), (5.3), (5.4), (5.5) or (5.6):

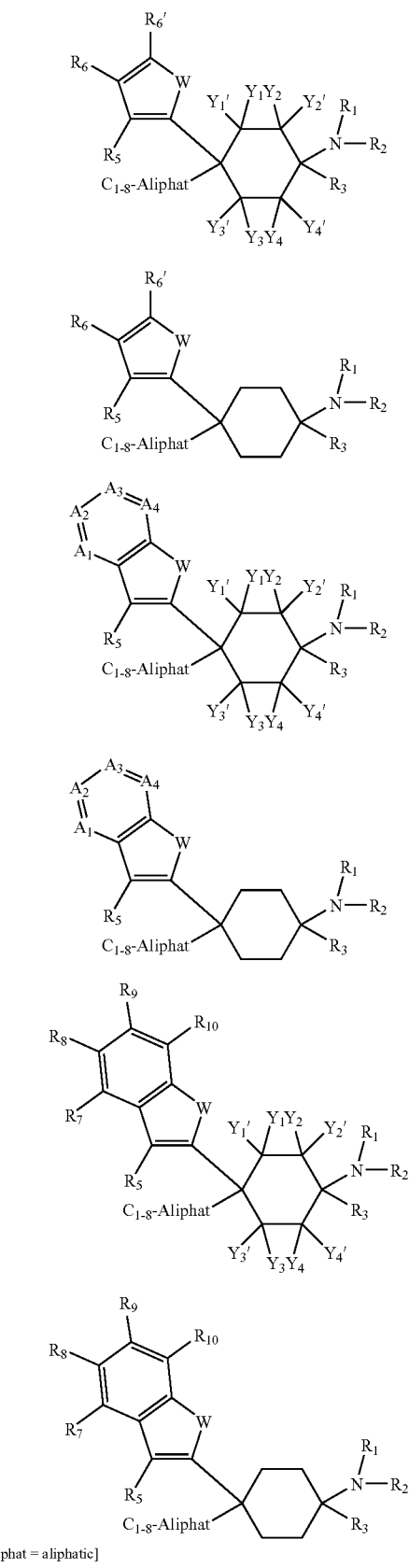

[Aliphat = aliphatic]

The compounds according to the invention are defined by substituents, e.g. by $R_1$, $R_2$ and $R_3$ (substituents of the first generation), which are themselves possibly substituted (substituents of the second generation). Depending on the definition, these substituents of the substituents can themselves be substituted again (substituents of the third generation). If, for example, $Y_1$=—$R_0$, wherein —$R_0$=—$C_{1-8}$-aliphatic (substituent of the first generation), then —$C_{1-8}$-aliphatic can itself be substituted, e.g. with —$OR_0$, wherein $R_0$=-aryl (substituent of the second generation). This gives the functional group —$C_{1-8}$-aliphatic-Oaryl. -Aryl can then in turn be substituted again, e.g. with —Cl (substituent of the third generation). This then gives overall the functional group —$C_{1-8}$-aliphatic-Oaryl-Cl.

In a preferred embodiment, the substituents of the third generation cannot be substituted again, i.e. there are then no substituents of the fourth generation.

In another preferred embodiment, the substituents of the second generation cannot be substituted again, i.e. there are then already no substituents of the third generation. In other words, in this embodiment the functional groups for $R_0$ to $R_{30}$ can possibly be respectively substituted, but the respective substituents cannot then themselves be substituted again.

In another preferred embodiment, the substituents of the first generation cannot be substituted again, i.e. there are then neither substituents of the second generation nor substituents of the third generation. In other words, in this embodiment the functional groups for $R_0$ to $R_{30}$ are not respectively substituted.

Embodiments of the compounds of the general formula (4.8) particularly preferred according to the invention are compounds of the general formula (4.8.1)

(4.8.1)

wherein
W stands for —O— or —$NR_{11}$—;
X stands for —O—, —$NR_{16}$— or —$CR_{17}$=$CR_{18}$—;
n stands for 0 or 1;
$R_1$ stands for —$CH_3$;
$R_2$ stands for —H or —$CH_3$; or
$R_1$ and $R_2$ jointly form a ring and stand for —$(CH_2)_{3-4}$—;
$R_3$ stands for —$C_{1-8}$-aliphatic, -aryl or heteroaryl; preferably —$C_{1-8}$-alkyl, -phenyl, thienyl, furfyl or pyrrolyl; wherein these are unsubstituted or mono- or polysubstituted, preferably with substituents selected independently of one another from the group comprising —F, —Cl, —Br, —CN, —$CH_3$, —$C_2H_5$, —$NH_2$, —$NO_2$, —SH, —$CF_3$, —OH, —$OCH_3$, —$OC_2H_5$ and —$N(CH_3)_2$;
$R_5$ and $R_{14}$ independently of one another stand for —H, —F, —$C_{1\text{-}8}$-aliphatic, —$C_{1\text{-}8}$-aliphatic-aryl, —$C_{1\text{-}8}$-aliphatic-heteroaryl, —$C_{1\text{-}8}$-aliphatic-NHC(=O)$R_0$, —$C_{1\text{-}8}$-aliphatic-NHC(=O)OR$_0$, —C$_{1-8}$-aliphatic-NHC(=O)NHR$_0$, —C$_{1-8}$-aliphatic-NHC(=O)N(R$_0$)$_2$ or —C$_{1-8}$-aliphatic-NHS(=O)$_{1-2}$R$_0$;

R$_8$ stands for —F, —Cl, —Br, —I, —CF$_3$, —CN or —NO$_2$;

R$_{11}$ stands for —H;

R$_{14}$, R$_{15}$ and R$_{15}$' independently of one another stand for —H, —F, —Cl, —Br, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$; or R$_{15}$ and R$_{15}$' jointly form a six-membered, saturated, partially unsaturated or aromatic ring, which can possibly comprise one or two hetero ring atoms, which are selected independently of one another from N, S and O; wherein this formed ring can be unsubstituted or mono- or polysubstituted, wherein the substituents are selected independently of one another from the group comprising —F, —Cl, —Br, —I, —CF$_3$, —CN and —NO$_2$.

R$_{16}$ stands for —H; and

R$_{17}$ and R$_{18}$ independently of one another stand for —H or —F.

Most particularly preferred are compounds from the group:

1-butyl-N,N-dimethyl-4,4-bis(3-methyl-5-(trifluoromethyl)-1H-indol-2-yl)cyclohexanamine; 2-hydroxypropane-1,2,3-tricarboxylate;

1-butyl-4,4-bis(5-fluoro-3-methyl-1H-indol-2-yl)-N,N-dimethylcyclohexanamine;

1-benzyl-N,N-dimethyl-4,4-bis(3-(2-(pyridin-4-yl)ethyl)-1H-indol-2-yl)cyclohexanamine; 2-hydroxypropane-1,2,3-tricarboxylate;

N,N-dimethyl-4,4-bis(3-(2-(pyridin-4-yl)ethyl)-1H-indol-2-yl)-1-(thiophen-2-yl)-cyclohexanamine;

2,2'-(4-butyl-4-(pyrrolidin-1-yl)cyclohexane-1,1-diyl)bis(3-(2-(pyridin-4-yl)ethyl)-1H-indole);

N-methyl-1-phenyl-4,4-bis(3-(2-(pyridin-4-yl)ethyl)-1H-indol-2-yl)cyclohexanamine;

N,N-dimethyl-4-(3-methyl-1H-indol-2-yl)-1-phenyl-4-(thiophen-2-yl)cyclohexanamine; 2-hydroxypropane-1,2,3-tricarboxylate;

N,N-dimethyl-4-(3-methyl-1H-indol-2-yl)-1-phenyl-4-(thiophen-2-yl)cyclohexanamine;

N,N-dimethyl-4-(3-methyl-1H-indol-2-yl)-1,4-diphenylcyclohexanamine; 2-hydroxypropane-1,2,3-tricarboxylate;

N,N-dimethyl-4,4-bis(3-methylbenzofuran-2-yl)-1-phenylcyclohexanamine; 2-hydroxypropane-1,2,3-tricarboxylate;

N,N-dimethyl-4,4-bis(3-methyl-1H-indol-2-yl)-1-phenylcyclohexanamine; 2-hydroxypropane-1,2,3-tricarboxylate;

1-butyl-N,N-dimethyl-4,4-bis(3-(2-(pyridin-4-yl)ethyl)-1H-indol-2-yl)-cyclohexanamine; 2-hydroxypropane-1,2,3-tricarboxylate;

N,N,4-trimethyl-4-(3-methyl-1H-indol-2-yl)-1-phenylcyclohexanamine;

4-benzyl-N,N-dimethyl-4-(3-methyl-1H-indol-2-yl)-1-phenylcyclohexanamine;

dimethyl 2,2'-(2,2'-(4-butyl-4-(dimethylamino)cyclohexan-1,1-diyl)bis(1H-indol-3,2-diyl))diacetate;

2,2'-(2,2'-(4-butyl-4-(dimethylamino)cyclohexan-1,1-diyl)bis(1H-indol-3,2-diyl))diethanol;

1-butyl-N,N-dimethyl-4-(3-methyl-1H-indol-2-yl)-4-(3-(2-pyridin-4-yl)ethyl)-1H-indol-2-yl)cyclohexylamine;

1-butyl-4,4-bis-(3-(2-(3,4-dihydro-1H-isoquinolin-2-yl)ethyl)-1H-indol-2-yl)-N,N-dimethylcyclohexylamine;

4-(4-methoxyphenyl)-N,N-dimethyl-4-(3-methyl-1H-indol-2-yl)-1-phenylcyclohexylamine;

1-butyl-N,N-dimethyl-4,4-bis-(3-methyl-1H-indol-2-yl)cyclohexylamine;

2-(2-(2-(4-butyl-4-dimethylamino-1-(3-methyl-1H-indol-2-yl)cyclohexyl)-1H-indol-3-yl)ethyl)isoindolin-1,3-dione 2-[2-[2-[4-butyl-4-dimethylamino-1-[3-[2-(1,3-dioxo-2H-isoindol-2-yl)-ethyl]-1H-indol-2-yl]-cyclohexyl]-1H-indol-3-yl]-ethyl]-2H-isoindole-1,3-dione;

4-(benzo[d][1,3]dioxol-5-yl)-N,N-dimethyl-4-(3-methyl-1H-indol-2-yl)-1-phenylcyclohexylamine;

dimethyl 3,3'-(2-(4-butyl-4-(dimethylamino)cyclohexan-1,1-diyl)bis(1H-indol-2,3-diyl)dipropanate;

4-(3-(2-aminoethyl)-1H-indol-2-yl)-1-butyl-N,N-dimethyl-4-(3-methyl-1H-indol-2-yl)cyclohexylamine;

1-(3-fluorophenyl)-N,N-dimethyl-4-(3-methyl-1H-indol-2-yl)-4-thiophen-2-ylcyclohexylamine;

1-butyl-4,4-bis-(1,3-dimethyl-1H-indol-2-yl)-N,N-dimethylcyclohexylamine;

1-butyl-4-(1,3-dimethyl-1H-indol-2-yl)-N,N-dimethyl-4-(3-methyl-1H-indol-2-yl)cyclohexylamine;

1-benzyl-N,N-dimethyl-4-(3-methyl-1H-indol-2-yl)-4-(thiophen-2-yl)cyclohexylamine;

4-(3-methoxyphenyl)-N,N-dimethyl-4-(3-methyl-1H-indol-2-yl)-1-phenylcyclohexylamine;

N-(2-(2-(4-butyl-4-(dimethylamino)-1-(3-methyl-1H-indol-2-yl)cyclohexyl)-1H-indol-3-yl)ethyl)cyclopentane sulphonamide;

1-(3-fluorophenyl)-N,N-dimethyl-4-(3-methyl-1H-indol-2-yl)-4-thiophen-2-ylcyclohexylamine;

N,N-dimethyl-1-phenyl-4,4-bis-(3-(2-pyridin-4-yl)ethyl)-1H-indol-2-yl)cyclohexylamine;

1-(2-(2-(4-butyl-4-(dimethylamino)-1-(3-methyl-1H-indol-2-yl)cyclohexyl)-1H-indol-3-yl)ethyl)-3-phenylurea;

1,1'-(2,2'-(2,2'-(4-butyl-4(dimethylamino)cyclohexan-1,1-diyl)bis(1H-indol-3,2-diyl))bis(ethan-2,1-diyl)bis(3-phenylurea);

1-butyl-4,4-bis(5-fluoro-3-methyl-1H-indol-2-yl)-N,N-dimethylcyclohexylamine;

4-(3-(2-aminoethyl)-1H-indol-2-yl)-1-butyl-4-(5-fluoro-3-methyl-1H-indol-2-yl)-N,N-cyclohexylamine;

(phenyl-2-(2-(4-butyl-4-(dimethylamino)-1-(5-fluoro-3-methyl-1H-indol-2-yl)cyclohexyl)-1H-indol-3-yl)ethyl carbamate;

1-(2-(2-(4-butyl-4-(dimethylamino)-1-(5-fluoro-3-methyl-1H-indol-2-yl)cyclohexyl)-1H-indol-3-yl)ethyl)-3-phenylurea;

N,N-dimethyl-4-(3-methyl-1H-indol-2-yl)-1-phenyl-4-(3-(2-pyridin-4-yl)ethyl)-1H-indol-2-yl)cyclohexylamine;

N,N-dimethyl-1-phenyl-4-(3-(2-(pyridin-4-yl)-ethyl)-1H-indol-2-yl)-4-(thiophen-2-yl)-cyclohexylamine and physiologically compatible salts and/or solvates thereof.

The compounds according to the invention act, for example, on the relevant ORL 1-receptor in association with different diseases, and therefore they are suitable as pharmaceutical active substance in a medication.

Therefore, the invention additionally relates to medications, which contain at least one compound according to the invention, as well as possibly suitable additives and/or adjuvants and/or possibly further active substances.

The compounds according to the invention have an affinity to the µ-opioid or to the ORL 1-receptor comparable to the compounds disclosed as exemplary compounds in WO 2004043967. However, compared to these compounds they exhibit a higher selectivity with respect to the kappa-opioid receptor, which is responsible for side-effects such as e.g. dysphoria, sedation and diuresis. In addition, with a favourable ORL 1/µ affinity the compounds according to the invention exhibit a balanced affinity to the µ-opioid receptor that is not too strong. This is an advantage, since the µ-opioid receptor is associated with side-effects, in particular respiratory depression, constipation and addiction dependence. Therefore, they are particularly suitable for drug development.

Besides at least one compound according to the invention, the medications according to the invention possibly contain suitable additives and/or adjuvants, hence also support materials, fillers, solvents, diluants, colouring agents and/or binders, and can be administered as liquid medications in the form of injectable solutions, drops or juices, as semisolid medications in the form of granules, tablets, pellets, patches, capsules, plasters/spray plasters or aerosols. The selection of adjuvants etc. as well as the quantities thereof to be used are dependent on whether the medication is to be applied orally, perorally, parenterally, intravenously, intraperitoneally, intradermally, intramuscularly, intranasally, bucally, rectally or locally, e.g. onto the skin, mucous membranes or into the eyes. Preparations in the form of tablets, coated tablets, capsules, granules, drops, juices and syrups are suitable for oral application, solutions, suspensions, readily reconstituted dry preparations as well as sprays are suitable for parenteral, topical and inhalatory application. Compounds according to the invention in a depot, in dissolved form or in a plaster, possibly with the addition of skin-penetration promoters, are suitable preparations for percutaneous application. Preparation forms that may be applied orally or percutaneously can release the compounds according to the invention in a delayed manner. The compounds according to the invention can also be applied in parenteral long-term depot forms such as e.g. implants or implanted pumps. In principle, other additional active substances known to the skilled person can be added to the medications according to the invention.

The amount of active substance to be administered to the patient varies depending on the weight of the patient, on the type of application, the indication and the degree of severity of the disease. Usually, 0.00005 to 50 mg/kg, preferably 0.001 to 0.5 mg/kg, of at least one compound according to the invention are applied.

For all the above-mentioned forms of the medication according to the invention it is particularly preferred if, besides at least one compound according to the invention, the medication also contains a further active substance, in particular an opioid, preferably a strong opioid, in particular morphine, or an anaesthetic, preferably hexobarbital or halothane.

In a preferred form of the medication, a contained compound according to the invention is present in the form of pure diastereomer and/or enantiomer.

The ORL 1-receptor was identified in particular in the pain process. Compounds according to the invention can be used accordingly for the production of a medication for the treatment of pain, in particular of acute, neuropathic or chronic pain.

Therefore, the invention additionally relates to the use of a compound according to the invention for the production of a medication for the treatment of pain, in particular of acute, visceral, neuropathic or chronic pain.

The invention further relates to the use of a compound according to the invention for the treatment of anxiety conditions, stress and stress-related syndromes, depressive illnesses, epilepsy, Alzheimer's disease, senile dementia, general cognitive dysfunctions, learning and memory disabilities (as nootropic), withdrawal symptoms, alcohol and/or drug and/or medication misuse and/or dependence, sexual dysfunctions, cardiovascular diseases, hypotension, hypertension, tinitus, pruritus, migraine, hearing impairment, deficient intestinal motility, eating disorders, anorexia, bulimia, mobility disorders, diarrhoea, cachexia, urinary incontinence, or as muscle relaxant, anticonvulsive or anaesthetic, or for coadministration in the treatment with an opioid analgesic or with an anaesthetic, for diuresis or anti-natriuresis, anxiolysis, for modulating movement activity, for modulating neurotransmitter release and for treating neuro-degenerative diseases associated therewith, for treating withdrawal symptoms and/or for reducing the addiction potential of opioids.

In this case, it can be preferred in one of the above uses if a used compound is present as a pure diastereomer and/or enantiomer, as a racemate or as non-equimolar or equimolar mixture of the diastereomers and/or enantiomers.

The invention additionally relates to a method for treating, in particular in one of the aforementioned indications, a non-human mammal or human, which or who requires a treatment for pain, in particular chronic pain, by the administration of a therapeutically effective dose of a compound according to the invention or a medication according to the invention.

The invention further relates to a method for producing the compounds according to the invention as outlined in the following description and examples.

General synthesis diagram 1:

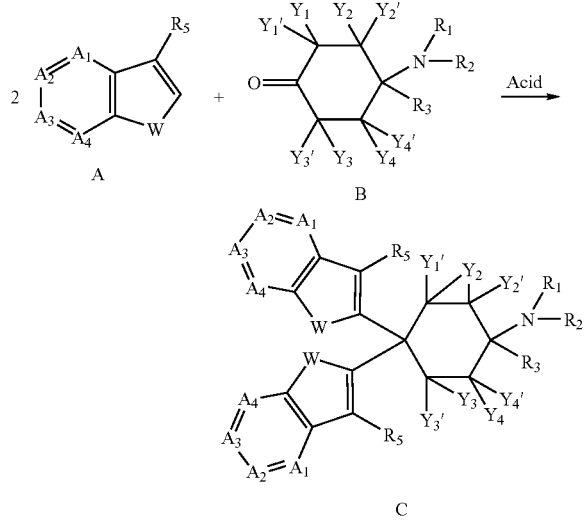

Compounds of the general formula A can be converted with compounds of the general formula B to compounds of the general formula C through the action of an inorganic acid or its trimethylsilyl ester or an inorganic acid or by adding a transition metal salt. Compounds of the general formula A are commercially available (exemplary syntheses, see also WO2008009416). The syntheses of the cyclohexanone derivatives with the general formula B are known in the specialist literature (cf. e.g. WO05066183, WO040043967, WO0290317, U.S. Pat. No. 4,065,573, Lednicer et al., *J. Med. Chem.*, 23, 1980, 424-430).

General synthesis diagram 2:

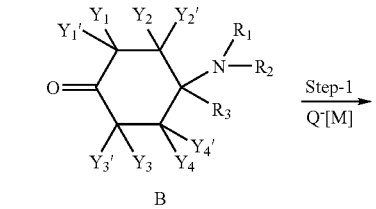

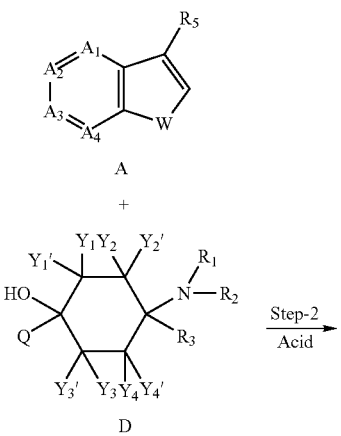

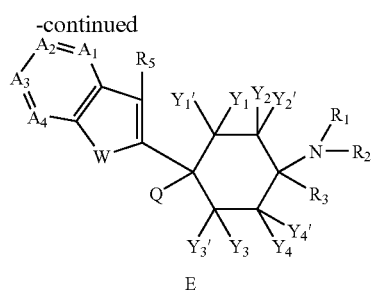

For Q = aryl, heteroaryl

In step 1 metal organyl compounds of type Q-[M] (with e.g. [M]=Li or [M]=MgX) are converted to compounds of type D in the sense of a 1,2-addition to cyclohexanones of the general formula B. Compounds of the general formula D can be converted with compounds of the general formula A to compounds of the general formula E through the action of an inorganic acid or its trimethylsilyl ester or an inorganic acid or by adding a transition metal salt (step 2).

General synthesis diagram 3.1:

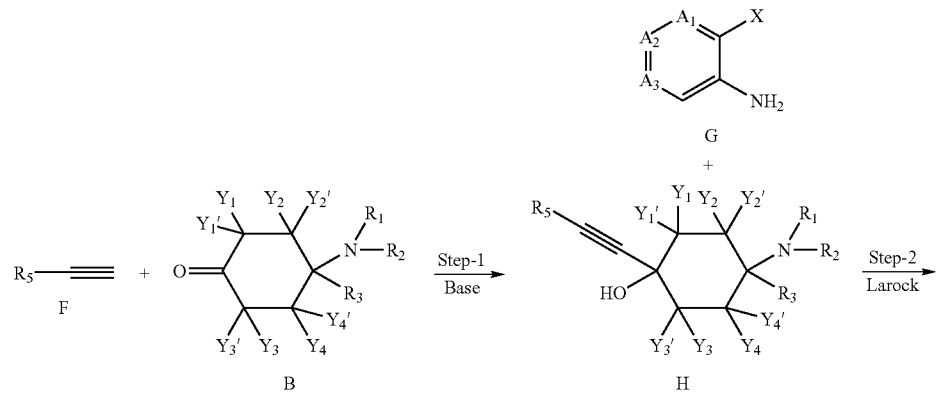

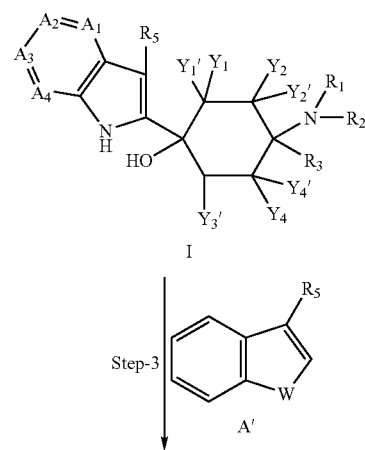

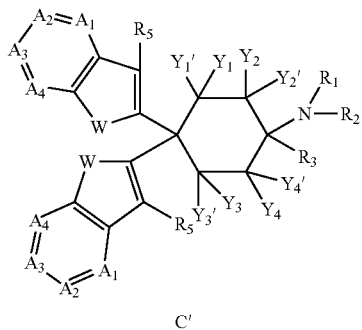

C'

The conversion of F and B to compounds of the general formula H can occur by using suitable basic reagents (step 1). In step 2 compounds of the general formula G, wherein X stands for a halogen residue or a sulphonic acid ester, are converted with alkines of the general formula H to indoles of the general formula I in the sense of an indole synthesis according to Larock by adding a palladium catalyst. Compounds of the general formula G are commercially available (exemplary syntheses, see also WO2008009416). The conversion of I with compounds of the general formula A' to compounds of the general formula C' can occur through action of an organic acid or its trimethylsilyl ester or an inorganic acid or by adding a transition metal salt (step 3).

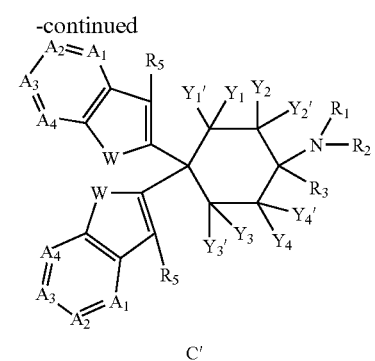

C'

Compounds of the general formula A can be converted with compounds of the general formula B to compounds of the general formula I' through the action of an inorganic acid or its trimethylsilyl ester or an inorganic acid or by adding a transition metal salt. Compounds of the general formula A are commercially available (exemplary syntheses, see also WO2008009416). The syntheses of the cyclohexanone derivatives with the general formula B are known in the specialist literature (cf. e.g. WO05066183, WO040043967, WO0290317, U.S. Pat. No. 4,065,573, Ledniceret al., *J. Med. Chem.*, 23, 1980, 424-430). The conversion of I' with compounds of the general formula A' to compounds of the general formula C' can occur through action of an organic acid or its trimethylsilyl ester or an inorganic acid or by adding a transition metal salt (step 2).

General Synthesis Diagram 4:

For Q=—$C_{1-8}$-(cyclo)aliphatic, —$C_{1-8}$-aliphatic-(hetero)aryl

General synthesis diagram 3.2:

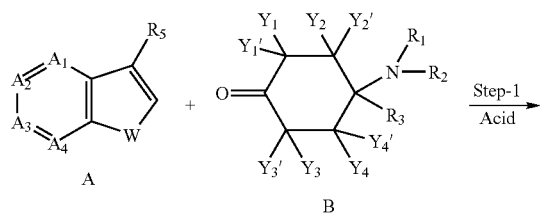

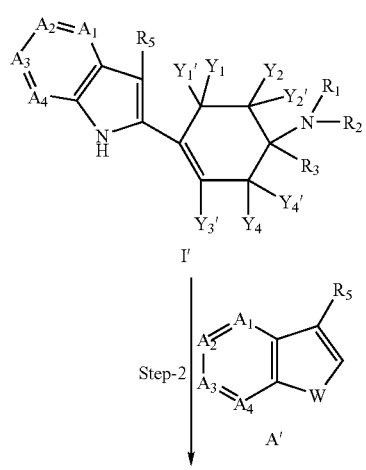

General synthesis diagram 4.1:

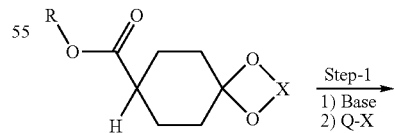

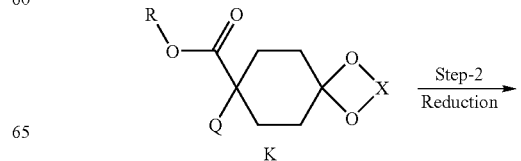

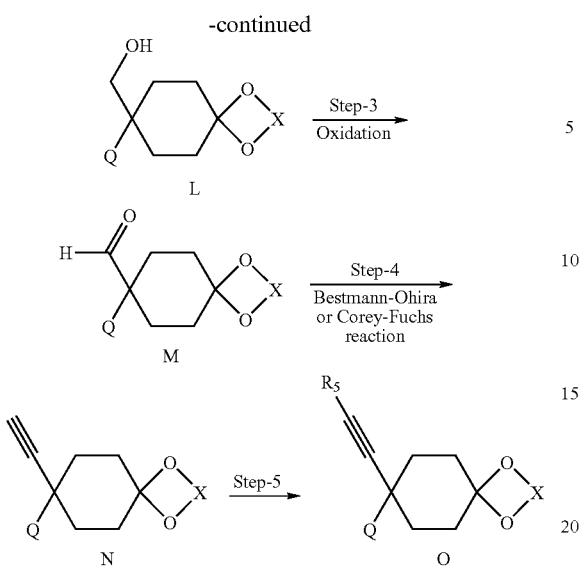

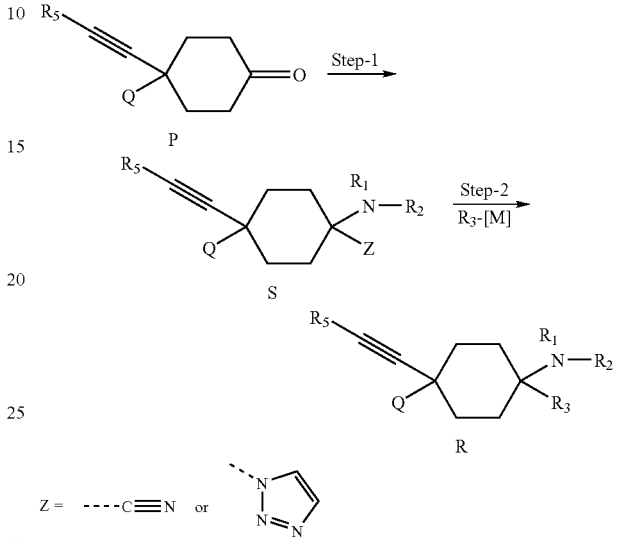

In step 1 compounds of formula J (X from the group alkyl, alkyl/alkylidene/alkylidene substituted with aryl or alkyl (saturated/unsaturated) are converted to compounds of the general formula K by deprotonation with a suitable base and conversion with electrophiles of the type Q-X. The reduction of the ester occurs in step 2. The alcohols of type L obtained can be converted to aldehydes M by oxidation (step 3). In step 4 aldehydes of the general formula M are converted to alkines of the general formula N in the sense of a Bestmann-Ohira reaction (Regitz, M. et al.; *Chem. Ber.*, 1968, 101; 3734-3743; Harned, A. M. et al. *Tetrahedron*, 2005, 61, 12093-12099) or according to a Corey-Fuchs reaction (Corey; Fuchs; THL 1972, 36, 3769-3772). The insertion of the residue $R_5$ to compounds of the general formula O occurs in step 5 either by deprotonation/alkylation ($R_5$—X) or by a transition metal-mediated coupling in the sense of a Sonogashira reaction.

General synthesis diagram 4.2:

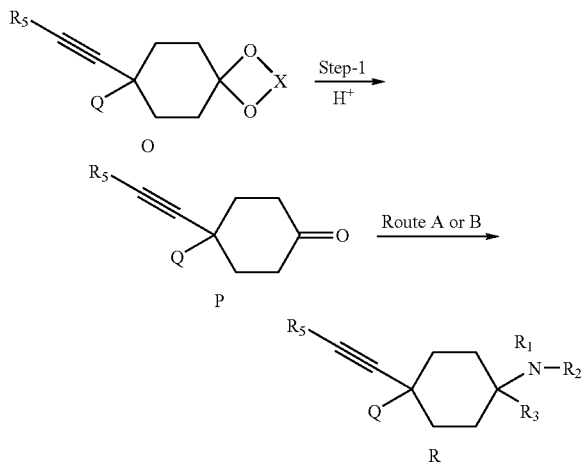

Compounds of formula P can be released from corresponding acetals O, or from their salts using methods known to the person skilled in the art, e.g. by deprotection by means of acids. In this case, X is selected from the group alkyl, alkyl/alkylidene/alkylidene substituted with aryl or alkyl (satu- rated/unsaturated). Compounds of formula P can be converted to alkines of type R. This can occur, for example, via the two following routes: (1) route A: aminonitrile or triazole route and (2) route B: imine route (see below).

General synthesis diagram 4.3:

(1) Route A: aminonitrile or triazole route

Ketones P can be converted to structures of formula S by reacting with amines and acid reactants Z-H. Suitable reactants Z-H are e.g. hydrogen cyanide, 1,2,3-triazole, benzotriazole or pyrazole. A particularly preferred path to compounds of structure S (with Z=—CN) is the conversion of ketones P with metal cyanides and the corresponding amine in the presence of acid. A further particularly preferred path to compounds of structure S is the conversion of ketones with 1,2,3-triazole and the corresponding amine in the presence of ? under dehydrating conditions.

Aminonitriles of formula S (with Z=—CN) can be converted to compounds R by reacting with corresponding organometallic compounds ($R_3$—[M], preferably Grignard compounds. The organometallic compounds are either commercially available or can be produced using known methods.

Aminotriazoles of formula S (with Z=-triazole) can be converted to compounds R by reaction with corresponding organometallic compounds ($R_3$—[M], preferably Grignard compounds. The organometallic compounds are either commercially available or can be produced using known methods.

The conditions can be seen from the specified literature: (a) Katritzky et al. *Synthesis,* 1992, 1295-1298. (b) Prashad, et al., *Tetrahedron Lett.* 2005, 46, 5455-5458.

General synthesis diagram 4.4:

(2) Route B: imine route

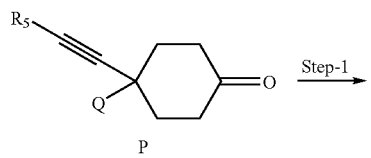

-continued

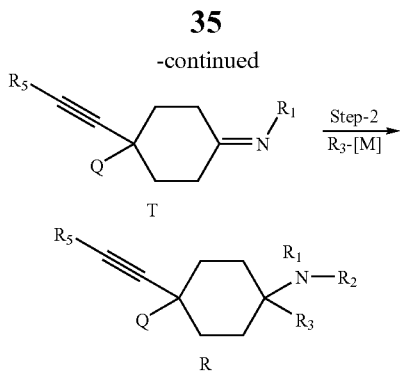

The imine T is synthesised from the ketone precursor P and is converted into the units R using a nucleophile ($R_3$—[M]). The required imine units T can be produced using a method known to the person skilled in the art (Layer, *Chem. Rev.*, 1963, 8, 489-510). For the addition of the organometallic species $R_3$—[M] to the imine T see: e.g. Maddox et al., *J. Med. Chem.*, 1965, 8, 230-235. Kudzma et al., *J. Med. Chem.*, 1989, 32, 2534-2542.

General synthesis diagram 4.5:

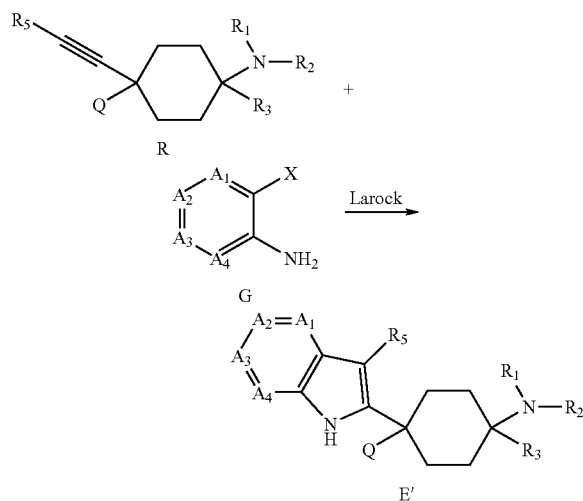

Compounds of the general formula G, wherein X stands for a halogen residue or a sulphonic acid ester, can be converted with alkines of the general formula R to indoles of the general formula E' in the sense of an indole synthesis according to Larock by adding a palladium catalyst. Compounds of the general formula G are commercially available or their production is known from the prior art or can be derived from the prior art in an obvious manner for the skilled person (exemplary syntheses, see also WO2008009416).

With respect to further details on the synthesis of the compounds according to the invention, reference can be made to the following in their full scope: WO2002/090317, WO2002/90330, WO2003/008370, WO2003/008731, WO2003/080557, WO2004/043899, WO2004/043900, WO2004/043902, WO2004/043909, WO2004/043949, WO2004/043967, WO2005/063769, WO2005/066183, WO2005/110970, WO2005/110971, WO2005/110973, WO2005/110974, WO2005/110975, WO2005/110976, WO2005/110977, WO2006/018184, WO2006/108565, WO2007/079927, WO2007/079928, WO2007/079930, WO2007/079931, WO2007/124903, WO2008/009415 and WO2008/009416.

EXAMPLES

The following examples serve to explain the invention in more detail, while not restricting it.

The yields of the compounds produced are not optimised. All temperatures are uncorrected. The term "ether" means diethyl ether, "EE" ethyl acetate and "DCM" dichloromethane. The term "equivalents" means substance amount equivalents, "mp" melting point or melting range, "decomp." decomposition, "RT" room temperature, "abs." absolute (free from water), "irac." racemic, "conc." concentrated, "min" minutes, "h" hours, "d" days, "% vol." percent by volume, "% m" percent by mass and "M" is a concentration detail in mol/l.

Silica gel 60 (0.040-0.063 mm) from E. Merck, Darmstadt was used as the stationary phase for the column chromatography. The thin-film chromatography tests were conducted with silica gel 60 F 254 HPTLC chromatoplates from E. Merck, Darmstadt. The mixture ratios of mobile solvents for chromatography tests are always given in volume/volume.

Example No. 1

Step 1

1-butyl-N,N-dimethyl-4,4-bis(3-methyl-5-(trifluoromethyl)-1H-indol-2-yl)cyclohexanamine 4-butyl-4-(dimethylamino)cyclohexanone (395 mg, 2 mmol, synthesis cf. WO2008009415, ketone unit Ket-4) together with 3-methyl-5-trifluoromethyl-1H-indole (398 mg, 2 mmol, synthesis cf. WO2008009415, indole unit Ind-7) was dissolved in dichloromethane (20 ml). Trifluoromethane sulphonic acid (0.2 ml, 338 mg, 2.25 mmol) was then added. This was stirred for 3 d at RT. For work up the reaction mixture was mixed with 1N NaOH (10 ml) and stirred for 10 min. After phase separation the aqueous phase was extracted with dichloromethane (2×10 ml). The combined organic phases were dried with sodium sulphate, filtered and concentrated to low volume in a vacuum. 741 mg of light brown solid was obtained, which was separated by chromatography [silica gel 60 (80 g); ethyl acetate/methanol (15:1; 1.51); (10:1; 500 ml); 1:1; 500 ml)].

Yield: 103 mg (9%)

$^{13}$C NMR (101 MHz, CDCl$_3$) δ ppm: 8.9, 10.1, 14.0, 23.7, 26.6, 29.6, 29.9, 37.3, 42.4, 56.1, 107.6, 109.6, 110.6, 110.9, 115.7, 115.8, 116.0, 116.1, 117.9, 118.5, 121.0, 121.3, 121.5, 121.6, 121.8, 121.9, 122.1, 122.4, 124.1, 124.2, 126.9, 129.6, 129.8, 135.3, 135.9, 138.0, 140.5

Step 2

1-butyl-N,N-dimethyl-4,4-bis(3-methyl-5-(trifluoromethyl)-1H-indol-2-yl)cyclohexanamine 2-hydroxypropane-1,2,3-tricarboxylate (1:1) (Example No. 1)

1-butyl-N,N-dimethyl-4,4-bis(3-methyl-5-(trifluoromethyl)-1H-indol-2-yl)cyclohexanamine (100 mg, 0.17 mmol) was dissolved in ethanol (10 ml) and mixed with citric acid (36 mg, 0.187 mmol) dissolved in hot ethanol (3 ml). The clear colourless solution was stirred for 48 h and then concentrated to low volume. After adding diethyl ether (10 ml), the mixture was stirred for 2 h at RT and the precipitate was then aspirated.

Yield: 68 mg (53%)
Melting point: 177-179° C.

Example No. 2

Step 1

1-butyl-4,4-bis(5-fluoro-3-methyl-1H-indol-2-yl)-N,N-dimethylcyclohexanamine 5-fluoro-3-methyl indole (596 mg, 4 mmol) together with 4-butyl-4-(dimethylamino)-cyclohexanone (788 mg, 4 mmol, synthesis cf. WO2008009415, ketone unit Ket-4) was dissolved in dichloromethane (30 ml) and mixed with trifluoromethane sulphonic acid (400 µl, 4.6 mmol). The batch was stirred for 24 h at RT. For work up the reaction mixture was mixed with 2N NaOH (30 ml) and stirred for 20 min at RT. After separation of the organic phase the aqueous phase was extracted with dichloromethane (3×15 ml). The combined organic extracts were dried over $Na_2SO_4$ and then concentrated to low volume. The raw product obtained (1.4 g) was purified by column chromatography [silica gel 60 (50 g); ethyl acetate (500 ml)].

Yield: 400 mg (31%), white solid

Step 2

1-butyl-4,4-bis(5-fluoro-3-methyl-1H-indol-2-yl)-N,N-dimethylcyclohexanamine; hydrochloride (1:1) (Example No. 2)

1-butyl-4,4-bis(5-fluoro-3-methyl-1H-indol-2-yl)-N,N-dimethylcyclohexanamine (400 mg, 0.84 mmol) was dissolved in ethyl methyl ketone (50 ml). $Me_3SiCl$ (214 µl, 1.68 mmol) was then added in drops at RT and stirred for 1 h. A white precipitate separated out. The precipitate was aspirated, washed with ethyl methyl ketone (2×5 ml) and then dried.

Yield: 323 mg (75%), white solid
Melting point: 262-304° C.
$^{13}$C NMR (101 MHz, DMSO-D6) δ ppm: 8.3, 9.1, 13.7, 22.5, 25.4, 26.9, 29.8, 30.2, 37.3, 41.1, 65.9, 102.2, 102.4, 106.3, 106.4, 106.7, 106.8, 108.3, 108.4, 108.6, 108.7, 111.4, 111.5, 111.7, 111.8, 129.4, 129.5, 129.6, 129.7, 131.3, 131.4, 138.6, 139.1, 155.5, 155.6, 157.8, 157.9

Example No. 3

Step 1

1-benzyl-N,N-dimethyl-4,4-bis(3-(2-(pyridin-4-yl)ethyl)-1H-indol-2-yl)cyclohexanamine 3-(2-pyridin-4-ylethyl)-1H-indole (667 mg, 3 mmol, synthesis cf. WO2008009415, indole unit Ind-14) together with 4-benzyl-4-(dimethylamino)cyclohexanone (652 mg, 3 mmol, synthesis cf. WO2008009415, ketone unit Ket-3) was dissolved in abs. dichloromethane (45 ml) and mixed with trifluoromethane sulphonic acid (0.553 ml, 6.3 mmol). The batch was stirred for 67 h at RT, and a brown oil separated out. For work up the reaction solution was mixed with 1N NaOH (10 ml) and THF (10 ml). The mixture was stirred a further 60 min. After separation of the phases the aqueous phase was extracted with dichloromethane (3×10 ml). The combined organic extracts were dried over $Na_2SO_4$ and then concentrated to low volume. The raw product obtained (1.22 g) was purified by column chromatography [silica gel 60 (100 g); ethyl acetate/methanol (10:1, 1100 ml), ethyl acetate/methanol (2:1, 500 ml) ethyl acetate/methanol (1:2, 750 ml)].

Yield: 152 mg
Melting point: 314-317° C.
$^{13}$C-NMR (101 MHz, DMSO-d6) δ ppm: 14.0, 26.3, 26.9, 29.4, 30.4, 34.5, 34.9, 37.0, 39.8, 56.9, 108.9, 109.2, 111.2, 111.4, 117.4, 117.5, 118.2, 118.3, 119.9, 120.0, 123.6, 123.7, 125.4, 127.5, 128.3, 128.6, 130.4, 134.3, 134.6, 138.7, 139.2, 142.1, 149.0, 149.1, 150.7

Step 2

1-benzyl-N,N-dimethyl-4,4-bis(3-(2-(pyridin-4-yl)ethyl)-1H-indol-2-yl)cyclohexanamine; 2-hydroxypropane-1,2,3-tricarboxylate (2:3) (Example No. 3)

1-benzyl-N,N-dimethyl-4,4-bis(3-(2-(pyridin-4-yl)ethyl)-1H-indol-2-yl)cyclohexanamine (128 mg, 0.182 mmol) and citric acid (36 mg, 0.187 mmol) were dissolved in methanol (30 ml). The clear solution was concentrated to low volume in a vacuum and the residue dissolved in ethanol (5 ml). Ethyl acetate (10 ml) and diethyl ether (15 ml) were slowly added in drops to the solution at RT. The citrate separated out as a white solid. The mixture was stirred for 1 h at RT, then filtered and washed with diethyl ether.

Yield: 94 mg (60%), white solid
Melting point: 155-165° C.

Example No. 4

N,N-dimethyl-4,4-bis(3-(2-(pyridin-4-yl)ethyl)-1H-indol-2-yl)-1-(thiophen-2-yl)cyclohexanamine (Example No. 4)

3-(2-pyridin-4-ylethyl)-1H-indole (667 mg, 3 mmol, synthesis cf. WO2008009415, indole unit Ind-14) together with 4-(dimethylamino)-4-(thiophen-2-yl)cyclohexanone (671 mg, 3 mmol, synthesis cf. WO2008009415, ketone unit Ket-12) was dissolved in abs. dichloromethane (45 ml) and mixed with trifluoromethane sulphonic acid (0.660 ml, 7.43 mmol). The batch was stirred for 64 h at RT, and a brown oil separated out. For work up the reaction solution was mixed with 1N NaOH (30 ml) and methanol (10 ml). The mixture was stirred a further 60 min. After separation of the phases the aqueous phase was extracted with dichloromethane (3×10 ml). The combined organic extracts were dried over $Na_2SO_4$ and then concentrated to low volume. The raw product obtained (1.33 g) was purified by column chromatography [silica gel 60 (100 g); ethyl acetate/methanol 10:1, (1650 ml), ethyl acetate/methanol (5:1, (600 ml)].

Yield: 99 mg, yellow solid
Melting point: 277-282° C.
$^{13}$C-NMR (101 MHz, DMSO d6) δ ppm: 26.5, 26.6, 31.5, 32.8, 34.8, 34.9, 37.8, 38.9, 58.5, 109.4, 109.5, 111.4, 117.6, 118.4, 120.2, 123.7, 124.7, 126.3, 128.5, 128.6, 134.5, 134.6, 149.06, 149.1, 150.6.

Example No. 5

2,2'-(4-butyl-4-(pyrrolidin-1-yl)cyclohexan-1,1-diyl)bis(3-(2-(pyridin-4-yl)ethyl)-1H-indole) (Example No. 5)

3-(2-pyridin-4-ylethyl)-1H-indole (667 mg, 3 mmol, synthesis cf. WO2008009415, indole unit Ind-14) together with 4-butyl-4-(pyrrolidin-1-yl)cyclohexanone (671 mg, 3 mmol, synthesis cf. WO2008009415, ketone unit Ket-14) was dissolved in abs. dichloromethane (45 ml) and mixed with trifluoromethane sulphonic acid (0.613 ml, 6.9 mmol). The batch was stirred for 64 h at RT, and a brown oil separated out. For work up the reaction solution was mixed with 1N NaOH (30 ml) and methanol (10 ml). The mixture was stirred a further 60 min. After separation of the phases the aqueous phase was extracted with dichloromethane (3×10 ml). The combined organic extracts were dried over $Na_2SO_4$ and then concentrated to low volume. The raw product obtained (1.35 g) was purified by column chromatography [silica gel 60 (90 g); ethyl acetate/methanol (1:1 (2400 ml)].

Yield: 48 mg, beige-coloured solid
Melting point: 277-285° C.
$^{13}$C-NMR (101 MHz, $CDCl_3$) δ ppm: 14.1, 23.7, 24.6, 26.4, 26.6, 26.9, 27.0, 30.8, 31.3, 32.1, 35.4, 35.9, 41.5, 44.1, 54.8, 110.1, 110.9, 111.2, 111.9, 118.1, 118.4, 119.5, 119.8, 121.5, 121.8, 123.7, 129.2, 129.4, 134.1, 134.7, 137.7, 140.4, 149.5, 149.6, 150.9, 151.1.

Example No. 6

N-methyl-1-phenyl-4,4-bis(3-(2-(pyridin-4-yl)ethyl)-1H-indol-2-yl)cyclohexanamine (Example No. 6)

3-(2-pyridin-4-ylethyl)-1H-indole (667 mg, 3 mmol, synthesis cf. WO2008009415, indole unit Ind-14) together with 4-(methylamino)-4-phenylcyclohexanone (610 mg, 3 mmol, synthesis cf. WO2008009415, ketone unit Ket-15) was dissolved in abs. dichloromethane (45 ml) and mixed with trifluoromethane sulphonic acid (0.613 ml, 6.9 mmol). The batch was stirred for 64 h at RT, and a brown oil separated out. For work up the reaction solution was mixed with 1N NaOH (30 ml) and methanol (10 ml). The mixture was stirred a further 60 min. After separation of the phases the aqueous phase was extracted with dichloromethane (3×10 ml). The combined organic extracts were dried over $Na_2SO_4$ and then concentrated to low volume. The raw product obtained (1.47 g) was purified by column chromatography [silica gel 60 (90 g); ethyl acetate/methanol 5:1 (1200 ml); ethyl acetate/methanol 1:1 (1200 ml)].

Yield: 100 mg, yellow solid
Melting point: 115-120° C.
$^{13}$C-NMR (101 MHz, $CDCl_3$) δ ppm: 26.7, 26.8, 26.9, 27.4, 28.8, 31.8, 32.7, 35.5, 35.7, 41.6, 56.8, 110.6, 110.8, 111.06, 111.1, 111.4, 118.2, 118.3, 119.6, 119.7, 121.7, 121.8, 123.7, 124.0, 126.3, 126.7, 127.1, 128.2, 128.3, 128.4, 129.1, 129.3, 134.4, 134.5, 137.6, 139.1, 149.48, 149.53, 150.9, 151.1

Example No. 7 and Example No. 8

Step 1

4-(dimethylamino)-4-phenyl-1-(thiophen-2-yl)cyclohexanol (polar and non-polar diastereomer)

4-(dimethylamino)-4-phenylcyclohexanone (2.17 g, 10 mmol, synthesis cf. WO2008009415, ketone unit Ket-10) was provided in absolute THF (30 ml) and within 10 min mixed with 2-thienyl magnesium bromide solution (1M in THF, 22.5 ml, 22.5 mmol). The reaction solution was heated until boiling for 2 h with reflux. For work up the solution was carefully mixed with ice pieces and saturated $NH_4Cl$ solution (25 ml) with ice bath cooling, then extracted with ethyl acetate (3×30 ml). The combined organic phases were washed with water (20 ml) and saturated NaCl solution (20 ml) and dried over sodium sulphate. The volatile constituents were then removed completely in a vacuum. The chromatographic separation of the substance mixture (3.78 g) on silica gel 60 (150 g) occurred with ethyl acetate/methanol (1:1).

Yield (non-polar diastereomer): 430 mg (14%), beige-coloured solid
$^{13}$C NMR (101 MHz, DMSO-D6) δ ppm: 28.7, 35.3, 37.8, 58.2, 69.8, 121.4, 123.2, 126.2, 126.4, 126.6, 127.2, 139.0, 156.4

Yield (polar diastereomer): 980 mg (33%), beige-coloured solid
Melting point: 136-141° C.
$^{13}$C NMR (101 MHz, DMSO-D6) δ ppm: 28.3, 36.5, 37.9, 60.4, 69.5, 121.3, 123.3, 126.2, 126.3, 127.5, 127.6, 136.5, 155.8

Step 2

N,N-dimethyl-4-(3-methyl-1H-indol-2-yl)-1-phenyl-4-(thiophen-2-yl)cyclohexanamine (non-polar diastereomer)

Skatole (430 mg, 3.28 mmol) was provided with the exclusion of moisture together with 4-(dimethylamino)-4-phenyl-1-(thiophen-2-yl)cyclohexanol (350 mg, 1.16 mmol, more polar diastereoisomer) in dry dichloromethane (40 ml) and quickly mixed with trifluoromethane sulphonic acid trimethylsilyl ester (0.23 ml, 1.27 mmol). The batch was stirred for 24 h at RT. For work up the precipitated precipitate was separated by means of a fritted glass filter and dried. This was mixed with dichloromethane (10 ml) and 2N NaOH (2 ml) and the suspension stirred for 2.5 days. The organic phase was separated and the aqueous phase extracted with dichloromethane (3×20 ml). The combined organic phases were dried over $MgSO_4$ and then concentrated to low volume.

Yield (non-polar diastereomer): 110 mg (22%), light yellow solid
Melting point: from 215° C.
13C NMR (101 MHz, $CDCl_3$) δ ppm: 10.1, 28.5, 34.2, 37.2, 42.4, 68.4, 105.8, 110.8, 117.7, 118.2, 119.1, 120.9, 121.9, 123.6, 126.4, 128.9, 129.1, 129.6, 129.7, 129.8, 135.2, 135.5, 152.9.

Step 3

N,N-dimethyl-4-(3-methyl-1H-indol-2-yl)-1-phenyl-4-(thiophen-2-yl)cyclohexanamine; 2-hydroxypropane-1,2,3-tricarboxylate (1:1) (Example No. 7, non-polar diastereomer)

N,N-dimethyl-4-(3-methyl-1H-indol-2-yl)-1-phenyl-4-(thiophen-2-yl)cyclohexanamine (90 mg, 0.22 mmol, non-polar diastereomer) was dissolved in propan-2-ol (20 ml) in the boiling heat and mixed with a hot solution of citric acid [60 mg, 0.31 mmol, in propan-2-ol (2 ml)]. After concentration of the solvent to 1-2 ml a precipitate separated out. The batch was left for 18 h at 5° C. to complete the precipitation, then the solid was separated by means of a fritted glass filter and dried.

Yield: 55 mg (41%), vitreous solid
1H NMR (300 MHz, $CDCl_3$) δ ppm: 1.55-1.78 (br s, 2H), 1.79-1.99 (br s 3H), 2.05-2.29 (br s, 6H), 2.3-2.67 (m, 7H), 2.94-3.02 (m, 3H), 6.57 (s, 1H), 6.70-7.81 (m, 1H), 10.77 (s, 1H)

Example No. 8

N,N-dimethyl-4-(3-methyl-1H-indol-2-yl)-1-phenyl-4-(thiophen-2-yl)cyclohexanamine (Example No. 8, polar diastereomer)

The mother liquor obtained in step 2 after separation of the precipitate was mixed with 2N NaOH (10 ml) and stirred for 10 min. The organic phase was then separated and the aqueous phase extracted with dichloromethane (4×20 ml). The combined organic phases were dried over $MgSO_4$ and then concentrated to low volume, and the residue (670 mg) was purified by chromatography [silica gel 60 G (10 g); ethyl acetate (100 ml)].

Yield: 252 mg (52%)
Melting point: 202-205° C. (from methanol)
$^{13}$C NMR (101 MHz, $CDCl_3$) δ ppm: 9.6, 30.2, 33.6, 38.0, 43.4, 60.6*, 106.0*, 110.2, 117.9, 118.9, 121.2, 124.3*, 126.7, 126.8, 127.6*, 127.8*, 130.3, 133.7
* spread signals.

Example No. 9

Step 1

4-(dimethylamino)-1,4-diphenylcyclohexanol (polar and non-polar diastereomer)

A solution of phenyl magnesium bromide (20 ml, 1M in THF, 20 mmol) was added within 10 min to a solution of 4-(dimethylamino)-4-phenylcyclohexanone (2.17 g, 10 mmol, synthesis cf. WO2008009415, ketone unit Ket-10) in abs. THF (20 ml). During this, the batch increased in temperature to approx. 40° C. After the addition ended the batch was heated to boiling for 2 h. After approx. 1 h a precipitate separated out. For work up the batch was cooled with ice and mixed with ice pieces (approx. 2 g) after approx. 5° C. was reached. Saturated $NH_4Cl$ solution (20 ml) was then added to the mixture. The organic phase was separated, the aqueous phase was extracted with ethyl acetate (3×20 ml). The combined organic extracts were dried over $MgSO_4$ and then concentrated to low volume. The residue (3.1 g) obtained was purified by chromatography [silica gel 60 G (10 g); ethyl acetate (100 ml), ethyl acetate/ethanol 1:1 (100 ml)].

Yield (non-polar diastereoisomer): 405 mg (13%), colourless solid
Melting point: 114-115° C. (from methanol)
$^{13}$C NMR (101 MHz, $CDCl_3$) δ ppm: 29.2, 34.5, 38.1, 58.7, 72.9, 124.8, 126.4, 126.7, 126.8, 127.4, 128.2, 139.34, 148.9

Yield (polar diastereoisomer): 881 mg (26%), colourless solid
Melting point: 123-126° C. (from methanol)
$^{13}$C NMR (101 MHz, CDCl3) δ ppm: 28.6, 35.8, 38.2, 61.5, 72.3, 124.5, 126.7, 127.9, 128.0, 128.1, 135.8, 148.5

Step 2

N,N-dimethyl-4-(3-methyl-1H-indol-2-yl)-1,4-diphenylcyclohexanamine (a diastereomer)

Skatole (393 mg, 3 mmol) was provided together with 4-(dimethylamino)-1,4-diphenylcyclohexanol (590 mg, 2 mmol, polar diastereomer) in dichloromethane (40 ml) and quickly mixed with trifluoromethane sulphonic acid trimethylsilyl ester (0.6 ml, 3.31 mmol). The batch was stirred for 43 h at RT. For work up the batch was mixed with 2N NaOH (20 ml) and stirred for 10 min. The organic phase was then separated and the aqueous phase extracted with dichloromethane (3×20 ml). The combined organic phases were dried over $MgSO_4$ and then concentrated to low volume. The residue obtained (945 mg) was purified by chromatography [silica gel 60 G (10 g); hexane/ethyl acetate 1:1 (100 ml]. The amine mixture obtained was dissolved in dichloromethane (5 ml) and mixed with 2N HCl (5 ml). An insoluble precipitate (136 mg, 15% yield, melting point: 303-307° C.) was obtained that was separated from the phase mixture by filtration. The solid was then mixed with dichloromethane (10 ml) and 2N NaOH (10 ml) and stirred. After 17 h the clear two-phase system obtained was separated and the aqueous phase extracted with dichloromethane (3×20 ml). The combined organic phases were dried over $MgSO_4$ and then concentrated to low volume.

Yield: 114 mg (14%)
Melting point: 193-207° C.

Step 3

N,N-dimethyl-4-(3-methyl-1H-indol-2-yl)-1,4-diphenylcyclohexanamine; 2-hydroxypropane-1,2,3-tricarboxylate (1:1) (Example No. 9, a diastereomer)

N,N-dimethyl-4-(3-methyl-1H-indol-2-yl)-1,4-diphenylcyclohexanamine (120 mg, 0.29 mmol) was heated in 2-propanol (10 ml) in the boiling heat and mixed with a hot solution of citric acid [70 mg, 0.36 mmol, in 2-propanol (2 ml)]. After concentration of the solvent to approx. 5 ml a precipitate separated out. The batch was left for 18 h at 5° C. to complete the precipitation, then the solid was separated off by a fritted glass filter and dried.

Yield: 77 mg (44%), vitreous solid
$^{13}$C NMR (101 MHz, DMSO-$d_6$) δ ppm: 10.0, 29.1*, 31.0, 32.4*, 37.3, 43.8*, 71.4, 105.5, 110.6, 117.4*, 118.1*, 120.5*, 125.3*, 125.9, 128.1*, 128.6, 129.0*, 129.7, 135.1, 147.3*, 171.1, 176.2*
* spread signals.

Example No. 10

Step 1

N,N-dimethyl-4,4-bis(3-methylbenzofuran-2-yl)-1-phenylcyclohexanamine 3-methylbenzofuran (354 mg, 3 mmol) together with 4-(dimethylamino)-4-phenylcyclohexanone (651 mg, 3 mmol, synthesis cf. WO2008009415, ketone unit Ket-10) was dissolved in dichloromethane (25 ml) and mixed with trifluoromethane sulphonic acid (0.3 ml, 3.4 mmol). The batch was stirred for 20 h at RT. For work up the reaction mixture was mixed with 2N NaOH (10 ml). The mixture was stirred a further 20 min. After separation of the phases the aqueous phase was extracted with dichloromethane (3×20 ml). The combined organic extracts were dried over $MgSO_4$ and then concentrated to low volume. The raw product (950 mg) obtained was purified by column chromatography (mobile solvent: EtOAc) and then recrystallised from ethanol (60 ml).

Yield: 182 mg
Melting point: 164-166° C.

Step 2

N,N-dimethyl-4,4-bis(3-methylbenzofuran-2-yl)-1-phenylcyclohexanamine; 2-hydroxypropane-1,2,3-tricarboxylate (1:1) (Example No. 10)

N,N-dimethyl-4,4-bis(3-methylbenzofuran-2-yl)-1-phenylcyclohexanamine (410 mg, 0.88 mmol) was dissolved in ethanol (70 ml) in the boiling heat and mixed with citric acid (300 mg, 1.6 mmol) dissolved in hot ethanol (10 ml). The solution was concentrated to approx. 10 ml and kept for 3 h at 5° C. The crystals obtained were separated off by means of a fritted glass filter.

Yield: 349 (60%)

Melting point: 161-164° C.

$^{13}$C NMR (101 MHz, DMSO-D6) δ ppm: 7.4, 8.2, 28.6*, 29.9*, 37.3, 42.4, 43.6*, 71.7, 110.0, 110.6, 110.8, 111.4 119.0, 119.2, 122.3, 122.4, 123.9, 124.1, 128.5*, 130.2, 130.5, 152.0, 152.4, 171.2, 175.8

* spread signals.

Example No. 11

N,N-dimethyl-4,4-bis(3-methyl-1H-indol-2-yl)-1-phenylcyclohexanamine; 2-hydroxypropane-1,2,3-tricarboxylate (1:1) (Example No. 11)

3-methyl indole (262 mg, 2 mmol) together with 4-(dimethylamino)-4-phenylcyclohexanone (434 mg, 2 mmol, synthesis cf. WO2008009415, ketone unit Ket-10) was dissolved in dichloromethane (20 ml) and mixed with trifluoromethane sulphonic acid trimethylsilyl ester (0.44 ml, 2.45 mmol). The batch was stirred for 20 h at RT. For work up the reaction mixture was mixed with 2N NaOH (10 ml). After separation of the phases the aqueous phase was extracted with dichloromethane (2×20 ml). The combined organic extracts were dried over Na$_2$SO$_4$ and then concentrated to low volume. The raw product (638 mg) obtained was purified by column chromatography (mobile solvent: EtOAc). The solid (200 mg) obtained was dissolved in ethanol (3 ml) and mixed with citric acid (48 mg, 0.25 mmol). The solution was left for 3 days at RT. The solid was separated off by means of a fritted glass filter.

Yield: 79 mg (14%)

Melting point: from 168° C.

1H NMR (400 MHz, DMSO-D6) δ ppm: 1.78 (s, 3H), 1.93-2.15 (m, 6H), 2.26 (s, 6H), 2.45-2.70 (m, 6H) 2.83-2.95 (m, 2H), 4.14-4.67 (br s, 1H), 6.82-6.88 (m, 1H), 6.89-6.99 (m, 2H), 7.02-7.08 (m, 1H), 7.21-7.28 (m, 2H), 7.37-7.43 (m, 2H), 7.43-7.48 (m, 1H), 7.48-7.56 (m, 2H), 7.60-7.70 (m, 2H), 10.30 (s, 1H), 10.82 (s, 1H)

Example No. 12

Step 1

1-butyl-N,N-dimethyl-4,4-bis(3-(2-(pyridin-4-yl)ethyl)-1H-indol-2-yl)cyclohexanamine 3-(2-pyridin-4-ylethyl)-1H-indole (667 mg, 3 mmol, synthesis cf. WO2008009415, indole unit Ind-14) together with 4-butyl-4-(dimethylamino)cyclohexanone (592 mg, 3 mmol, synthesis cf. WO2008009415, ketone unit Ket-4) was dissolved in dichloromethane (45 ml) and mixed with trifluoromethane sulphonic acid (0.553 ml, 6.3 mmol). The batch was stirred for 67 h at RT, and a brown oil separated out. For work up the reaction solution was mixed with 1N NaOH (10 ml) and THF (10 ml). The mixture was stirred a further 60 min. After separation of the phases the aqueous phase was extracted with dichloromethane (3×10 ml). The combined organic extracts were dried over Na$_2$SO$_4$ and then concentrated to low volume. The raw product obtained (1.24 g) was purified by column chromatography [silica gel 60 (100 g); ethyl acetate/methanol (10:1, 1200 ml), ethyl acetate/methanol (5:1, 600 ml) ethyl acetate/methanol (2:1, 700 ml), ethyl acetate/methanol (1:2, 750 ml), methanol (800 ml)].

Yield: 121 mg

Melting point: 274-282° C.

$^{13}$C-NMR (101 MHz, CDCl$_3$) δ ppm: 14.0, 23.1, 26.0, 26.5, 26.8, 28.9, 30.7, 34.7, 35.0, 37.2, 55.5, 109.1, 109.6, 111.4, 111.5, 117.5, 117.6, 118.3, 118.4, 120.1, 123.7, 128.6, 134.5, 134.8, 139.6, 141.4, 149.1, 150.7

Step 2

1-butyl-N,N-dimethyl-4,4-bis(3-(2-(pyridin-4-yl)ethyl)-1H-indol-2-yl)cyclohexanamine; 2-hydroxypropane-1,2,3-tricarboxylate (1:1) (Example No. 12)

1-butyl-N,N-dimethyl-4,4-bis(3-(2-(pyridin-4-yl)ethyl)-1H-indol-2-yl)cyclohexanamine (96 mg, 0.154 mmol) and citric acid (31 mg, 0.161 mmol) were dissolved in methanol (4 ml). Ethyl acetate (4 ml) and diethyl ether (16 ml) were slowly added in drops to the clear solution at RT. A white powder was separated out. The mixture was stirred for 2 h at RT, then filtered and washed with diethyl ether.

Yield: 100 mg (80%), white solid

Melting point: 134-142° C.

Example No. 13

Step 1

Dimethyl 2,2'-(2,2'-(4-butyl-4-(dimethylamino)cyclohexan-1,1-diyl)bis(1H-indol-3,2-diyl))diacetate (Example No. 13)

3-indolyl methyl acetate (950 mg, 5.02 mmol) together with 4-butyl-4-(dimethylamino)cyclohexanone (395 mg, 2.00 mmol) was dissolved in abs. dichloromethane (20 ml) and mixed with trifluoromethane sulphonic acid (0.230 ml, 2.62 mmol). The batch was stirred for 111 h at 23° C. For work up the reaction solution was mixed with 1N NaOH (10 ml). The mixture was stirred for 5 min. After separation of the phases the aqueous phase was extracted with dichloromethane (3×10 ml). The combined organic extracts were dried over Na$_2$SO$_4$ and then concentrated to low volume. The raw product obtained (brown oil, 1.55 g) was purified by column chromatography [silica gel 60 (70 g); ethyl acetate (600 ml), ethyl acetate/methanol (4:1 (1000 ml)]. The desired bisindole compound was obtained as a white solid (149 mg, 13%, mp 117-121° C.).

Example No. 13: $^{13}$C NMR (101 MHz, CDCl$_3$) δ ppm: 14.1, 23.8, 26.5, 29.7, 30.2, 30.9, 31.2, 31.4, 37.3, 44.3, 52.3, 52.4, 55.9, 101.4, 103.0, 110.8, 110.9, 117.7, 117.8, 118.9, 119.1, 121.6, 121.8, 129.0, 129.2, 135.1, 135.5, 139.5, 141.6, 174.8, 174.9

Olefin 4: $^{13}$C NMR (101 MHz, CDCl$_3$) δ ppm: 14.2, 23.6, 25.6, 26.8, 28.5, 30.5, 32.2, 38.0, 51.9, 55.9, 104.3, 110.5, 118.7, 119.8, 122.0, 127.6, 128.4, 134.9, 137.4, 172.7

Example No. 14

Step 1

2,2'-(2,2'-(4-butyl-4-(dimethylamino)cyclohexan-1,1-diyl)bis(1H-indol-3,2-diyl))diethanol (Example No. 14)

Dimethyl 2,2'-(2,2'-(4-butyl-4-(dimethylamino)cyclohexan-1,1-diyl)bis(TH-indol-3,2-diyl))diacetate (100 mg, 0.1791 mmol) was added to a suspension of lithium aluminum hydride (75 mg, 1.97 mmol) in abs. tetrahydrofuran (10 ml) in argon. The batch was stirred for 30 min at 23° C. With cooling 1 N sodium hydroxide solution (20 ml) was added and stirred for 5 min at room temperature. The mixture was extracted with diethyl ether (3×15 ml). The combined organic phases were dried with $Na_2SO_4$, filtered and the volatile constituents completely removed in a vacuum. The product was thus obtained as a white solid (melting point 174-178° C.) with a yield of 76 mg (90%).

Example No. 14: $^{13}$C-NMR (101 MHz, $CD_3OD$) δ ppm: 14.4, 24.7, 27.5, 29.3, 29.5, 30.1, 32.1, 32.8, 37.9, 42.9, 58.2, 63.0, 63.1, 108.3, 108.5, 111.88, 111.94, 118.77, 118.80, 119.6, 119.7, 121.7, 121.8, 130.92, 130.94, 136.37, 136.41, 141.0, 141.4

Example No. 15 and Example No. 16

Step 1

1-butyl-N,N-dimethyl-4-(3-(2-pyridin-4-yl)ethyl)-1H-indol-2-yl)cyclohex-3-enamine 3-[(2-pyridin-4-yl)ethyl]-1H-indol (1.38 g, 6.21 mmol) together with 4-butyl-4-(dimethylamino)cyclohexanone (1.23 g, 6.23 mmol) was mixed with HBr/glacial acetic acid (33% HBr, 6 ml) and stirred for 2 h at 23° C. The mixture was then diluted with dichloromethane (100 ml). 5N sodium hydroxide solution (50 ml) was added with cooling. The batch was stirred for 10 min at room temperature. After separation of the phases the aqueous phase was extracted with dichloromethane (3×20 ml). The combined organic extracts were dried over $Na_2SO_4$ and then concentrated to low volume. The raw product obtained (2.53 g, brown solid) was purified by chromatography [silica gel 60 (110 g); ethyl acetate/methanol (5:1 (1200 ml), methanol (1200 ml)]. 1.53 g (61%) of the target compound were obtained (melting point: 146-150° C.).

$^{13}$C-NMR (101 MHz, $CDCl_3$) δ ppm: 14.2, 23.7, 25.6, 26.0, 26.9, 28.5, 30.5, 32.3, 36.4, 38.0, 55.9, 110.4, 110.6, 118.3, 119.4, 121.8, 124.4, 126.5, 128.7, 129.2, 135.1, 136.3, 149.5, 151.2

Step 2

1-butyl-N,N-dimethyl-4-(3-methyl-1H-indol-2-yl)-4-(3-(2-pyridin-4-yl)ethyl)-1H-indol-2-yl)cyclohexylamine (Example No. 15, more non-polar diastereoisomer and Example No. 16, more polar diastereoisomer)

3-methyl-1H-indole (400 mg, 3.05 mmol) together with 1-butyl-N,N-dimethyl-4-(3-(2-pyridin-4-yl)ethyl)-1H-indol-2-yl)cyclohex-3-enamine (605 mg, 1.51 mmol) was dissolved in abs. dichloromethane (20 ml) and mixed with trifluoromethane sulphonic acid (0.32 ml, 3.64 mmol). The batch was stirred for 112 h at 23° C. For work up the reaction solution was mixed with 1N NaOH (20 ml). The mixture was stirred for 5 min. After separation of the phases the aqueous phase was extracted with dichloromethane (3×15 ml). The combined organic extracts were dried over $Na_2SO_4$ and then concentrated to low volume. The raw product obtained (brown oil, 1.12 g) was purified by column chromatography [silica gel 60 (60 g); ethyl acetate/methanol (5:1 (1200 ml)]. The more non-polar diastereoisomer (136 mg, 17%, mp 193-198° C.) and the more polar diastereoisomer (46 mg, 6%, mp 162-167° C.) were obtained as white solids.

Example No. 15: (more non-polar diastereoisomer): $^{13}$C-NMR (101 MHz, $CDCl_3$) δ ppm: 10.4, 14.1, 23.7, 26.2, 26.6, 29.9, 30.5, 31.6, 36.0, 37.4, 42.3, 56.0, 108.7, 109.9, 110.8, 118.0, 118.3, 118.2, 119.4, 121.3, 121.7, 123.8, 129.5, 130.2, 134.0, 134.6, 136.3, 140.1, 149.4, 151.4

Example No. 16: (more polar diastereoisomer): $^{13}$C-NMR (101 MHz, $CDCl_3$) δ ppm: 9.3, 14.1, 23.7, 26.5, 27.0, 29.6, 30.7, 31.6, 35.4, 37.4, 41.7, 56.1, 107.0, 110.6, 111.0, 111.5, 118.0, 118.3, 119.2, 119.5, 121.3, 121.6, 123.7, 129.3, 130.4, 134.0, 134.5, 137.9, 138.8, 149.5, 151.0

Example No. 17

Step 1

2-[2-(1H-indol-3-yl)-ethyl]-1,2,3,4-tetrahydroisoquinoline

A solution of 3-(2-bromo-ethyl)-1H-indole (4.48 g, 20 mmol) and isoquinoline (5.33 g, 40 mmol) in abs. dioxan (50 mL) was stirred for 6 h at 80° C. The solvent was then removed in a vacuum, the residue mixed with $CHCl_3$ (100 mL) and washed twice with water. The organic phase was dried over $Na_2SO_4$, concentrated to low volume in a vacuum, and the remaining residue purified by flash chromatography with $CHCl_3$/MeOH (50:1).

Yield: 4.78 g (86%), white solid $^1$H-NMR (DMSO-$d_6$): 2.76 (6H, m); 2.95 (2H, m); 3.66 (2H, s); 7.06 (6H, m); 7.18 (1H, s); 7.34 (1H, d); 7.56 (1H, d); 10.77 (1H, s).

Step 2

1-butyl-4,4-bis-(3-(2-(3,4-dihydro-1H-isoquinolin-2-yl)ethyl)-1H-indol-2-yl)-N,N-dimethylcyclohexylamine 2-[2-(1H-indol-3-yl)-ethyl]-1,2,3,4-tetrahydroisoquinoline (850 mg, 3.07 mmol) together with 4-butyl-4-(dimethylamino)cyclohexanone (300 mg, 1.52 mmol) was dissolved in abs. dichloromethane (10 ml) and mixed with trifluoromethane sulphonic acid (0.230 ml, 2.62 mmol). The batch was stirred for 6 d at 23° C. For work up the reaction solution was mixed with 1N NaOH (10 ml). The mixture was stirred for 5 min. After separation of the phases the aqueous phase was extracted with dichloromethane (3×10 ml). The combined organic extracts were dried over $Na_2SO_4$ and then concentrated to low volume. The raw product obtained (brown oil, 1.24 g) was purified by column chromatography [silica gel 60 (60 g); ethyl acetate (240 ml)]. The desired bisindole compound was obtained as off-white solid (89 mg, 8%), which according to the NMR spectrum contained impurities.

Bisindole compound: $^{13}$C NMR (101 MHz, $CDCl_3$) δ ppm: 14.1, 22.6, 22.8, 23.8, 26.5, 28.4, 28.7, 29.5, 30.7, 31.6, 37.5, 43.1, 50.8, 51.0, 56.1, 57.0, 58.9, 59.4, 108.6, 110.0, 110.5, 110.6, 117.6, 117.8, 118.4, 118.6, 121.0, 121.2, 125.6, 125.8, 126.8, 128.9, 129.2, 129.3, 134.3, 134.6, 134.8, 135.0, 135.4, 138.3, 140.3

Step 3

1-butyl-4,4-bis-(3-(2-(3,4-dihydro-1H-isoquinolin-2-yl)ethyl)-1H-indol-2-yl)-N,N-dimethylcyclohexylamine hydrochloride (Example No. 17)

1-butyl-4,4-bis-(3-(2-(3,4-dihydro-1H-isoquinolin-2-yl)ethyl)-1H-indol-2-yl)-N,N-dimethylcyclohexylamine (57 mg, 0.079 mmol) was dissolved in ethyl methyl ketone (2 ml). The solution was mixed with chlorotrimethyl silane (50 μl, 0.391 mmol) at RT. The clear reaction mixture immediately became cloudy. The mixture was stirred for 30 min at 23° C. The white precipitate was aspirated. The solid was washed with ethyl methyl ketone (3×0.5 ml) and then dried. The hydrochloride (48 mg, approx. 80%) was obtained as light beige-coloured solid.

Example No. 18

Step 1

4-dimethylamino-1-(4-methoxyphenyl)-4-phenylcyclohexanol (non-polar diastereoisomer and polar diastereoisomer)

4-(dimethylamino)-4-phenylcyclohexanone (4.34 g, 20 mmol) was dissolved in absolute tetrahydrofuran (60 ml) with the exclusion of oxygen, mixed with 4-methoxy phenyl magnesium bromide solution (90 ml, 45 mmol, 0.5N) with ice cooling and boiled for 2 h with reflux. For work up the batch was mixed with saturated $NH_4Cl$ solution (50 ml) with ice cooling and stirred for 10 min at room temperature. The aqueous phase was separated off and extracted with ethyl acetate (3×25 ml). The combined organic phases were dried over $Na_2SO_4$ and then concentrated to low volume. A raw product was isolated that was purified by chromatography [silica gel 60 (50 g); ethyl acetate (1000 ml), methanol (1000 ml)]. 2.016 g (31%, mp 174-175° C.) of more non-polar and 2.51 g (39%, mp 149-151° C.) of more polar product were obtained. Both could be recrystallised from ethyl acetate.

More non-polar diastereoisomer: $^{13}$C-NMR (101 MHz, DMSO-$D_6$) δ ppm: 28.7, 34.2, 37.8, 54.9, 58.0, 70.5, 113.0, 125.8, 126.1, 126.6, 127.2, 139.4, 142.7, 157.5

More polar diastereoisomer: $^{13}$C-NMR (101 MHz, DMSO-$D_6$) δ ppm: 28.1, 35.5, 37.9, 54.9, 60.7, 70.2, 113.0, 125.5, 126.1, 127.5, 127.8, 136.6, 142.1, 157.5

Step 2

4-(4-methoxyphenyl)-N,N-dimethyl-4-(3-methyl-1H-indol-2-yl)-1-phenylcyclohexylamine (Example No. 18, mixture of two diastereoisomers)

3-methyl-1H-indol (393 mg, 3 mmol) and the more non-polar 4-dimethylamino-1-(4-methoxyphenyl)-4-phenylcyclohexanol (651 mg, 2 mmol) were dissolved in absolute dichloromethane (50 ml) with the exclusion of oxygen, mixed with trifluoromethane sulphonic acid trimethylsilyl ester (581 μl, 3 mmol) and stirred for 16 h at room temperature. For work up the batch was mixed with 5N NaOH (50 ml) and stirred for 1 h at room temperature. The aqueous phase was separated and extracted with dichloromethane (3×25 ml). The combined organic phases were dried over $Na_2SO_4$ and then concentrated to low volume. A raw product was isolated that was separated by chromatography [silica gel 60 (50 g); ethyl acetate (1000 ml)]. The product was obtained as a white solid with a yield of 600 mg (68%) and a melting point of 90-95° C. This concerned a mixture of two diastereoisomers (approx. 1:1), which could not be separated because of the identical Rt value.

Example No. 18: diastereoisomer mixture: $^{13}$C-NMR (101 MHz, DMSO-$D_6$) δ ppm: 9.9, 30.1, 31.3, 32.2, 37.7, 43.4, 54.8, 104.7, 110.5, 110.6, 113.4, 113.4, 117.0, 117.1, 117.8, 117.9, 120.0, 120.1, 126.2, 126.4, 126.8, 127.0, 127.3, 127.5, 127.6, 128.2, 129.5, 129.7, 134.6, 134.7, 139.2, 157.0, 157.1

Example No. 19

Step 1

1-butyl-N,N-dimethyl-4,4-bis-(3-methyl-1H-indol-2-yl)cyclohexylamine (Example No. 19)

3-methyl-1H-indol (4 g, 30.492 mmol) together with 4-butyl-4-(dimethylamino)cyclohexanone (2 g, 10.14 mmol) was dissolved in abs. dichloromethane (40 ml) and mixed with trifluoromethane sulphonic acid (1.4 ml, 14.93 mmol). The batch was stirred for 6 d at 24° C. For work up the reaction solution was mixed with 1N NaOH (25 ml). The mixture was stirred for 25 min. After separation of the phases the aqueous phase was extracted with dichloromethane (3×20 ml). The combined organic extracts were dried over $Na_2SO_4$ and then concentrated to low volume. The raw product obtained (brown oil, 6.75 g) was purified by column chromatography [silica gel 60 (70 g); ethyl acetate/methanol 5:1 (1200 ml), ethyl acetate/methanol 2:1 (1200 ml)]. The desired bisindole compound was obtained as light yellow solid (2016 mg, 45%, mp: 192-195° C.).

Example No. 19: $^{13}$C NMR (101 MHz, CDCl$_3$) δ ppm: 9.4, 10.3, 14.1, 23.8, 26.6, 29.8, 29.9, 31.7, 37.3, 42.7, 56.0, 106.3, 108.3, 110.4, 110.6, 117.9, 118.2, 118.9, 119.2, 121.1, 121.5, 130.3, 130.6, 133.7, 134.4, 136.5, 138.8

Example No. 20

Step 1

2-[2-(1H-indol-3-yl)ethyl]indan-1,3-dione

Tryptamine (3.09 g; 19 mmol) was dissolved in toluol (300 ml). Phthalic anhydride (3 g; 20.2 mmol) was then added. The yellow reaction solution was boiled with reflux for 7 h (water separator). The course of the reaction was controlled by DC. For work up toluol was distilled off completely. The remaining yellow solid was recrystallised from cyclohexane/chloroform (1:1). 4.796 g (90%) of the product were obtained.

Step 2

2-(2-(2-(4-butyl-4-dimethylaminocyclohex-1-enyl)-1H-indol-3-yl)-ethyl)isoindol-1,3-dione 2-[2-(1H-indol-3-yl)ethyl]indan-1,3-dione (4.40 g, 15.16 mmol) together with 4-butyl-4-(dimethylamino)cyclohexanone (2.50 g, 12.67 mmol) was mixed with HBr/glacial acetic acid (33% HBr, 15 ml) and stirred for 5 h at 24° C. The mixture was then diluted with dichloromethane (50 ml). 5N sodium hydroxide solution (100 ml) was added with cooling. The batch was stirred for 10 min at room temperature. After separation of the phases the aqueous phase was extracted with dichloromethane (3×20 ml). The combined organic extracts were dried over $Na_2SO_4$ and then concentrated to low volume. The raw product obtained (5.81 g, brown oil) was purified by chromatography [silica gel 60 (110 g); ethyl acetate/methanol (2:1, (1200 ml)]. 1.98 g (33%) of the target compound were obtained (melting point: 125-130° C.).

$^{13}$C NMR (101 MHz, CDCl$_3$) δ ppm: 14.2, 23.6, 24.3, 25.6, 26.6, 28.5, 30.5, 32.3, 38.1, 38.5, 56.0, 107.8, 110.4, 118.5, 119.6, 121.9, 123.1, 126.8, 128.8, 129.1, 132.3, 133.8, 134.93, 136.5, 168.2

Step 3

2-(2-(2-(4-butyl-4-dimethylamino-1-(3-methyl-1H-indol-2-yl)cyclohexyl)-1H-indol-3-yl)ethyl)isoindolin-1,3-dione (Example No. 20, mixture of two diastereomers)

3-methyl-1H-indole (1.0 g, 7.62 mmol) together with 2-(2-(2-(4-butyl-4-dimethylamino-cyclohex-1-enyl)-1H-indol-3-yl)-ethyl)isoindol-1,3-dione (1.20 g, 2.56 mmol) was dissolved in abs. dichloromethane (15 ml) and mixed with trifluoromethane sulphonic acid (0.3 ml, 3.41 mmol). The batch was stirred for 6 d at 24° C. For work up the reaction solution was mixed with 1N NaOH (20 ml). The mixture was stirred for 10 min. After separation of the phases the aqueous phase was extracted with dichloromethane (3×15 ml). The combined organic extracts were dried over $Na_2SO_4$ and then concentrated to low volume. The raw product obtained (brown oil, 2.3 g) was purified by column chromatography [silica gel 60 (100 g); ethyl acetate/methanol 5:1 (600 ml), ethyl acetate/methanol 2:1 (1200 ml)]. The desired bisindole compound was obtained as light yellow solid (505 mg, 33%, mp: not determinable). According to the NMR spectrum it was a mixture of the two possible diastereoisomers in a ratio of approx. 30:70.

Example No. 20: $^{13}$C NMR (101 MHz, $CDCl_3$) δ ppm: 9.6, 10.2, 14.1, 23.8, 24.7, 26.5, 26.6, 29.7, 30.5, 31.6, 31.8, 37.4, 38.3, 38.7, 42.3, 42.7, 56.1, 106.5, 107.4, 108.1, 109.2, 110.6, 110.72, 110.75, 110.9, 117.8, 118.1, 118.2, 118.3, 118.8, 119.0, 119.4, 119.6, 121.0, 121.30, 121.32, 121.7, 123.1, 129.7, 129.8, 130.3 130.4, 132.16, 132.22, 133.8, 134.0, 134.4 134.5, 137.8, 138.7, 140.7, 168.4

Example No. 21

Step 1

1-(benzo[d][1,3]dioxol-5-yl)-4-(dimethylamino)-4-phenylcyclohexanol (more polar diastereoisomer)

4-(dimethylamino)-4-phenylcyclohexanone (4.34 g, 20 mmol) was dissolved in absolute tetrahydrofuran (60 ml) with the exclusion of oxygen, mixed with 3,4-(methylenedioxy)phenyl magnesium bromide solution (45 ml, 45 mmol, 1N) with ice cooling and boiled at reflux for 3 h. For work up the batch was mixed with saturated $NH_4Cl$ solution (50 ml) with ice cooling and stirred for 10 min at room temperature. The aqueous phase was separated and extracted with ethyl acetate (3×25 ml). The combined organic phases were dried over $Na_2SO_4$ and then concentrated to low volume. A raw product was isolated that was purified by chromatography [silica gel 60 (50 g); ethyl acetate (1000 ml), methanol (1000 ml)]. 2.0 g (29%, p 104-107° C.) of more polar product were obtained. Only traces of more non-polar product were found.

More polar diastereoisomer: $^{13}$C-NMR (101 MHz, DMSO-$D_6$) δ ppm: 28.1, 35.6, 37.7, 60.7, 70.5, 100.5, 105.5, 107.3, 117.2, 126.2, 126.7, 127.4, 127.5, 127.7, 127.8, 136.5, 138.2, 144.5, 145.2, 146.7

Step 2

4-(benzo[d][1,3]dioxol-5-yl)-N,N-dimethyl-4-(3-methyl-1H-indol-2-yl)-1-phenylcyclohexylamine (Example No. 21, one of two possible diastereoisomers)

3-methyl-1H-indole (393 mg, 3 mmol) and the more polar 1-(benzo[d][1,3]dioxol-5-yl)-4-(dimethylamino)-4-phenylcyclohexanol (679 mg, 2 mmol) were dissolved in absolute dichloromethane (50 ml) with the exclusion of oxygen, mixed with trifluoromethane sulphonic acid trimethylsilyl ester (581 µl, 3 mmol) and stirred for 16 h at room temperature. For work up the batch was mixed with 5N NaOH (50 ml) and stirred for 1 h at room temperature. The aqueous phase was separated and extracted with dichloromethane (3×25 ml). The combined organic phases were dried over $Na_2SO_4$ and then concentrated to low volume. A raw product was isolated that was purified by chromatography [silica gel 60 (50 g); ethyl acetate (1000 ml)]. The product was obtained as a white solid with a yield of 545 mg (60%) and a melting point of 235-238° C. This concerned one of two possible diastereoisomers.

Example No. 21: $^{13}$C-NMR (101 MHz, DMSO-$D_6$) δ ppm: 9.9, 30.3, 32.0, 38.0, 44.5, 60.4, 100.9, 106.6, 108.0, 110.1, 117.8, 118.9, 120.2, 121.1, 126.6, 127.3, 127.7, 130.3, 133.9, 137.4, 139.0, 145.8, 147.9

Example No. 22

Step 1

3-(1H-indol-3-yl)methyl propionate 3-indole propionic acid (3.78 g, 20 mmol) was dissolved in methanol (50 ml) in argon. Thionyl chloride (4.7 g, 2.9 ml, 40 mmol) was added very slowly to this solution in drops. During this, the temperature rose to 35° C. The mixture was then heated to reflux for 7 h and stirred overnight at room temperature. Complete conversion was evident in the DC. The LC/MS shows slight traces of a by-product. The batch was concentrated to low volume under the exhaust hood and co-distilled with methanol. The residue was a brown oil, which was thus used for the next reaction step.

Step 2

Dimethyl 3,3'-(2-(4-butyl-4-(dimethylamino)cyclohexan-1,1-diyl)bis(1H-indol-2,3-diyl)dipropanate (Example No. 22)

4-butyl-4-(dimethylamino)cyclohexanone (395 mg, 2 mmol) and 3-(1H-Indol-3-yl)methyl propionate (1.02 g, 5 mmol) were dissolved in dichloromethane (20 ml) in argon. After adding trifluoromethane sulphonic acid (115 µl, 1.3 mmol) the batch was stirred for 4 days at room temperature. The reaction proceeded under LC/MS and DC control. For work up the batch was alkalinised with saturated sodium hydrogencarbonate solution (35 ml) and stirred for 20 min. The phases were separated and the aqueous phase extracted with dichloromethane (2×20 ml). The organic phases were dried and concentrated to low volume. A brown solid (1.51 g) was obtained, which was purified by chromatography [silica gel 50 (50 g); ethyl acetate/methanol 4:1 (1000 ml), ethyl acetate/methanol 1:1 (500 ml), methanol (1000 ml)]. The product was obtained with a yield of 8% (92 mg). It could be purified by recrystallisation from ethyl acetate and cyclohexane (8 ml).

Example No. 22: yield: 42 mg, melting point 199-206° C. $^{13}$C-NMR (101 MHz, $CDCl_3$) δ ppm: 13.7, 19.5, 21.2, 23.2, 25.9, 28.5, 30.7, 31.8, 34.5, 35, 37.2, 42.4, 51.4, 51.6, 111.3, 111.5, 118.1, 118.1, 119.1, 119.5, 121.8, 122.1, 128.7, 128.9, 135.1, 173.5, 173.8

Example No. 23

Step 1

2-(2-(2-(4-butyl-4-(dimethylamino)cyclohex-1-enyl)-1H-indol-3-yl)-ethyl)isoindolin-1,3-dione 2-[2-(1H-indol-3-yl)ethyl]indan-1,3-dione (4.40 g, 15.16 mmol) together with 4-butyl-4-(dimethylamino)cyclohexanone (2.50 g, 12.67 mmol) was mixed with HBr/glacial acetic acid (33% HBr, 15 ml) and stirred for 5 h at 24° C. The mixture was then diluted with dichloromethane (50 ml). 5N sodium hydroxide solution (100 ml) was added with cooling. The batch was stirred for 10 min at room temperature. After separation of the phases the aqueous phase was extracted with dichloromethane (3×20 ml). The combined organic extracts were dried over $Na_2SO_4$ and then concentrated to low volume. The raw product obtained (5.81 g, brown oil) was purified by chromatography [silica gel 60 (110 g); ethyl acetate/methanol (2:1 (1200 ml)]. 1.98 g (33%) of the target compound were obtained (melting point: 125-130° C.).
$^{13}$C NMR (101 MHz, CDCl$_3$) δ ppm: 14.2, 23.6, 24.3, 25.6, 26.6, 28.5, 30.5, 32.3, 38.1, 38.5, 56.0, 107.8, 110.4, 118.5, 119.6, 121.9, 123.1, 126.8, 128.8, 129.1, 132.3, 133.8, 134.93, 136.5, 168.2

Step 2

2-(2-(2-(4-butyl-4-(dimethylamino)-1-(3-methyl-1H-indol-2-yl)cyclohexyl)-1H-indol-3-yl)ethyl)isoindolin-1,3-dione 3-methyl-1H-indole (1.0 g, 7.62 mmol) together with 2-(2-(2-(4-butyl-4-(dimethylamino)cyclohex-1-enyl)-1H-indol-3-yl)-ethyl)isoindolin-1,3-dione (1.20 g, 2.56 mmol) was dissolved in abs. dichloromethane (15 ml) and mixed with trifluoromethane sulphonic acid (0.3 ml, 3.41 mmol). The batch was stirred for 6 d at 24° C. For work up the reaction solution was mixed with 1N NaOH (20 ml). The mixture was stirred for 10 min. After separation of the phases the aqueous phase was extracted with dichloromethane (3×15 ml). The combined organic extracts were dried over $Na_2SO_4$ and then concentrated to low volume. The raw product obtained (brown oil, 2.3 g) was purified by column chromatography [silica gel 60 (100 g); ethyl acetate/methanol 5:1 (600 ml), ethyl acetate/methanol 2:1 (1200 ml)]. The desired bisindole compound was obtained as light yellow solid (505 mg, 33%). According to the NMR spectrum it was a mixture of the two possible diastereoisomers in a ratio of approx. 30:70.
$^{13}$C NMR (101 MHz, CDCl$_3$) δ ppm: 9.6, 10.2, 14.1, 23.8, 24.7, 26.5, 26.6, 29.7, 30.5, 31.6, 31.8, 37.4, 38.3, 38.7, 42.3, 42.7, 56.1, 106.5, 107.4, 108.1, 109.2, 110.6, 110.72, 110.75, 110.9, 117.8, 118.1, 118.2, 118.3, 118.8, 119.0, 119.4, 119.6, 121.0, 121.30, 121.32, 121.7, 123.1, 129.7, 129.8, 130.3 130.4, 132.16, 132.22, 133.8, 134.0, 134.4 134.5, 137.8, 138.7, 140.7, 168.4

Step 3

4-(3-(2-aminoethyl)-1H-indol-2-yl)-1-butyl-N,N-dimethyl-4-(3-methyl-1H-indol-2-yl)cyclohexylamine (Example No. 23, mixture of two diastereoisomers)

2-(2-(2-(4-butyl-4-(dimethylamino)-1-(3-methyl-1H-indol-2-yl)cyclohexyl)-1H-indol-3-yl)ethyl)isoindolin-1,3-dione (450 mg, 0.749 mmol) and hydrazine monohydrate (2 ml, 41.2 mmol) were dissolved in methanol (20 ml) and then boiled with reflux for 45 min. For work up the batch was diluted with 1N NaOH (50 ml) and extracted with diethyl ether (3×20 ml). The combined organic phases were dried over $Na_2SO_4$ and then concentrated until dry. The product was obtained as a light beige-coloured solid with a yield of 302 mg (86%, melting point 105-112° C.). According to the NMR spectrum it was a mixture of the two possible diastereoisomers in a ratio of approx. 30:70.
Example No. 23: $^{13}$C NMR (101 MHz, CDCl$_3$) δ ppm: 9.69, 10.5, 14.0+shoulder, 23.8+shoulder, 26.6, 26.9, 29.0, 29.2, 29.69, 29.75, 30.6, 30.8, 31.6, 31.8, 37.3+shoulder, 42.2, 42.9, 43.0, 56.2, 105.8, 108.1, 108.7, 110.4, 110.59, 110.66, 110.74, 117.9, 118.19, 118.27, 118.5, 118.7, 119.0, 119.14, 119.24, 121.0, 121.2, 121.5+shoulder, 129.78, 129.87, 130.22, 130.36, 134.2, 134.7, 136.4, 137.6, 139.2, 140.0

Example No. 24

Step 1

4-(dimethylamino)-4-(3-fluorophenyl)-1-(thiophen-2-yl)cyclohexanol (more non-polar diastereoisomer and more polar diastereoisomer)

4-(dimethylamino)-4-(3-fluorophenyl)cyclohexanone (2.35 g, 10 mmol) was provided in absolute THF (30 ml) and within 10 min mixed with 2-thienyl magnesium bromide solution (1M in THF, 22.5 ml, 22.5 mmol). The reaction solution was heated to boiling for 2 h with reflux. For work up the solution was carefully mixed with ice pieces and saturated NH$_4$Cl solution (25 ml) with ice bath cooling. The mixture was then extracted with ethyl acetate (3×30 ml). The combined organic phases were washed with water (20 ml) and saturated NaCl solution (20 ml) and dried over sodium sulphate. The volatile constituents were then removed in a vacuum. The chromatographic separation of the substance mixture (3 g) on silica gel 60 (100 g) occurred with ethyl acetate (1000 ml). The more non-polar diastereoisomer was obtained as a beige-coloured compound with a yield of 17% (540 mg). The more polar diastereoisomer could be recovered as beige-coloured compound with a yield of 23% (700 mg).

Step 2

1-(3-fluorophenyl)-N,N-dimethyl-4-(3-methyl-1H-indol-2-yl)-4-thiophen-2-yl-cyclohexylamine (Example No. 24, a diastereoisomer)

3-methyl-1H-indole (344 mg, 2.62 mmol) was provided with the exclusion of moisture together with the more polar 4-(dimethylamino)-4-(3-fluorophenyl)-1-(thiophen-2-yl)cyclohexanol (419 mg, 1.31 mmol, AS 05766) in dry dichloromethane (40 ml) and quickly mixed with trifluoromethane sulphonic acid trimethylsilyl ester (0.38 ml, 1.9 mmol). The batch was stirred 24 h at RT. For work up of the batch the mixture was mixed with 2N sodium hydroxide solution (10 ml) and stirred for 15 min. The aqueous phase was extracted with dichloromethane (2×30 ml). The combined organic phases were concentrated to low volume after drying (Na$_2$SO$_4$), and a brown oil (700 mg) was obtained. After adding methanol (10 ml), a white solid precipitated out, which was aspirated and then dried. One of the two possible diastereoisomers could thus be obtained with a yield of 200 mg (35%) and a melting point of 211-233° C.

Example No. 24: $^{13}$C NMR (101 MHz, CDCl$_3$, δ ppm): 9.9, 30.1, 32.9, 33.7, 37.7, 42.6, 59.9, 104.9, 110.7, 113.0, 113.2, 114.0, 114.3, 117.4, 118.0, 120.4, 122.5, 123.5, 126.3, 129.2, 129.3, 129.5, 134.8, 139.9, 153.2, 161.0, 163.4

Example No. 25 and Example No. 26

Step 1

1-butyl-4,4-bis-(1,3-dimethyl-1H-indol-2-yl)-N,N-dimethylcyclohexylamine and 1-butyl-4-(1,3-dimethyl-1H-indol-2-yl)-N,N-dimethyl-4-(3-methyl-1H-indol-2-yl)cyclohexylamine (one of two possible diastereoisomers)

1-butyl-N,N-dimethyl-4,4-bis-(3-methyl-1H-indol-2-yl) cyclohexylamine (300 mg, 0.679 mmol) was dissolved in abs. dimethylformamide (3 ml) and then mixed with sodium hydride (55-60%, 33 mg, 0.754 mmol). The batch was stirred for 1 h at 24° C. Then at 0° C. methyl iodide (10 mg, 0.704 mmol) dissolved in abs. tetrahydrofuran (1 ml) was added in drops. The batch was stirred for 4 h at 24° C. For work up the reaction mixture was mixed with H$_2$O (15 ml) and extracted with dichloromethane (3×15 ml). The combined organic phases were dried with Na$_2$SO$_4$ and then filtered. The volatile constituents of the filtrate were completely removed in a vacuum. The residue (yellow oil, 372 mg) was purified by column chromatography [silica gel 60 (40 g); cyclohexane/diethyl ether 5:1 (1200 ml), cyclohexane/ethyl acetate 1:1 (600 ml)]. Besides the dimethyl compound (39 mg, colourless oil) the monomethyl compound was obtained as a yellow oil (97 mg, 31%) (one of two possible diastereoisomers).

Step 2

1-butyl-4,4-bis-(1,3-dimethyl-1H-indol-2-yl)-N,N-dimethylcyclohexylamine hydrochloride (Example No. 25)

1-butyl-4,4-bis-(1,3-dimethyl-1H-indol-2-yl)-N,N-dimethylcyclohexylamine (39 mg, 0.083 mmol) was dissolved in cyclohexane (10 ml). The solution was mixed with chlorotrimethyl silane (20 µl, 0.156 mmol) at 24° C. The clear reaction mixture immediately became cloudy. The mixture was stirred for 30 min at 24° C. The white precipitate was aspirated. The solid was washed with cyclohexane (3×0.5 ml) and then dried. The hydrochloride (40 mg, 95%, melting point 153-157° C.) was obtained as a white solid.

Example No. 25: $^{13}$C-NMR (101 MHz, CD$_3$OD, δ ppm, hydrochloride): 12.8, 12.9, 14.2, 24.2, 26.5, 28.5, 31.0, 31.6, 32.3, 33.6, 38.5, 45.5, 68.4, 107.9, 109.8, 109.9, 110.3, 119.1, 119.2, 120.2, 120.3, 123.0, 123.4, 130.3, 130.5, 136.4, 138.7, 139.2, 139.9

Step 3

1-butyl-4-(1,3-dimethyl-1H-indol-2-yl)-N,N-dimethyl-4-(3-methyl-1H-indol-2-yl)cyclohexylamine hydrochloride (Example No. 26)

1-butyl-4-(1,3-dimethyl-1H-indol-2-yl)-N,N-dimethyl-4-(3-methyl-1H-indol-2-yl)cyclohexylamine (97 mg, 0.213 mmol) was dissolved in cyclohexane (10 ml). The solution was mixed with chlorotrimethyl silane (40 µl, 0.313 mmol) at 24° C. The clear reaction mixture immediately became cloudy. The mixture was stirred for 30 min at 24° C. The white precipitate was aspirated. The solid was washed with cyclohexane (3×0.5 ml) and then dried. The hydrochloride (95 mg, 91%, melting point 183-187° C.) was obtained as a white solid.

Example No. 26: $^{13}$C-NMR (101 MHz, CD$_3$OD, δ ppm, hydrochloride): 8.5, 12.4, 14.3, 24.2, 26.7, 28.6, 31.1, 33.2, 38.4, 43.6, 68.6, 108.3, 109.8, 110.4, 111.8, 118.6, 119.2, 119.8, 120.1, 122.3, 123.2, 130.7, 131.2, 136.6, 138.3, 138.3, 140.1

Example No. 27

Step 1

4-benzyl-4-(dimethylamino)-1-(thiophen-2-yl)cyclohexanol (more non-polar diastereoisomer and more polar diastereoisomer)

4-benzyl-4-(dimethylamino)cyclohexanone (2.31 g, 10 mmol) was provided in absolute THF (30 ml) and within 10 min mixed with 2-thienyl magnesium bromide solution (1M in THF, 22.5 ml, 22.5 mmol). The reaction solution was heated to boiling for 2 h with reflux. For work up the solution was carefully mixed with ice pieces and saturated NH$_4$Cl solution (25 ml) with ice bath cooling. The mixture was then extracted with ethyl acetate (3×30 ml). The combined organic phases were washed with water (20 ml) and saturated NaCl solution (20 ml) and dried over sodium sulphate. The volatile constituents were then completely removed in a vacuum. The chromatographic separation of the substance mixture (3 g) on silica gel 60 (100 g) occurred with ethyl acetate/cyclohexane 10:1 (1000 ml). The more non-polar diastereoisomer was obtained as a beige-coloured compound with a yield of 7% (195 mg, AS 05769). No melting point could be determined. The more polar diastereoisomer could be recovered as beige-coloured compound with a yield of 26% (820 mg).

$^{13}$C NMR (101 MHz, DMSO-D$_6$, δ ppm, more non-polar diastereoisomer): 28.2, 34.8, 36.8, 37.1, 57.3, 71.4121.5, 123.4, 125.7, 126.5, 127.9, 130.7, 139.1, 155.4

$^{13}$C NMR (101 MHz, DMSO-D$_6$, δ ppm, more polar diastereoisomer): 28.8, 35.7, 36.6, 37.3, 57.7, 71.7, 122.5, 123.8, 125.8, 127.8, 130.6, 138.7, 152.7

Step 2

1-benzyl-N,N-dimethyl-4-(3-methyl-1H-indol-2-yl)-4-(thiophen-2-yl)cyclohexylamine (Example No. 27, one of two possible diastereoisomers)

3-methyl-1H-indole (414 mg, 3.16 mmol) was provided under exclusion of moisture together with the more polar 4-benzyl-4-(dimethylamino)-1-(thiophen-2-yl)cyclohexanol (500 mg, 1.58 mmol, AS 05770) in dry dichloromethane (40 ml) and quickly mixed with trifluoromethane sulphonic acid trimethylsilyl ester (0.46 ml, 2.37 mmol). The batch was stirred 24 h at RT. For work up of the batch the mixture was mixed with 2N sodium hydroxide solution (10 ml) and stirred for 15 min. The aqueous phase was extracted with dichloromethane (2×30 ml). The combined organic phases were concentrated to low volume after drying (Na$_2$SO$_4$), and a brown oil (750 mg) was obtained. After adding methanol (10 ml), a white solid precipitated out, which was aspirated and then dried. One of the two possible diastereoisomers could thus be obtained with a yield of 260 mg (38%) and a melting point of 119-141° C.

Example No. 27: $^{13}$C NMR (101 MHz, CDCl$_3$, δ ppm): 9.7, 28.3, 31.6, 36.3, 36.8, 41.8, 56.8, 104.0, 110.7, 117.2, 117.9, 120.2, 123.5, 123.7, 125.4, 126.0, 127.5, 129.4, 130.4, 134.2, 138.7, 141.0, 151.0

Example No. 28

Step 1

4-dimethylamino-1-(3-methoxyphenyl)-4-phenylcyclohexanol (more non-polar diastereoisomer and more polar diastereoisomer)

4-(dimethylamino)-4-phenylcyclohexanone (4.34 g, 20 mmol) was dissolved in absolute tetrahydrofuran (60 ml) with the exclusion of oxygen, mixed with 3-methoxyphenyl magnesium bromide solution (45 ml, 45 mmol, 1N) with ice cooling and boiled to reflux for 2 h. For work up the batch was mixed with saturated NH$_4$Cl solution (50 ml) with ice cooling and stirred for 10 min at room temperature. The aqueous phase was separated off and extracted with ethyl acetate (3×25 ml). The combined organic phases were dried over Na$_2$SO$_4$ and then concentrated to low volume. A raw product was isolated that was purified by chromatography [silica gel 60 (50 g); ethyl acetate (1000 ml), methanol (1000 ml)]. 2.5 g (38%, mp 116-117° C.) of more non-polar and 2.78 g (43%, mp 139-140° C.) of more polar product were obtained. Both could be recrystallised from ethyl acetate.

More non-polar diastereoisomer: $^{13}$C-NMR (101 MHz, DMSO-D$_6$) δ ppm: 28.6, 34.0, 37.8, 54.9, 58.0, 70.9, 110.8, 111.1, 117.1, 126.1, 126.5, 127.2, 128.7, 139.4, 152.5, 158.9

More polar diastereoisomer: $^{13}$C-NMR (101 MHz, DMSO-D$_6$) δ ppm: 28.0, 35.5, 37.9, 54.7, 60.7, 70.7, 110.8, 110.9, 116.6, 126.2, 127.5, 127.8, 128.7, 136.5, 151.9, 158.8

Step 2

4-(3-methoxyphenyl)-N,N-dimethyl-4-(3-methyl-1H-indol-2-yl)-1-phenylcyclohexylamine (Example No. 28, one of two diastereoisomers)

3-methyl-1H-indole (393 mg, 3 mmol) and the 4-dimethylamino-1-(3-methoxyphenyl)-4-phenylcyclohexanol (651 mg, 2 mmol) mixture were dissolved in absolute dichloromethane (50 ml) with exclusion of oxygen, mixed with trifluoromethane sulphonic acid (581 µl, 3 mmol) and stirred for 16 h at room temperature. For work up the batch was mixed with 5N NaOH (50 ml) and stirred for 1 h at room temperature. The aqueous phase was separated and extracted with dichloromethane (3×25 ml). The combined organic phases were dried over Na$_2$SO$_4$ and then concentrated to low volume. A raw product was isolated that was purified by chromatography [silica gel 60 (50 g); ethyl acetate (500 ml)]. The product was obtained as a white solid with a yield of 90 mg (10%) and a melting point of 278-281° C. This concerned one of two possible diastereoisomers.

Example No. 28: $^{13}$C-NMR (101 MHz, CDCl$_3$, δ ppm): 10.1, 30.4, 32.3, 38.0, 44.8, 55.0, 60.5, 107.4, 110.1, 110.6, 113.5, 117.5, 117.9, 118.8, 119.2, 121.1, 126.6, 127.1, 127.4, 127.7, 129.2, 130.5, 134.4, 137.1, 138.2, 159.5

Example No. 29

Step 1

N-(2-(2-(4-butyl-4-(dimethylamino)-1-(3-methyl-1H-indol-2-yl)cyclohexyl)-1H-indol-3-yl)ethyl)cyclopentane sulphonamide (Example No. 29, mixture of the two possible diastereoisomers)

4-(3-(2-aminoethyl)-1H-indol-2-yl)-1-butyl-N,N-dimethyl-4-(3-methyl-1H-indol-2-yl)cyclohexylamine (120 mg, 0.255 mmol, mixture of the two possible diastereoisomers in a ratio of approx. 30:70) mixed in dichloromethane (5 ml) with triethylamine (0.12 ml, 0.863 mmol) and cyclopentane sulphonyl chloride (65 mg, 0.385 mmol). After a reaction time of 24 h at 25° C. the reaction mixture was mixed with 1N sodium hydroxide solution (10 ml) and extracted with dichloromethane (3×15 ml). The combined organic phases were dried with Na$_2$SO$_4$ and then filtered. The volatile constituents of the filtrate were completely removed in a vacuum. The residue (yellow foam, 173 mg) was purified by column chromatography [silica gel 60 (25 g); ethyl acetate/methanol 4:1 (250 ml), methanol/30% ammonia 9:1 (100 ml)]. The product was obtained as a beige-coloured solid with a yield of 39 mg (25%) (melting point 111-115° C., AS 11227, mixture of the two possible diastereoisomers in a ratio of approx. 30:70).

Example No. 29: $^{13}$C-NMR (101 MHz, CDCl$_3$, δ ppm): 9.4, 10.35, 10, 39, 13.99, 14.07, 23.7, 25.7+shoulder, 26.5, 26.6, 27.1, 27.9, 28.0, 29.5, 30.6, 31.6, 37.35, 37.4, 41.7, 42.1, 43.0, 43.6, 56.03, 61.4, 61.8, 106.9, 108.5, 110.66, 110.75, 110.91, 110.95, 117.93, 118.03, 118.13, 118.33, 119.15, 119.39, 119.41, 119.79, 121.40 121.48, 121.77, 129.7, 13.2, 134.0, 134.3, 134.5, 138.8, 139.0

Example No. 30

Step 1

1-(3-fluorophenyl)-N,N-dimethyl-4-(3-methyl-1H-indol-2-yl)-4-thiophen-2-ylcyclohexylamine 2-hydroxypropane-1,2,3-tricarboxylic acid (Example No. 30, diastereoisomer mixture)

For production of the citrate the diastereoisomer mixture of 1-(3-fluorophenyl)-N,N-dimethyl-4-(3-methyl-1H-indol-2-yl)-4-thiophen-2-ylcyclohexylamine (280 mg, 0.64 mmol, AS 05768) was dissolved in hot isopropanol (80 ml) and mixed with a likewise hot isopropanol citric acid solution (187 mg, 0.97 mmol in 3 ml). The reaction mixture was then stored for 16 h in the refrigerator. The solid obtained was aspirated. The citrate was thus obtained as white solid with a yield of 60 mg (14%) (melting point: 99-117° C.).

Example No. 30: $^{13}$C-NMR (101 MHz, DMSO-d$_6$) δ ppm: 9.9, 10.0, 29.3, 32.9, 34.0, 37.5, 37.6, 42.5, 43.4, 45.4, 71.8, 104.9, 110.7, 114.4, 117.4, 117.6, 118.0, 120.5, 120.7, 123.6, 123.8, 126.4, 126.6, 129.3, 129.6, 134.5, 135.0, 160.9, 163.4, 171.2, 175.5

Example No. 31

Step 1

N,N-dimethyl-1-phenyl-4,4-bis-(3-(2-pyridin-4-yl) ethyl)-1H-indol-2-yl)cyclohexylamine (Example No. 31)

3-(2-pyridin-4-ylethyl)-1H-indole (667 mg, 3 mmol, synthesis cf. WO2008009415, indole unit Ind-14) (1.02 g, 4.6 mmol) and 4-(dimethylamino)-4-phenylcyclohexanone (1.0 g, 4.6 mmol) were dissolved in abs. dichloromethane (80 ml) and mixed with trifluoromethane sulphonic acid (1.07 ml, 1.72 g, 11.5 mmol). After a reaction time of 4 d at room temperature, the dark brown reaction mixture was mixed with water (30 ml), 1N sodium hydroxide solution (20 ml) and tetrahydrofuran (20 ml) and stirred for 2.5 h. The phases were separated. The aqueous phase was extracted with dichloromethane (30 ml). The combined organic phases were washed with water (30 ml), dried with sodium sulphate and concentrated to low volume. The raw product obtained (dark brown oil, 2.08 g) was separated by chromatography [silica gel 60 (150 g); ethyl acetate/methanol 15:1 (1800 ml), ethyl acetate/methanol 6:1 (600 ml), ethyl acetate/methanol 1:1 (1200 ml)]. The bisindole compound was isolated as slightly impure beige-coloured solid with a yield of 82 mg. To purify the bisindole compound the solid was recrystallised from methanol (1.5 ml) (55 mg, 1.9%, melting point: 305-310° C.).

Example No. 31: $^{13}$C-NMR (101 MHz, DMSO-D$_6$, δ ppm): 26.5, 30.1, 31.6, 34.8, 37.7, 40.0, 59.1, 109.3, 109.4, 111.3, 117.5, 118.3, 120.0, 120.1, 123.7, 126.2, 127.0, 127.4, 128.4, 128.5, 134.4, 134.6, 137.7, 140.0, 149.0, 149.2, 150.6

Example No. 32

Step 1

1-(2-(2-(4-butyl-4-(dimethylamino)-1-(3-methyl-1H-indol-2-yl)cyclohexyl)-1H-indol-3-yl)ethyl)-3-phenylurea (Example No. 32, mixture of the two possible diastereoisomers)

4-(3-(2-aminoethyl)-1H-indol-2-yl)-1-butyl-N,N-dimethyl-4-(3-methyl-1H-indol-2-yl)cyclohexylamine (120 mg, 0.255 mmol, mixture of the two possible diastereoisomers in a ratio of approx. 30:70) was mixed in acetonitrile (2.4 ml) with phenyl isocyanate (0.042 ml, 0.386 mmol). After a reaction time of 2 h at 24° C. the reaction mixture was diluted with 1N sodium hydroxide solution (20 ml) and extracted with dichloromethane (4×10 ml). The combined organic phases were dried with Na$_2$SO$_4$ and then filtered. The volatile constituents of the filtrate were completely removed in a vacuum. The residue (yellow solid, 150 mg) was purified by column chromatography [silica gel 60 (25 g); cyclohexane/ethyl acetate 2:1 (300 ml), ethyl acetate/methanol 1:1 (300 ml]. The product was obtained as a white solid with a yield of 115 mg (76%) (melting point 115-120° C., mixture of the two possible diastereoisomers in a ratio of approx. 25:75).

Example No. 32: $^{13}$C-NMR (101 MHz, CDCl$_3$, δ ppm): 9.4, 10.3, 14.1, 22.6, 23.7, 25.2, 25.9, 26.5, 26.6, 29.5, 29.7, 30.5, 31.52, 31.56, 31.65, 37.36, 37.39, 40.5, 41.0, 42.1, 42.2, 56.0, 106.6, 108.1, 110.2, 110.9, 118.0, 118.6, 119.2, 111.31, 119.36, 119.6, 120.4, 120.2, 121.3, 121.5, 123.2, 123.4, 128.9, 129.0, 129.6, 129.7, 130.1, 131.2, 134.0, 134.5, 134.6, 137.8, 138.56, 138.61, 139.7, 140.8, 155.5, 155.8

Example No. 33

Step 1

2,2'-(2,2'-(2,2'-(4-butyl-4-(dimethylamino)cyclohexan-1,1-diyl)bis(-1H-indol-3,2-diyl))bis(ethan-2,1-diyl)diisoindol-1,3-dione 2-(2-(2-(4-butyl-4-dimethylaminocyclohex-1-enyl)-1H-indol-3-yl)-ethyl)isoindol-1,3-dione (658 mg, 1.4 mmol) and 2-(2-1H-indol-3-yl)ethyl)isoindolin-1,3-dione (934 mg, 3.22 mmol) were dissolved in abs. dichloromethane (60 ml) and mixed with trifluoromethane sulphonic acid (0.226 ml, 362 mg, 2.41 mmol). After a reaction time of 17 d at room temperature, the dark brown reaction mixture was mixed with water (30 ml) and 1N sodium hydroxide solution (10 ml) and stirred for 2 h. The phases were separated. The aqueous phase was extracted with dichloromethane (30 ml). The combined organic phases were dried with sodium sulphate and concentrated to low volume. The raw product obtained (yellow solid, 1.61 g) was separated by chromatography [silica gel 60 (120 g); ethyl acetate/methanol 15:1 (1200 ml), ethyl acetate/methanol 1:1 (900 ml)]. The bisindole compound was isolated as a yellow solid with a yield of 53% (563 mg) with a melting point of 170-172° C. (AS 04735).

Step 2

2,2'-(2,2'-(4-butyl-4(dimethylamino)cyclohexan-1,1-diyl)bis(1H-indol-3,2-diyl)diethylamine 2,2'-(2,2'-(2,2'-(4-butyl-4-(dimethylamino)cyclohexan-1,1-diyl)bis(-1H-indol-3,2-diyl))bis(ethan-2,1-diyl)diisoindol-1,3-dione (531 mg, 0.7 mmol) was suspended in methanol (40 ml) and mixed with hydrazine hydrate (3.4 ml, 3.5 g, 70 mmol). Upon heating a clear light-coloured solution was formed that was heated for 1.5 h with reflux. The reaction mixture was cooled, mixed with 1N sodium hydroxide solution (70 ml) and methanol and hydrazine removed in a vacuum. The aqueous residue was extracted with diethyl ether (3×50 ml). The organic phase was washed with water (30 ml), dried over sodium sulphate and concentrated to low volume. The residue was a yellow solid (394 mg, quantitative).

$^{13}$C-NMR (101 MHz, CDCl$_3$, δ ppm): 14.0, 23.7, 26.4, 28.0, 28.2, 29.4, 31.50, 31.57, 37.3, 42.0, 42.3, 44.1, 56.1, 104.0, 110.3, 110.5, 118.1, 118.2, 118.3, 118.5, 120.9, 121.2, 129.2, 129.3, 135.1, 135.5, 138.8, 141.0

Step 3

1,1'-(2,2'-(2,2'-(4-butyl-4(dimethylamino)cyclohexan-1,1-diyl)bis(1H-indol-3,2-diyl))bis(ethan-2,1-diyl)bis(3-phenylurea) (Example No. 33)

2,2'-(2,2'-(4-butyl-4(dimethylamino)cyclohexan-1,1-diyl) bis(1H-indol-3,2-diyl)diethylamine (120 mg, 0.24 mmol) was dissolved in abs. acetonitrile (25 ml) and mixed in drops with phenyl isocyanate (0.063 ml, 69 mg, 0.58 mmol). After a reaction time of 5 h at room temperature the clear light-coloured solution was concentrated to low volume. The raw product obtained (yellow solid, 175 mg) was separated by chromatography [silica gel 60 (30 g), ethyl acetate/methanol 4:1 (300 ml)]. The urea was obtained as beige-coloured solid with a yield of 54% (96 mg).

Example No. 33: $^{13}$C-NMR (101 MHz, DMSO-D$_6$, δ ppm): 13.8, 22.8, 25.0, 25.6, 30.3, 31.1, 34.3, 37.3, 40.7, 66.9, 107.9, 111.1, 117.6, 117.9, 118.3, 120.4, 120.8, 127.9, 128.5, 129.1, 134.6, 139.1, 140.5, 155.2

Example No. 34

Step 1

1-butyl-4,4-bis(5-fluoro-3-methyl-1H-indol-2-yl)-N,N-dimethylcyclohexylamine (Example No. 34)

5-fluoroskatole (670 mg, 4.49 mmol) together with 2-(2-(2-(4-butyl-4-dimethylaminocyclohex-1-enyl)-1H-indol-3-yl)-ethyl)isoindol-1,3-dione (700 mg, 1.49 mmol) was dissolved in abs. dichloromethane (5 ml) and mixed with trifluoromethane sulphonic acid (0.175 ml, 1.974 mmol). The batch was stirred for 10 d at 24° C. The precipitated light beige-coloured solid was separated by filtration and washed with dichloromethane (3×0.5 ml). The solid (1031 mg) was stirred for 10 min with 1N sodium hydroxide solution (20 ml) and dichloromethane (20 ml). The phases were separated. The aqueous phase was extracted with dichloromethane (2×20 ml). The combined organic extracts were dried over Na₂SO₄ and then concentrated to low volume. The product was purified by column chromatography.

Example No. 34: 91 mg, 12% white solid, melting point: 181-186° C.

$^{13}$C-NMR (101 MHz, CDCl₃, δ ppm): 9.28, 10.32, 14.14, 23.74, 26.58, 29.79, 31.56, 37.30, 42.55, 55.98, 102.75, 102.98, 103.11, 103.33, 106.79, 108.61, 108.65, 109.16, 109.42, 109.70, 109.96, 110.91, 111.02, 111.15, 111.24, 130.26, 130.67, 130.75, 130.83, 139.94, 131.03, 138.30, 140.72, 156.58, 156.74, 158.91, 159.08

795 mg (approx. 60%) as yellow solid, melting point: 103-108° C.

$^{13}$C-NMR (101 MHz, CDCl₃, δ ppm, as mixture): 9.6, 14.1, 16.4, 23.7, 24.6, 26.6, 29.9, 30.2, 31.6, 31.7, 37.3, 38.3, 42.6, 42.8, 45.5, 56.0, 64.8, 102.5, 102.8, 103.3, 103.6, 106.45, 106.49, 106.73, 106.77, 109.0, 109.17, 109.23, 109.42, 109.56, 109.69, 109.74, 109.94, 110.20, 110.75, 110.91, 111.00, 111.16, 111.26, 111.35, 113.56, 113.79, 118.3, 119.6, 121.9, 123.1, 129.6, 130.24, 130.37, 130.74, 13.84, 130.94, 131.7, 132.1, 133.9, 134.4, 136.3, 137.3, 140.7, 141.1, 145.7, 156.53, 156.56, 158.85, 158.88, 168.4

Example No. 35

Step 1

4-(3-(2-aminoethyl)-1H-indol-2-yl)-1-butyl-4-(5-fluoro-3-methyl-1H-indol-2-yl)-N,N-cyclohexylamine (Example No. 35, a diastereomer)

? (710 mg, approx. 0.7 mmol) and hydrazine hydrate (2 ml, 41.2 mmol) were dissolved in methanol (20 ml) and then boiled with reflux for 2 h. For work up the batch was diluted with 1N NaOH (50 ml) and extracted with dichloromethane (4×15 ml). The combined organic phases were dried over Na₂SO₄ and then concentrated until dry. The raw product obtained (white solid, 583 mg) was purified by column chromatography [silica gel 60 (20 g); cyclohexane/ethyl acetate 4:1 (250 ml); ethyl acetate (500 ml), methanol/30% ammonia 9:1 (250 ml)]. One of two possible diastereoisomers (343 mg, approx. 80%, mp 145-150° C.) was recovered as white solid.

Example No. 35: $^{13}$C-NMR (101 MHz, CD₃OD, δ ppm): 9.46, 14.46, 24.72, 27.50, 29.52, 29.86, 32.10, 32.29, 37.99, 42.45, 42.72, 57.98, 102.88, 103.12, 107.84, 109.38, 109.65, 109.89, 111.98, 112.29, 112.39, 118.77, 119.69, 121.77, 130.83, 132.63, 131.72, 132.57, 136.33, 140.47, 142.57, 157.83, 160.13

Example No. 36 and Example No. 37

Step 1

N,N-dimethyl-1-phenyl-4-(3-(2-pyridin-4-yl)ethyl)-1H-indol-2-yl)cyclohex-3-enamine 3-(2-pyridin-4-ylethyl)-1H-indole (667 mg, 3 mmol, synthesis cf. WO2008009415, indole unit Ind-14) together with 4-(dimethylamino)-4-phenylcyclohexanone (652 mg, 3 mmol) was dissolved in abs. dichloromethane (45 ml) and mixed with trifluoromethane sulphonic acid (0.553 ml, 6.3 mmol). The batch was stirred for 64 h at RT, and a brown oil separated out. For work up the reaction solution was mixed with 1N NaOH (10 ml) and THF (10 ml). The mixture was stirred a further 60 min. After separation of the phases the aqueous phase was extracted with dichloromethane (3×10 ml). The combined organic extracts were dried over Na₂SO₄ and then concentrated to low volume. The raw product obtained (1.34 g) was purified by column chromatography [silica gel 60 (100 g); ethyl acetate/methanol (20:1, 500 ml), ethyl acetate/methanol (5:1, 870 ml), ethyl acetate/methanol (2:1, 320 ml), ethyl acetate/methanol (1:2, 550 ml)]. The compound was obtained as a colourless solid (339 mg, 27%, mp: 193-198° C.).

Step 2

N,N-dimethyl-4-(3-methyl-1H-indol-2-yl)-1-phenyl-4-(3-(2-pyridin-4-yl)ethyl)-1H-indol-2-yl)cyclohexylamine (Example No. 36, polar diastereomer and Example No. 37, non-polar diastereomer)

N,N-dimethyl-1-phenyl-4-(3-(2-pyridin-4-yl)ethyl)-1H-indol-2-yl)cyclohex-3-enamine (840 mg, 1.99 mmol) and 3-methyl-1H-indole (651 mg, 4.97 mmol) were dissolved in abs. dichloromethane (90 ml) and mixed with trifluoromethane sulphonic acid (0.373 ml, 597 mg, 3.98 mmol). After a reaction time of 20 d at room temperature, the dark brown reaction mixture was mixed with water (30 ml) and 1N sodium hydroxide solution (5 ml) and stirred for 1 h. The phases were separated. The aqueous phase was extracted with dichloromethane (30 ml). The combined organic phases were dried with sodium sulphate and concentrated to low volume. The raw product obtained (brown oil, 1.39 g) was separated by chromatography [silica gel 60 (110 g); ethyl acetate/cyclohexane 4:1 (1000 ml), ethyl acetate (600 ml), ethyl acetate/methanol 4:1 (1000 ml)]. The non-polar bisindole compound was obtained as a yellow solid with a yield of 39% (423 mg). The solid was taken up in ethanol (4 ml) and heated to 80° C. for 30 min. After filtration of the remaining solid, the more non-polar bisindole was obtained as a colourless solid with a yield of 20% (220 mg) and with a melting point of 273-276° C. The more polar bisindole was recovered as slightly impure beige-coloured solid with a yield of 7% (74 mg) and a melting point of 230-235° C.

Example No. 36: $^{13}$C-NMR (101 MHz, DMSO-D₆, δ ppm, more polar diastereoisomer): 9.2, 26.3, 29.9, 31.4, 34.8, 37.7, 105.3, 109.1, 111.1, 111.2, 117.3, 118.2, 120.1, 123.6, 127.6, 128.5, 129.5, 134.3, 140.4, 149.0, 150.5

Example No. 37: $^{13}$C-NMR (101 MHz, DMSO-D₆, δ ppm, more non-polar diastereoisomer): 9.3, 26.4, 29.9, 31.0, 34.9, 37.7, 105.4, 109.1, 111.0, 111.3, 117.1, 117.4, 118.1, 118.2, 120.0, 120.1, 123.6, 126.9, 127.5, 128.6, 129.4, 134.3, 134.5, 138.9, 149.0, 150.6, Example No. 38

Step 1

(phenyl-2-(2-(4-butyl-4-(dimethylamino)-1-(5-fluoro-3-methyl-1H-indol-2-yl)cyclohexyl)-1H-indol-3-yl)ethyl carbamate (Example No. 38, one of two possible diastereoisomers)

4-(3-(2-aminoethyl)-1H-indol-2-yl)-1-butyl-4-(5-fluoro-3-methyl-1H-indol-2-yl)-N,N-cyclohexylamine (Example No. 35) (120 mg, 0.246 mmol, one of two possible diastereoisomers) was mixed in dichloromethane (5 ml) with phenyl chloroformate (0.045 ml, 0.359 mmol). After a reaction time of 5 h at 24° C., the reaction mixture was diluted with dichloromethane (20 ml) and washed with 1N sodium hydroxide solution (4×10 ml). The organic phase was dried with Na₂SO₄ and then filtered. The volatile constituents of the filtrate were completely removed in a vacuum. The residue (colourless oil, 172 mg) was suspended in n-hexane (5 ml). The batch was stirred for 2 h at 24° C. The crystalline product was filtered, washed with n-hexane (2×0.5 ml) and dried. The carbamate was obtained as a white solid with a yield of 111 mg (74%) (melting point 101-105° C., one of two possible diastereoisomers).

Example No. 38: $^{13}$C-NMR (101 MHz, CDCl$_3$, δ ppm): 8.8, 13.9, 23.1, 25.3, 26.1, 29.1, 30.1, 31.2, 37.2, 40.9, 41.3, 55.35, 101.7, 101.9, 105.1, 107.9, 111.2 111.79, 111.89, 117.6, 118.2, 120.3, 121.2, 121.7, 124.8, 129.1, 129.2, 129.5, 129.8, 129.9, 130.8, 134.7, 138.3, 142.8, 151.0, 154.2, 155.5, 157.8

Example No. 39

Step 1

1-(2-(2-(4-butyl-4-(dimethylamino)-1-(5-fluoro-3-methyl-1H-indol-2-yl)cyclohexyl)-1H-indol-3-yl) ethyl)-3-phenylurea (Example No. 39, one of two possible diastereoisomers)

4-(3-(2-aminoethyl)-1H-indol-2-yl)-1-butyl-4-(5-fluoro-3-methyl-1H-indol-2-yl)-N,N-cyclohexylamine (Example No. 35) (120 mg, 0.246 mmol, one of two possible diastereoisomers) mixed in acetonitrile (2.4 ml) with phenyl isocyanate (0.040 ml, 0.368 mmol). After a reaction time of 5 h at 23° C., the reaction mixture was diluted with 1N sodium hydroxide solution (15 ml) and extracted with dichloromethane (4×10 ml). The combined organic phases were dried with Na$_2$SO$_4$ and then filtered. The volatile constituents of the filtrate were completely removed in a vacuum. The residue (colourless oil, 160 mg) was purified by column chromatography [silica gel 60 (20 g); cyclohexane/ethyl acetate 2:1 (300 ml), ethyl acetate/methanol 1:1 (300 ml)]. The product was obtained as a white solid with a yield of 117 mg (78%) (melting point 127-132° C., one of two possible diastereoisomers).

Example No. 39: $^{13}$C-NMR (101 MHz, CDCl$_3$, δ ppm): 9.5, 14.0, 23.7, 26.0, 26.5, 29.5, 30.3, 31.6, 37.3, 40.6, 42.3, 56.0, 102.7, 102.9, 106.7, 109.4, 109.6, 110.1, 110.9, 111.4, 111.5, 118.5, 119.7, 120.8, 121.8, 123.6, 129.0, 129.6, 130.4, 130.6, 134.5, 137.5, 138.4, 141.6, 155.6, 156.6, 159.0

Example No. 40

Step 1

N,N-dimethyl-1-phenyl-4-(3-(2-(pyridin-4-yl)-ethyl)-1H-indol-2-yl)-4-(thiophen-2-yl)cyclohexylamine (Example No. 40, diastereoisomer mixture)

3-(2-pyridin-4-ylethyl)-1H-indole (synthesis cf. WO2008009415, indole unit Ind-14) (444 mg, 2 mmol) together with the more polar 4-(dimethylamino)-4-phenyl-1-(thiophen-2-yl)cyclohexanol (444 mg, 1 mmol, AS 05710) was provided in dry dichloromethane (30 ml) with the exclusion of moisture and quickly mixed with trifluoromethane sulphonic acid trimethylsilyl ester (0.54 ml, 3 mmol). The batch was stirred 24 h at RT. For work up of the batch the mixture was mixed with 2N sodium hydroxide solution (10 ml) and stirred for 15 min. The aqueous phase was extracted with dichloromethane (2×30 ml). The combined organic phases were concentrated to low volume after drying (Na$_2$SO$_4$), and a brown oil (560 mg) was obtained. After chromatographic purification of the residue on silica gel 60 (50 g) with ethyl acetate/cyclohexane 1:1 (700 ml), the diastereoisomer mixture could be obtained as solid with a yield of 95 mg (19%) (melting point: 54-60° C.).

Example No. 40: $^{13}$C NMR (101 MHz, CDCl$_3$, δ ppm): 26.0, 26.3, 29.7, 30.1, 32.8, 33.8, 35.6, 36.3, 37.3, 37.938.1, 38.3, 43.4, 59.6, 61.5, 110.7, 112.8, 113.4, 118.0, 1187, 118.7, 119.2, 121.0, 121.5, 123.9, 124.0, 126.5, 126.6, 126.8, 126.9, 127.0, 127.2, 127.1, 127.6, 127.8, 127.9, 129.2, 129.4, 135.4, 149.5, 149.6, 151.1, 151.5

Studies on the Efficacy of the Compounds According to the Invention

Measurement of the ORL 1-bond

The compounds were examined with membranes of recombinant CHO—ORL 1 cells in a receptor binding assay with $^3$H-nociceptin/orphanin FQ. This test system was conducted in accordance with the method outlined by Ardati et al. (Mol. Pharmacol., 51, 1997, pp. 816-824). The concentration of $^3$H-nociceptin/orphanin FQ amounted to 0.5 nM in these tests. The binding assays were conducted in each case on 20 µg of membrane protein per 200 µl of preparation in 50 mM of HEPES, pH 7.4, 10 nM of MgCl$_2$ and 1 mM of EDTA. The binding to the ORL 1-receptor was determined using 1 mg of WGA-SPA beads (Amersham-Pharmacia, Freiburg) in each case by incubating the preparation for one hour at RT and then conducting measurements in the Trilux scintillation counter (Wallac, Finland). The affinity is indicated as nanomolar K$_i$ value or in % inhibition at c=1 µM in Table 1.

Measurement of the µ-Bond

The affinity to the human µ-opiate receptor was determined in a homogeneous preparation in microtiter plates. For this, dilution series of the respective compound to be tested were incubated for 90 minutes at room temperature with a receptor membrane preparation (15-40 µg of protein per 250 µl of incubation batch) of CHO-K1 cells, which express the human µ-opiate receptor (RB-HOM receptor membrane preparation of NEN, Zaventem, Belgium), in the presence of 1 nmol/l of the radioactive ligand [$^3$H'-naloxone (NET719, NEN, Zaventem, Belgium) and of 1 mg WGA-SPA beads (wheat germ agglutinin SPA beads from Amersham/Pharmacia, Freiburg, Germany) in a total volume of 250 µl. 50 mmol/l of tris-HCl supplemented by 0.05% by wt. of sodium azide and 0.06% by wt. of bovine serum albumin was used as incubation buffer. 25 µmol/l of naloxone were additionally added to determine the non-specific bond. After the ninety-minute incubation time had ended, the microtiter plates were centrifuged for 20 minutes at 1000 g and the radioactivity measured in a β-counter (Microbeta-Trilux, PerkinElmer Wallac, Freiburg, Germany). The percentage displacement of the radioactive ligand from its binding to the human µ-opiate receptor was determined with a concentration of the test substances of 1 µmol/l and was specified as percentage inhibition (% inhibition) of the specific bond. In some instances, working from the percentage displacement by different concentrations of the compounds of the general formula I according to the invention, IC$_{50}$ inhibition concentrations were calculated that effect a 50 percent displacement of the radioactive ligand. Ki values for the test substances were obtained by conversion using the Cheng-Prusoff equation. In some cases, the determination of the Ki value was omitted and only the inhibition with a test concentration of 1 µM was determined.

Measurement of the Kappa-Bond

The determination occurs in a homogeneous batch in microtiter plates. For this, dilution series of the respective substances to be tested were incubated for 90 minutes at room temperature with a receptor membrane preparation (7 µg of protein per 250 µl of incubation batch) of CHO-K1 cells, which express the human µ-opiate receptor, in the presence of 1 nmol/l of the radioactive ligand [$^3$H']-Cl-977 and 1 mg WGA-SPA beads (wheat germ agglutinin SPA beads from Amersham/Pharmacia, Freiburg, Germany) in a total volume of 250 μl. 50 mmol/l of tris-HCl supplemented by 0.05% by wt. of sodium azide and 0.06% by wt. of bovine serum albumin was used as incubation buffer. 100 μmol/l of naloxone were additionally added to determine the non-specific bond. After the ninety-minute incubation time had ended, the microtiter plates were centrifuged for 20 minutes at 500 rpm and the radioactivity measured in a β-counter (Microbeta-Trilux 1450, PerkinElmer Wallac, Freiburg, Germany). The percentage displacement of the radioactive ligand from its binding to the human μ-opiate receptor was determined with a concentration of the test substances of 1 μmol/l and was specified as percentage inhibition (% inhibition) of the specific bond. Working from the percentage displacement by different concentrations of the compounds to be tested, IC$_{50}$ inhibition concentrations can be calculated that effect a 50 percent displacement of the radioactive ligand. Ki values for the test substances can be calculated by conversion using the Cheng-Prusoff equation.

Analgesia Testing in the Tail Flick Test in Rats

The analgesic efficacy of the test compounds was examined in the hot beam (tail flick) test in rats using the method of D'Amour and Smith (J. Pharm. Exp. Ther. 72, 74, 79 (1941)). Female Sprague Dawley rats with a weight of between 130 and 190 g were used for this. The animals were placed individually into special test cages and the base of the tail subjected to a focussed hot beam from a lamp (tail flick type 50/08/1.bc, Labtec, Dr. Hess). The lamp intensity was adjusted so that the time from switching on the lamp to the sudden flicking away of the tail (pain latency) amounted to 2.5-5 seconds in untreated animals. Before being given a test compound, the animals were pre-tested twice within 30 minutes and the mean value of these measurements calculated as pre-test mean. The pain measurement was conducted 20, 40 and 60 min after intravenous administration. The analgesic effect was determined as increase in pain latency (% MPE) according to the following formula: $[(T_1-T_0)/(T_2-T_0)] \times 100$. In this case, $T_0$ is the latency time before and $T_1$ the latency time after substance application, $T_2$ is the maximum exposure time (12 sec).

To determine the dose dependency, the respective test compound was applied in 3-5 logarithmically increasing doses, which respectively include the threshold dose and maximum effective dose, and the ED$_{50}$ values determined by means of regression analysis. The ED$_{50}$ calculation occurred in the effect maximum, 20 minutes after intravenous substance application.

Nephelometric Solubility Study (Phosphate Buffer pH 7.4):

This method examines the solubility of a substance with fixed concentrations (1 μM, 3 μM, 10 μM, 30 μM and 100 μM) in 10 mM of phosphate buffer solution with pH 7.4. A 10 mM solution of the substances in DMSO will be initially required, from which 100-fold stock solutions of the above-mentioned concentration level again in DMSO are produced, the final DMSO concentration in the test batch amounting to 1% (v/v). The experiment is conducted multiple times for determination. After the DMSO stock solutions have been added to the buffer, the batch is incubated for 2 h at 37° C. before an absorption determination at 620 nm occurs. If the absorption of the samples increases above that of the pure buffer/DMSO solution, then this applies as indicator for a precipitate formation. The lower solubility limit ("lower boundary") is the concentration preceding that with the first precipitate formation (e.g. 3 μM if precipitation formation was detected at 10 μM).

The results are collated in the following table:

| No. | % Inhibition (ORL1) [1 μM] | Ki (ORL1) Mean [μM] | % Inhibition (μ) [1 μM] | Ki (μ) Mean [μM] | Tail flick Rat, i.v |
|---|---|---|---|---|---|
| 1 | 9 | 1.333 | 60 | 0.557 | nd |
| 2 | 89 | 0.167 | 92 | 0.097 | nd |
| 3 | 19 | 0.730 | 96 | 0.010 | nd |
| 4 | 93 | 0.029 | 73 | 0.143 | nd |
| 5 | 18 | 1.077 | 77 | 0.093 | nd |
| 6 | 70 | nd | 80 | nd | nd |
| 7 | 89 | 0.009 | 83 | 0.042 | 30% MPE at 100 μg/kg |
| 8 | 31 | 0.460 | 46 | 0.590 | nd |
| 9 | 82 | 0.020 | 76 | 0.150 | nd |
| 10 | 8 | 0.283 | 3 | 0.780 | nd |
| 11 | 77 | 0.043 | 83.5 | 0.06 | nd |
| 12 | 95 | 0.013 | 100 | 0.005 | nd |
| 13 | 96 | 0.027 | 103 | 0.0009 | nd |
| 14 | 98 | 0.001 | 96 | 0.0005 | nd |
| 15 | 96 | 0.007 | 99 | 0.006 | nd |
| 16 | 84 | 0.027 | 97 | 0.011 | nd |
| 17 | 99 | nd | 99 | nd | nd |
| 18 | 80 | 0.039 | 74 | 0.078 | nd |
| 19 | 88 | 0.023 | nd | 0.022 | nd |
| 20 | 87 | 0.029 | nd | 0.012 | nd |
| 21 | 56 | 0.265 | nd | 0.47 | nd |
| 22 | 93 | 0.011 | nd | 0.003 | nd |
| 23 | 98 | 0.001 | nd | 0.001 | nd |
| 24 | 86 | nd | nd | nd | nd |
| 25 | 31 | 0.45 | nd | 0.081 | nd |
| 26 | 30 | 0.61 | nd | 0.165 | nd |
| 27 | 72 | nd | nd | nd | nd |
| 28 | 82 | nd | nd | nd | nd |
| 29 | 97 | nd | nd | nd | nd |
| 31 | 71 | 0.088 | nd | 0.028 | nd |
| 32 | 98 | 0.013 | 100 | 0.0043 | nd |
| 33 | 97 | 0.012 | 100 | 0.011 | nd |
| 34 | 56 | 0.119 | 76 | 0.21 | nd |
| 35 | 95 | nd | 98 | nd | nd |
| 36 | 61 | nd | 73 | nd | nd |
| 37 | 94 | 0.018 | 97 | 0.061 | nd |
| 38 | 83 | nd | 90 | nd | nd |
| 39 | 86 | 0.031 | 95 | 0.029 | nd |
| 40 | 82 | 0.021 | 69 | 0.717 | nd |

The compounds according to the invention with Q=(hetero-)aryl of type E were compared with the otherwise accordingly substituted compounds of type E, in which Q=H:

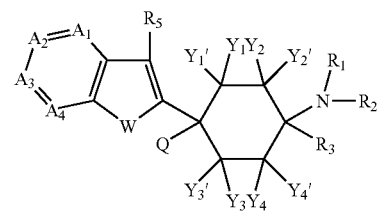

E

The results are collated in the following tables:

| Nr. | Q | Ki (μ)/ Ki (ORL1) | Ki (kappa)/ Ki (ORL1) | Ki (ORL1) Mean [μM] | Ki (μ) Mean [μM] | Ki (kappa) Mean [μM] |
|---|---|---|---|---|---|---|
| Ex. 4 | 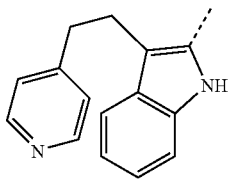 | 4.9 | 5.5 | 0.029 | 0.143 | 0.160 |
| Comparison 1: Ex. No. 304 in WO2008009415 | —H— | 1.2 | 1.0 | 0.153 | 0.197 | 0.153 |
| Ex. 7 | 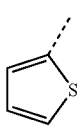 | 4.7 | 15.2 | 0.009 | 0.042 | 0.137 |
| Comparison 2: Ex. No. 17 in WO2008009415 | —H— | 0.4 | 1.7 | 0.0009 | 0.0004 | 0.0012 |
| Comparison 3: Ex. No. 18 in WO2008009415 | —H— | 0.9 | — | 0.0140 | 0.0130 | n.d.* |
| Ex. 9 | 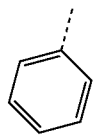 | 7.5 | 29 | 0.020 | 0.150 | 0.580 |
| Comparison 4: Ex. No. 17 in WO2008009415 | —H— | 0.4 | 1.7 | 0.0009 | 0.0004 | 0.0012 |
| Comparison 5: Ex. No. 18 in WO2008009415 | —H— | 0.9 | — | 0.0140 | 0.0130 | n.d.* |
| Ex. 10 | 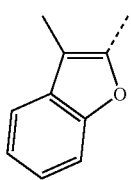 | 2.8 | — | 0.283 | 0.780 | 4% Inhibition at [1 μM] |
| Comparison 6 Ex. No. 226 in WO2008009415 | —H— | 0.1 | — | 0.039 | 0.005 | 31% Inhibition at [1 μM] | n.d. = not determined

As the above comparison data show, the compounds according to the invention (Q=aryl/heteroaryl) have a higher selectivity with respect to the kappa-opioid receptor (defined as $1/[K_{i(ORL1)}/K_{i(kappa)}]$) compared to the structurally similar substances (Q=—H). Moreover, with a favourable ORL 1/μ affinity ratio, the substances according to the invention also have a higher selectivity with respect to the μ-opioid receptor (defined as $1/[K_{i(ORL1)}/K_{i(\mu)}]$).

The compounds according to the invention of type 1 with Q=thienyl (Ex. 7) were compared with corresponding compounds of type 1 with Q=H(C-7 to C-9):

| Ex. | Q | (Hetero-)aryl | $R_1$ | Nephelometry (lower boundary) μM |
|---|---|---|---|---|
| 7 | 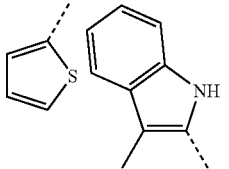 | 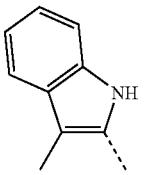 | Me | 10 |
| Comparison 2: Ex. No. 17 in WO2008009415 | H | 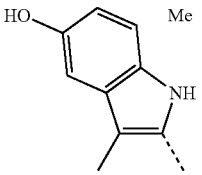 | Me | 1 |
| Comparison 7: Ex. No. 118 in WO2008009415 | H | 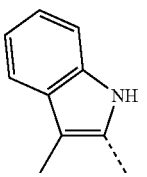 | Me | <1 |
| Comparison 8: Ex. No. 259 in WO2008009415 | H | 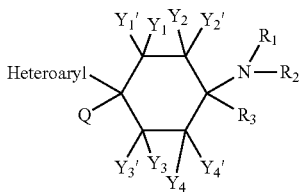 | H | 3 |

As the above comparison shows, the compound from Example 7 according to the invention has a better solubility in aqueous media compared to structurally similar compounds (Q=H), which in particular should be associated with advantages with respect to the resorption properties and/or bioavailability.

The invention claimed is:
1. A compound of the formula:

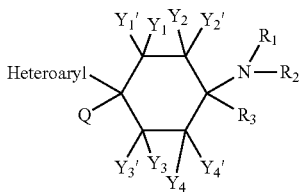

wherein
$Y_1, Y_1', Y_2, Y_2', Y_3, Y_3', Y_4$ and $Y_4'$ are respectively selected independently of one another from the group consisting of —H, —F, —Cl, —Br, —I, —CN, —$NO_2$, —CHO, —$R_0$, —C(=O)$R_0$, —C(=O)H, —C(=O)—OH, —C(=O)O$R_0$, —C(=O)$NH_2$, —C(=O)NH$R_0$, —C(=O)N($R_0$)$_2$, —OH, —O$R_0$, —OC(=O)H, —OC(=O)$R_0$, —OC(=O)O$R_0$, —OC(=O)NH$R_0$, —OC(=O)N($R_0$)$_2$, —SH, —S$R_0$, —$SO_3$H, —S(=O)$_{1-2}$—$R_0$, —S(=O)$_{1-2}$$NH_2$, —$NH_2$, —NH$R_0$, —N($R_0$)$_2$, —$N^+(R_0)_3$, —$N^+(R_0)_2O^-$, —NHC(=O)$R_0$, —NHC(=O)O$R_0$, —NHC(=O)$NH_2$, —NHC(=O)NH$R_0$ and —NHC(=O)N($R_o$)$_2$; or $Y_1$ and $Y_1'$, or $Y_2$ and $Y_2'$, or $Y_3$ and $Y_3'$, or $Y_4$ and $Y_4'$ jointly stand for =O;

Q stands for heteroaryl;

$R_0$ respectively independently stands for —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl, —$C_{1-8}$-aliphatic-heteroaryl, —$C_{3-8}$-cycloaliphatic-$C_{1-8}$-aliphatic, —$C_{3-8}$-cycloaliphatic-aryl or —$C_{3-8}$-cycloaliphatic-heteroaryl;

$R_1$ and $R_2$, independently of one another, stand for —H or —$R_0$; or $R_1$ and $R_2$ together stand for —$CH_2CH_2OCH_2CH_2$—, —$CH_2CH_2NR_4$—$CH_2CH_2$— or —$(CH_2)_{3-6}$—;

$R_3$ stands for —$R_0$;
$R_4$ stands for —H, —$R_0$ or —C(=O)$R_0$;

wherein
"aliphatic" respectively is a branched or unbranched, saturated or a mono- or polyunsaturated, unsubstituted or mono- or polysubstituted, aliphatic hydrocarbon residue;

"cycloaliphatic" respectively is a saturated or a mono- or polyunsaturated, unsubstituted or mono- or polysubstituted, alicyclic, mono- or multicyclic hydrocarbon residue;

wherein with respect to "aliphatic" and "cycloaliphatic", "mono- or polysubstituted" means the mono- or polysubstitution of one or more hydrogen atoms by substituents selected independently of one another from the group consisting of —F, —Cl, —Br, —I, —CN, —$NO_2$, —CHO, =O, —$R_0$, —C(=O)$R_0$, —C(=O)H, —C(=O)OH, —C(=O)O$R_0$, —C(=O)$NH_2$, —C(=O)NH$R_0$, —C(=O)N($R_0$)$_2$, —OH, —O$R_0$, —OC(=O)H, —OC(=O)$R_0$, —OC(=O)O$R_0$, —OC(=O)NH$R_0$, —OC(=O)N($R_0$)$_2$, —SH, —S$R_0$, —$SO_3$H, —S(=O)$_{1-2}$—$R_0$, —S(=O)$_{1-2}$$NH_2$, —$NH_2$, —NH$R_0$, —N($R_0$)$_2$, —$N^+(R_0)_3$, —$N^+(R_0)_2O^-$, —NHC(=O)$R_0$, —NHC(=O)O$R_0$, —NHC(=O)$NH_2$, —NHC(=O)—NH$R_0$, —NH—C(=O)N($R_0$)$_2$, —NHS(=O)$_{1-2}$$R_0$, —Si($R_0$)$_3$ and —PO(O$R_0$)$_2$;

"aryl", respectively independently, stands for a carbocyclic ring system with at least one aromatic ring, but without heteroatoms in this ring, wherein, if necessary, the aryl residues can be condensed with further saturated, (partially) unsaturated or aromatic ring systems, and each aryl residue can be present in unsubstituted or mono- or polysubstituted form, wherein the aryl substituents can be the same or different and in any desired and possible position of the aryl;

"heteroaryl" stands for a 5-membered cyclic aromatic residue, which contains 1 heteroatom selected from the group consisting of nitrogen, oxygen and sulphur, and is unsubstituted or mono- or polysubstituted; wherein in the case of substitution the substituents are the same or different and can be in any desired and possible position of the heteroaryl; and wherein the heteroaryl can also be part of a bi- or polycyclic system;

wherein with respect to "aryl" and "heteroaryl", "mono- or polysubstituted" means the mono- or polysubstitution of one or more hydrogen atoms of the ring system by substituents selected from the group consisting of —F, —Cl, —Br, —I, —CN, —NO$_2$, —CHO, =O, —R$_0$, —C(=O)R$_0$, —C(=O)H, —C(=O)OH, —C(=O)OR$_0$, —C(=O)NH$_2$, —C(=O)NHR$_0$, —C(=O)—N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NH—C(=O)NH$_2$, —NHC(=O)NHR$_0$, —NHC(=O)N(R$_0$)$_2$, —Si(R$_0$)$_3$, —PO(OR$_0$)$_2$, —C$_{1-8}$-aliphatic-NHC(=O)R$_0$, —C$_{1-8}$-aliphatic-NHC(=O)OR$_0$, —C$_{1-8}$-aliphatic-NHC(=O)NHR$_0$, —C$_{1-8}$-aliphatic-NHC(=O)N(R$_0$)$_2$ and —C$_{1-8}$-aliphatic-NHS(=O)$_{1-2}$R$_0$; wherein any N-ring atoms present can be respectively oxidised;

said compound being in the form of a single stereoisomer or mixture thereof, the free compound and/or a physiologically compatible salt thereof.

2. Compound according to claim 1, which has the formula (2):

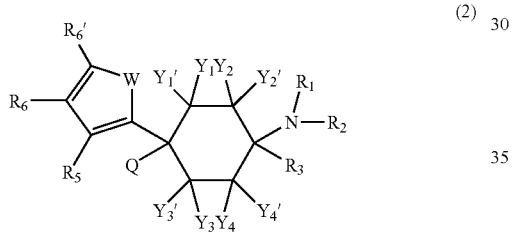

wherein

W stands for —O—, —S— or —NR$_{11}$—;

R$_5$, R$_6$, R$_6'$, and R$_{11}$ respectively independently of one another stand for —H, —F, —Cl, —Br, —I, —CN, —NO$_2$, —CHO, —R$_0$, —C(=O)R$_0$, —C(=O)H, —C(=O)OH, —C(=O)OR$_0$, —C(=O)NH$_2$, —C(=O)—NHR$_0$, —C(=O)—N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)—N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)—R$_0$, —NHC(=O)OR$_0$, —NH—C(=O)NH$_2$, —NHC(=O)NHR$_0$, —NHC(=O)N(R$_0$)$_2$; or R$_5$ and R$_6$, or R$_6$ and R$_6'$ together form a five- or six-membered, saturated, partially unsaturated or aromatic, which optionally contains one or two hetero ring atoms selected independently of one another from N, S and O; and which is unsubstituted or mono- or polysubstituted with substituents selected independently of one another from the group consisting of —F, —Cl, —Br, —I, —CF$_3$, —CN, —NO$_2$, —CHO, —R$_0$, —C(=O)R$_0$, —C(=O)H, —C(=O)OH, —C(=O)OR$_0$, —C(=O)NH$_2$, —C(=O)NHR$_0$, —C(=O)—N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)—N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)—R$_0$, —NHC(=O)OR$_0$, —NH—C(=O)NH$_2$, —NHC(=O)NHR$_0$ and —NHC(=O)N(R$_0$)$_2$.

3. Compound according to claim 1, which has the formula:

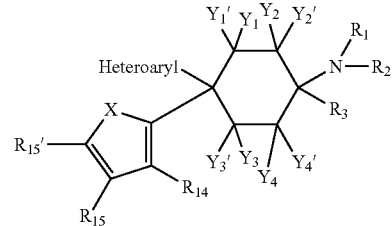

wherein

X stands for —O—, —S— or —NR$_{16}$—;

R$_{14}$, R$_{15}$, R$_{15}'$ and R$_{16}$ respectively independently of one another stand for —H, —F, —Cl, —Br, —I, —CN, —NO$_2$, —CHO, —R$_0$, —C(=O)R$_0$, —C(=O)H, —C(=O)OH, —C(=O)OR$_0$, —C(=O)NH$_2$, —C(=O)NHR$_0$, —C(=O)—N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NH—C(=O)NH$_2$, —NHC(=O)NHR$_0$, —NHC(=O)N(R$_0$)$_2$; or R$_{14}$ and R$_{15}$, or R$_{15}$ and R$_{15}'$ together form a five- or six-membered, saturated, partially unsaturated or aromatic ring, which optionally contains one or two hetero ring atoms selected independently of one another from N, S and O; and which is unsubstituted or mono- or polysubstituted with substituents selected independently of one another from the group consisting of —F, —Cl, —Br, —I, —CF$_3$, —CN, —NO$_2$, —CHO, —R$_0$, —C(=O)R$_0$, —C(=O)H, —C(=O)OH, —C(=O)OR$_0$, —C(=O)NH$_2$, —C(=O)NHR$_0$, —C(=O)—N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)—N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)—R$_0$, —NHC(=O)OR$_0$, —NH—C(=O)NH$_2$, —NHC(=O)NHR$_0$ and —NHC(=O)N(R$_0$)$_2$.

4. Compound according to claim 2, which has the formula:

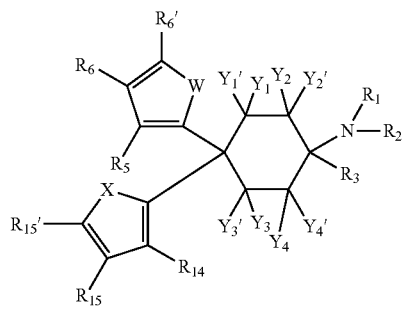

wherein

X stands for —O—, —S— or —NR$_{16}$—,

R$_{14}$, R$_{15}$, R$_{15}'$ and R$_{16}$ respectively independently of one another stand for —H, —F, —Cl, —Br, —I, —CN, —NO$_2$, —CHO, —R$_0$, —C(=O)R$_0$, —C(=O)H, —C(=O)OH, —C(=O)OR$_0$, —C(=O)NH$_2$, —C(=O)NHR$_0$, —C(=O)—N(R$_0$)$_2$, —OH, —O(CH$_2$)$_{1-2}$O— —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$—NH$_2$—NHR$_0$, —N(R$_0$)$_2$, —N$^+$(R$_0$)$_3$, —N$^+$(R$_0$)$_2$O$^-$; —NHC(=O)R$_0$, —NHC(=O)OR$_0$, —NH—C(=O)NH$_2$, —NHC(=O)NHR$_0$, —NHC(=O)N(R$_0$)$_2$; or R$_{14}$ and R$_{15}$ or R$_{15}$ and R$_{15}$' together form a five- or six-membered, saturated, partially unsaturated or aromatic ring, which optionally contains one or two hetero ring atoms selected independently of one another from N, S and O; and which is unsubstituted or mono- or polysubstituted with substituents selected independently of one another from the group consisting of —F, —Cl, —Br, —I, —CF$_3$, —CN, —NO$_2$, —CHO, —R$_0$, —C(=O)R$_0$, —C(=O)H, —C(=O)OH, —C(=O)OR$_0$, —C(=O)NH$_2$, —C(=O)NHR$_0$, —C(=O)—N(R$_0$)$_2$, —OH, —O(CH$_2$)$_{1-2}$O— —OR$_0$, —OC(=O)H, —OC(=O)R$_0$, —OC(=O)OR$_0$, —OC(=O)NHR$_0$, —OC(=O)—N(R$_0$)$_2$, —SH, —SR$_0$, —SO$_3$H, —S(=O)$_{1-2}$—R$_0$, —S(=O)$_{1-2}$NH$_2$, —NH$_2$—NHR$_0$, —N(R$_0$)$_2$, —N$^+$(R$_0$)$_3$, —N$^+$(R$_0$)$_2$O$^-$, —NHC(=O)—R$_0$, —NHC(=O)OR$_0$—NH—C(=O)NH$_2$, —NHC(=O)NHR$_0$ and —NHC(=O)N(R$_0$)$_2$.

5. Compound according to claim 4, which has the formula:

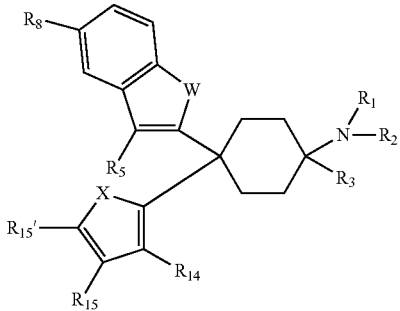

wherein

R$_8$ stands for —H, —F, —Cl, —Br, —I, —NO$_2$—CF$_3$, —OR$_{23}$, —SR$_{23}$, —SO$_2$R$_{23}$, —CN, —COOR$_{23}$, —CONR$_{23}$, —NR$_{24}$R$_{25}$ or —R$_0$.

6. Compound according to claim 5, wherein

W stands for —O— or —NR$_{11}$—;
X stands for —O— or —NR$_{16}$—;
n stands for 0 or 1;
R$_1$ stands for —CH$_3$;
R$_2$ stands for —H or —CH$_3$; or
R$_1$ and R$_2$ jointly form a ring and stand for —(CH$_2$)$_{3-4}$—;
R$_3$ stands for —C$_{1-8}$-aliphatic, -aryl or heteroaryl, wherein these are unsubstituted or mono- or polysubstituted with substituents selected independently of one another from the group consisting of —F, —Cl, —Br, —CN, —CH$_3$, —C$_2$H$_5$, —NH$_2$, —NO$_2$, —SH, —CF$_3$, —OH, —OCH$_3$, —OC$_2$H$_5$ and —N(CH$_3$)$_2$;
R$_5$ stands for —H, —F, —C$_{1-8}$-aliphatic, —C$_{1-8}$-aliphatic-aryl or —C$_{1-8}$-aliphatic-heteroaryl;
R$_8$ stands for —F, —Cl, —Br, —I, —CF$_3$, —CN or —NO$_2$;
R$_{11}$ stands for —H;
R$_{14}$, R$_{15}$ and R$_{15}$' independently of one another stand for —H, —F, —Cl, —Br, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$; or R$_{15}$ and R$_{15}$' jointly form a six-membered, saturated, partially unsaturated or aromatic ring, which can optionally contain one or two hetero ring atoms, which are selected independently of one another from N, S and O; wherein this formed ring can be unsubstituted or mono- or polysubstituted, wherein the substituents are selected independently of one another from the group consisting of —F, —Cl, —Br, —I, —CF$_3$, —CN and —NO$_2$;
R$_{16}$ stands for —H; and
R$_{17}$ and R$_{18}$ independently of one another stand for —H or —F.

7. Compound according to claim 1, which is selected from the group consisting of:
1-butyl-N,N-dimethyl-4,4-bis(3-methyl-5-(trifluoromethyl)-1H-indol-2-yl)cyclo-hexanamine;
1-butyl-4,4-bis(5-fluoro-3-methyl-1H-indol-2-yl)-N,N-dimethylcyclohexanamine;
1-benzyl-N,N-dimethyl-4,4-bis(3-(2-(pyridin-4-yl)ethyl)-1H-indol-2-yl)cyclohexanamine;
N,N-dimethyl-4,4-bis(3-(2-(pyridin-4-yl)ethyl)-1H-indol-2-yl)-1-(thiophen-2-yl)cyclo-hexanamine;
2,2'-(4-butyl-4-(pyrrolidin-1-yl)cyclohexane-1,1-diyl)bis(3-(2-(pyridin-4-yl)ethyl)-1H-indole);
N-methyl-1-phenyl-4,4-bis(3-(2-(pyridin-4-yl)ethyl)-1H-indol-2-yl)cyclohexanamine;
N,N-dimethyl-4-(3-methyl-1H-indol-2-yl)-1-phenyl-4-(thiophen-2-yl)cyclohexanamine;
N,N-dimethyl-4-(3-methyl-1H-indol-2-yl)-1-phenyl-4-(thiophen-2-yl)cyclohexanamine;
N,N-dimethyl-4,4-bis(3-methylbenzofuran-2-yl)-1-phenylcyclohexanamine;
N,N-dimethyl-4,4-bis(3-methyl-1H-indol-2-yl)-1-phenylcyclohexanamine;
1-butyl-N,N-dimethyl-4,4-bis(3-(2-(pyridin-4-yl)ethyl)-1H-indol-2-yl)-cyclohexanamine;
dimethyl 2,2'-(2,2'-(4-butyl-4-(dimethylamino)cyclohexan-1,1-diyl)bis(1H-indol-3,2-diyl))diacetate;
2,2'-(2,2'-(4-butyl-4-(dimethylamino)cyclohexan-1,1-diyl)bis(1H-indol-3,2-diyl))diethanol;
1-butyl-N,N-dimethyl-4-(3-methyl-1H-indol-2-yl)-4-(3-(2-(pyridin-4-yl)ethyl)-1H-indol-2-yl)cyclohexylamine;
1-butyl-4,4-bis-(3-(2-(3,4-dihydro-1H-isoquinolin-2-yl)ethyl)-1H-indol-2-yl)-N,N-dimethylcyclohexylamine;
1-butyl-N,N-dimethyl-4,4-bis-(3-methyl-1H-indol-2-yl)cyclohexylamine;
2-(2-(2-(4-butyl-4-dimethylamino-1-(3-methyl-1H-indol-2-yl)cyclohexyl)-1H-indol-3-yl)ethyl)isoindolin-1,3-dione;
2-[2-[2-[4-butyl-4-dimethylamino-1-[3-[2-(1,3-dioxo-2H-isoindol-2-yl)-ethyl]-1H-indol-2-yl]-cyclohexyl]-1H-indol-3-yl]-ethyl]-2H-isoindole-1,3-dione;
dimethyl 3,3'-(2-(4-butyl-4-(dimethylamino)cyclohexan-1,1-diyl)bis(1H-indol-2,3-diyl)dipropanate;
4-(3-(2-aminoethyl)-1H-indol-2-yl)-1-butyl-N,N-dimethyl-4-(3-methyl-1H-indol-2-yl)cyclohexylamine;
1-(3-fluorophenyl)-N,N-dimethyl-4-(3-methyl-1H-indol-2-yl)-4-thiophen-2-ylcyclohexylamine;
1-butyl-4,4-bis-(1,3-dimethyl-1H-indol-2-yl)-N,N-dimethylcyclohexylamine;
1-butyl-4-(1,3-dimethyl-1H-indol-2-yl)-N,N-dimethyl-4-(3-methyl-1H-indol-2-yl)cyclohexylamine;
1-benzyl-N,N-dimethyl-4-(3-methyl-1H-indol-2-yl)-4-(thiophen-2-yl)cyclohexylamine;

N-(2-(2-(4-butyl-4-(dimethylamino)-1-(3-methyl-1H-indol-2-yl)cyclohexyl)-1H-indol-3-yl)ethyl)cyclopentane sulphonamide;

1-(3-fluorophenyl)-N,N-dimethyl-4-(3-methyl-1H-indol-2-yl)-4-thiophen-2-ylcyclohexylamine;

N,N-dimethyl-1-phenyl-4,4-bis-(3-(2-(pyridin-4-yl)ethyl)-1H-indol-2-yl)cyclohexylamine;

1-(2-(2-(4-butyl-4-(dimethylamino)-1-(3-methyl-1H-indol-2-yl)cyclohexyl)-1H-indol-3-yl)ethyl)-3-phenylurea;

1,1'-(2,2'-(2,2'-(4-butyl-4(dimethylamino)cyclohexan-1,1-diyl)bis(1H-indol-3,2-diyl))bis(ethan-2,1-diyl)bis(3-phenylurea);

1-butyl-4,4-bis(5-fluoro-3-methyl-1H-indol-2-yl)-N,N-dimethylcyclohexylamine;

4-(3-(2-aminoethyl)-1H-indol-2-yl)-1-butyl-4-(5-fluoro-3-methyl-1H-indol-2-yl)-N,N-cyclohexylamine;

(phenyl-2-(2-(4-butyl-4-(dimethylamino)-1-(5-fluoro-3-methyl-1H-indol-2-yl)cyclohexyl)-1H-indol-3-yl)ethyl carbamate;

1-(2-(2-(4-butyl-4-(dimethylamino)-1-(5-fluoro-3-methyl-1H-indol-2-yl)cyclohexyl)-1H-indol-3-yl)ethyl)-3-phenylurea;

N,N-dimethyl-4-(3-methyl-1H-indol-2-yl)-1-phenyl-4-(3-(2-(pyridin-4-yl)ethyl)-1H-indol-2-yl)cyclohexylamine; and N,N-dimethyl-1-phenyl-4-(3-(2-(pyridin-4-yl)-ethyl)-1H-indol-2-yl)-4-(thiophen-2-yl)-cyclohexylamine;

or a physiologically compatible salt thereof.

8. A pharmaceutical composition comprising at least one compound according to claim 1, said compound being in the form of a single stereoisomer or mixture thereof, the free compound or a physiologically compatible salt thereof, and optionally suitable additives, adjuvants or further active substances.

9. A method of treating pain in a patient in need of such treatment, said method comprising administering to said patient an effective amount therefor of a compound according to claim 1, said compound being in the form of a single stereoisomer or mixture thereof, the free compound or a physiologically compatible salt thereof.

* * * * *